United States Patent
Mizuguchi et al.

(10) Patent No.: US 11,696,988 B2
(45) Date of Patent: Jul. 11, 2023

(54) AEROSOL INHALATOR, CONTROL DEVICE FOR THE SAME, METHOD OF CONTROLLING THE SAME, AND METHOD OF OPERATING CONTROL DEVICE FOR THE SAME AND PROGRAM

(71) Applicant: JAPAN TOBACCO INC., Tokyo (JP)

(72) Inventors: Kazuma Mizuguchi, Tokyo (JP); Takeshi Akao, Tokyo (JP); Takuma Nakano, Tokyo (JP); Masayuki Tsuji, Tokyo (JP); Hajime Fujita, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 16/714,864

(22) Filed: Dec. 16, 2019

(65) Prior Publication Data
US 2020/0197634 A1    Jun. 25, 2020

(30) Foreign Application Priority Data
Dec. 19, 2018 (JP) .............................. JP2018-236958

(51) Int. Cl.
*A61M 11/04* (2006.01)

(52) U.S. Cl.
CPC ..... *A61M 11/042* (2014.02); *A61M 2205/123* (2013.01); *A61M 2205/125* (2013.01); *A61M 2205/3334* (2013.01)

(58) Field of Classification Search
CPC .................... A61M 11/041–042; A61M 15/06
(Continued)

(56) References Cited

U.S. PATENT DOCUMENTS

2010/0313901 A1* 12/2010 Fernando ............... H02J 7/0042
                                                                131/330
2012/0048266 A1*  3/2012 Alelov .................. A61M 15/06
                                                                128/203.14
(Continued)

FOREIGN PATENT DOCUMENTS

EA        029524 B1     2/2014
EP      2047880 A1     4/2009
(Continued)

OTHER PUBLICATIONS

U.S. Appl. No. 62/719,017 cited in WIPO Publication 2020/037226 (Year: 2018).*
(Continued)

*Primary Examiner* — Valerie L Woodward
*Assistant Examiner* — Paige Kathleen Bugg
(74) *Attorney, Agent, or Firm* — Xsensus LLP

(57) ABSTRACT

To provide a control device for an aerosol inhalator capable of compensating changes in temperature of a heater due to inhalation.
A control device for an aerosol inhalator includes a first sensor for obtaining a first value relating to a temperature of a load which atomizes an aerosol source stored in a reservoir or retained by an aerosol base using heat generated by supply of electric power, a second sensor configured to detect an inhalation, and a controller, wherein the controller is configured to determine, based on a second value based on the first value and a threshold, whether the aerosol source in the reservoir or the aerosol base is depleted or insufficient (850A), and correct at least one of the second value and the threshold when detecting the inhalation (840) and, in the determination, compare the second value and the threshold, at least one of the second value and the threshold being corrected (842).

8 Claims, 24 Drawing Sheets

(58) Field of Classification Search
USPC .................................................. 128/200.14
See application file for complete search history.

(56) References Cited

U.S. PATENT DOCUMENTS

| | | | |
|---|---|---|---|
| 2013/0298905 A1* | 11/2013 | Levin | A24F 40/90 128/202.21 |
| 2013/0319435 A1 | 12/2013 | Flick | |
| 2014/0014126 A1* | 1/2014 | Peleg | A24F 40/57 374/54 |
| 2014/0020693 A1* | 1/2014 | Cochand | A24F 40/53 131/273 |
| 2015/0359263 A1* | 12/2015 | Bellinger | A24F 47/008 392/394 |
| 2016/0157524 A1* | 6/2016 | Bowen | G01N 33/0027 702/50 |
| 2017/0135406 A1* | 5/2017 | Reevell | H05B 3/04 |
| 2017/0245553 A1* | 8/2017 | Reevell | H05B 3/44 |
| 2017/0367410 A1* | 12/2017 | Hon | A24F 40/50 |
| 2018/0303161 A1 | 10/2018 | Bilat | |
| 2019/0380389 A1* | 12/2019 | Hong | A24F 40/95 |
| 2021/0243844 A1* | 8/2021 | Reevell | H05B 3/44 |

FOREIGN PATENT DOCUMENTS

| | | |
|---|---|---|
| EP | 2 468 116 A1 | 6/2012 |
| JP | 2014-501107 A | 1/2014 |
| JP | 2017-521076 A | 8/2017 |
| KR | 10-2014-0004656 | 1/2014 |
| KR | 10-2018-0115678 | 10/2018 |
| TW | 201803469 A | 2/2018 |
| WO | 2012/085203 A1 | 6/2012 |
| WO | 2017/084818 A1 | 5/2017 |
| WO | 2017/144374 A1 | 8/2017 |
| WO | 2018/019533 A1 | 2/2018 |
| WO | WO-2020037226 A1 * | 2/2020 ............. A24F 40/10 |

OTHER PUBLICATIONS

Decision to Grant a Patent received for Japanese Patent Application No. 2018-236958, dated Apr. 1, 2019, 5 pages inluding English Translation.
Office Action dated Apr. 10, 2020 in Korean Patent Application No. 10-2019-0164431, 18 pages.
Eurasian Office Action dated Mar. 5, 2020, in corresponding Eurasian Patent Application No. 201992714 and English translation thereof.
Eurasian Office Action dated Mar. 5, 2020, in corresponding Eurasian Patent Application No. 201992713 and English translation thereof.
Eurasian Search Report dated Dec. 13, 2019 in Eurasian application No. 201992713.
Eurasian Search Report dated Dec. 13, 2019 in Eurasian application No. 201992714.
Partial European Search Report dated May 15, 2020, issued in corresponding European Patent Application No. 19216989.4.
Taiwanese Office Action dated May 29, 2020 in Taiwanese Application No. 108143937.
Extended European search report dated Sep. 10, 2020, in corresponding to European Patent Application No. 19216989.4, 13 pages.

* cited by examiner

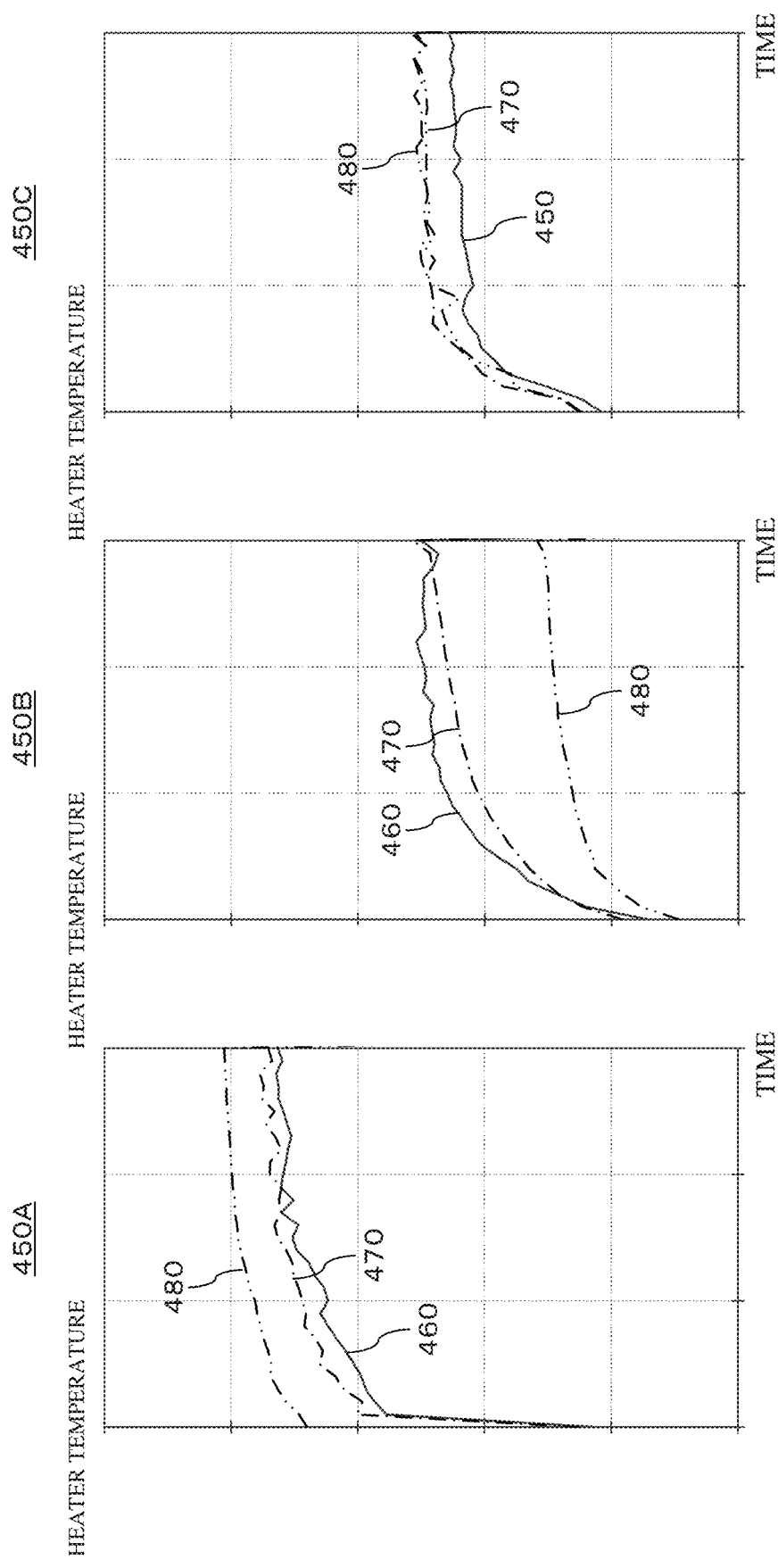

AEROSOL INHALATOR, CONTROL DEVICE FOR THE SAME, METHOD OF CONTROLLING THE SAME, AND METHOD OF OPERATING CONTROL DEVICE FOR THE SAME AND PROGRAM

CROSS-REFERENCE TO RELATED APPLICATION

The present application claims priority to JP 2018-236958, filed Dec. 19, 2018, the entire contents of which are incorporated herein by reference.

TECHNICAL FIELD

The present disclosure relates to an aerosol inhalator that generates aerosol inhaled by a user, a control device for the aerosol inhalator, a method of controlling the aerosol inhalator, and a method of operating the control device for the aerosol inhalator, and a program. Note that the aerosol inhalator is also referred to as an aerosol generation device.

BACKGROUND ART

An aerosol inhalator for generating aerosol inhaled by a user, such as a general electronic cigarette, a heat cigarette, or a nebulizer cannot supply sufficient aerosol to the user when the user inhales aerosol in a state in which an aerosol source (hereinafter, also referred to as an aerosol-forming substrate) which is to be atomized to generate aerosol is insufficient. In addition, in the case of the electronic cigarette and the heat cigarette, there is a problem in that aerosol having intended smoke flavor cannot be generated.

As a solution to this problem, Patent Literature 1 discloses a technique for determining that an aerosol-forming substrate has run out, based on the rate of increase of the heater temperature at the initial power supply and a threshold. Patent Literature 2 discloses a technique for determining that an aerosol-forming substrate has run out, based on a heater temperature after a predetermined time period elapses from the start of power supply or the rate of increase of the heater temperature at the initial power supply while the heater is not operating.

However, although the behavior of the heater temperature may be influenced by the inhalation of aerosol by a user, in the technique disclosed in Patent Literature 1 or 2, such a point is not taken into consideration.

CITATION LIST

Patent Literature

PTL1: International Publication No. WO 2012/085203
PTL2: International Publication No. WO 2017/084818

SUMMARY OF INVENTION

Technical Problem

The present disclosure has been devised in view of the point described above.

A first problem to be solved by the present disclosure is to provide an aerosol inhalator capable of compensating changes in temperature of a heater due to inhalation, a control device for the aerosol inhalator, a method of controlling the aerosol inhalator, and a method of operating the control device for the aerosol inhalator, and a program.

A second problem to be solved by the present disclosure is to provide an aerosol inhalator capable of determining a residual amount of an aerosol source without being influenced by changes in temperature of a heater due to inhalation, a control device for the aerosol inhalator, a method of controlling the aerosol inhalator, and a method of operating the control device for the aerosol inhalator, and a program.

Solution to Problem

In order to solve the first problem described above, according to an embodiment of the present disclosure, there is provided a control device for an aerosol inhalator comprising: a first sensor for obtaining a first value relating to a temperature of a load which atomizes an aerosol source stored in a reservoir or retained by an aerosol base using heat generated by supply of electric power; a second sensor configured to detect an inhalation; and a controller, wherein the controller is configured to determine, based on a second value based on the first value and a threshold, whether the aerosol source in the reservoir or the aerosol base is depleted or insufficient, and correct at least one of the second value and the threshold when detecting the inhalation, and, in the determination, compare the second value and the threshold, at least one of the second value and the threshold being corrected.

According to the embodiment, since a value based on the value relating to the heater temperature or a threshold for determining depletion or insufficiency of the aerosol source is corrected when inhalation is performed during aerosol generation, it can be properly determined whether depletion or insufficiency of the aerosol source has occurred regardless of the presence or absence of the inhalation.

According to the embodiment, since it can be properly determined whether depletion or insufficiency of the aerosol source has occurred, an energy saving effect can be obtained that the aerosol source can be replaced with new aerosol source after being sufficiently consumed.

In an embodiment, the second sensor or the controller may be configured to obtain a value relating to a strength of the inhalation, and the controller may be configured to change or adjust an amount of correction of the second value or the threshold according to the value relating to the strength.

According to the embodiment, since a value based on the value relating to the heater temperature or a threshold for determining depletion or insufficiency of the aerosol source is corrected according to the inhalation strength (velocity, magnitude of a pressure change, and the like), it can be properly determined whether depletion or insufficiency of the aerosol source has occurred even when any strong inhalation is performed.

In an embodiment, the aerosol inhalator may be configured to decrease a temperature of the load when the inhalation is performed during power supply to the load or during aerosol generation of the load, and the controller may be configured to, when detecting the inhalation, correct the second value to be increased or the threshold to be decreased when the first value is decreased when the temperature of the load is decreased, and to correct the second value to be decreased or the threshold to be increased when the first value is increased when the temperature of the load is decreased.

According to the embodiment, in a system in which the heater temperature is decreased due to the inhalation, when the inhalation is performed, a value or a threshold is corrected based on whether the value based on the value relating to the heater temperature is decreased or increased due to the decrease in heater temperature (in other words, the value is increased or decreased due to the heater temperature rise). Accordingly, in the system in which the heater temperature is decreased due to the inhalation, it can be properly determined whether depletion or insufficiency of the aerosol source has occurred regardless of the presence or absence of the inhalation.

In an embodiment, the aerosol inhalator may be configured to increase the temperature of the load when the inhalation is performed during the power supply to the load or during the aerosol generation of the load, and the controller may be configured to, when detecting the inhalation, correct the second value to be decreased or the threshold to be increased when the first value is increased when the temperature of the load is increased, and to correct the second value to be increased or the threshold to be decreased when the first value is decreased when the temperature of the load is increased.

According to the embodiment, in a system in which the heater temperature is increased due to the inhalation, when the inhalation is performed, a value or a threshold is corrected based on whether the value based on the value relating to the heater temperature is increased or decreased due to the heater temperature rise. Accordingly, in the system in which the heater temperature is increased due to the inhalation, it can be properly determined whether depletion or insufficiency of the aerosol source has occurred regardless of the presence or absence of the inhalation.

In order to solve the first problem described above, according to an embodiment of the present disclosure, there is provided an aerosol inhalator comprising: the control device for an aerosol inhalator; a channel in which air taken by the inhalation flows; and the load disposed in a position not to be in contact with the air outside and inside the channel, wherein the controller is configured to, when detecting the inhalation, correct the second value to be decreased or the threshold to be increased when the first value is increased when the temperature of the load is increased, and correct the second value to be increased or the threshold to be decreased when the first value is decreased when the temperature of the load is increased.

According to the embodiment, in a system in which the load is disposed in a position not to be in contact with the air outside or drawn inside the channel, when the inhalation is performed, a value or a threshold is corrected based on whether the value based on the value relating to the heater temperature is increased or decreased due to the heater temperature rise. Accordingly, in such a system, it can be properly determined whether depletion or insufficiency of the aerosol source has occurred regardless of the presence or absence of the inhalation.

In order to solve the first problem described above, according to an embodiment of the present disclosure, there is provided an aerosol inhalator comprising: the control device for the aerosol inhalator according to claim 1; an outer tube; an inner tube disposed in the outer tube; the reservoir disposed or formed between the outer tube and the inner tube; the load disposed in the inner tube; and a retainer retained in a position where the load is capable of heating the aerosol source supplied by the reservoir, wherein the controller is configured to, when detecting the inhalation, correct at least one of the second value and the threshold by a constant amount regardless of a strength of the inhalation.

According to the embodiment, in a system in which the strength of the inhalation does not significantly influence a change in the heater temperature, since a constant amount of correction is performed regardless of the strength of the inhalation, the control device can be simplified, and furthermore, the cost, weight, and volume can be reduced.

In an embodiment, the controller may be configured to, when detecting the inhalation, correct only the threshold of the second value and the threshold.

According to the embodiment, since the threshold which is a fixed value is corrected as compared with a value relating to the heater temperature in which the sensor error is easily included in the output value and the discrete value is easily taken, the accuracy of the determination for depletion or insufficiency of the aerosol source can be ensured even when the correction accompanied with the inhalation is performed.

The control device for an aerosol inhalator in an embodiment comprises: a first circuit having a first switch; and a second circuit having a second switch, and having a resistance value higher than the resistance value of the first circuit and connected in parallel to the first circuit, wherein the first sensor may be configured to output, as the first value, a value relating to a resistance value of the load which changes depending on a temperature, and the controller may be configured to determine occurrence of the depletion or the insufficiency based on the first value while only the second circuit of the first circuit and the second circuit functions.

According to the embodiment, since the heater temperature is detected using the second circuit having a higher resistance value, the noise is hardly superimposed on the heater temperature as compared with a case where the first circuit having a lower resistance value is used, and therefore it can be properly determined whether the depletion or insufficiency of the aerosol source has occurred.

In order to solve the first problem described above, according to an embodiment of the present disclosure, there is provided a method of operating a control device for an aerosol inhalator, the control device comprising: a first sensor for obtaining a first value relating to a temperature of a load which atomizes an aerosol source stored in a reservoir or retained by an aerosol base using heat generated by supply of electric power; a second sensor configured to detect an inhalation; and a controller, the method comprising, by the controller: determining depletion or insufficiency of the aerosol source in the reservoir or the aerosol base based on a second value based on the first value and a threshold comprising correcting at least one of the second value and the threshold, and comparing the second value and the threshold, at least one of the second value of the threshold being corrected.

According to the embodiment, since a value based on the value relating to the heater temperature or a threshold for determining depletion or insufficiency of the aerosol source is corrected when the inhalation is performed during aerosol generation, it can be properly determined whether depletion or insufficiency of the aerosol source has occurred regardless of the presence or absence of the inhalation.

According to the embodiment, since it can be properly determined whether depletion or insufficiency of the aerosol source has occurred, an energy saving effect can be obtained that the aerosol source can be replaced with new aerosol source after being sufficiently consumed.

In order to solve the first problem described above, according to an embodiment of the present disclosure, there is provided a control device for an aerosol inhalator comprising: a first sensor for obtaining a first value relating to a temperature of a load which atomizes an aerosol source stored in a reservoir or retained by an aerosol base using heat generated by supply of electric power; a second sensor configured to detect an inhalation; and a controller, wherein the controller is configured to determine, based on a second value based on the first value and a threshold, whether the aerosol source in the reservoir or the aerosol base is depleted or insufficient, and, when detecting the inhalation, in the determination, the second value is compared with a threshold different from the threshold when the inhalation has not been detected.

In order to solve the first problem described above, according to an embodiment of the present disclosure, there is provided a method of operating a control device for an aerosol inhalator, the control device comprising: a first sensor for obtaining a first value relating to a temperature of a load which atomizes an aerosol source stored in a reservoir or retained by an aerosol base using heat generated by supply of electric power; a second sensor configured to detect an inhalation; and a controller, the method comprising, by the controller: determining depletion or insufficiency of the aerosol source in the reservoir or the aerosol base based on a second value based on the first value and a threshold comprising obtaining a threshold different depending on whether the inhalation has been detected, and comparing the second value and the obtained threshold.

According to the embodiment, since thresholds different between the case where the inhalation is performed during the aerosol generation and the case where the inhalation is not performed during the aerosol generation can be used, it can be properly determined whether depletion or insufficiency of the aerosol source has occurred regardless of the presence or absence of the inhalation.

According to the embodiment, since it can be properly determined whether depletion or insufficiency of the aerosol source has occurred, an energy saving effect can be obtained that the aerosol source can be replaced with new aerosol source after being sufficiently consumed.

In order to solve the first problem described above, according to an embodiment of the present disclosure, there is provided a control device for an aerosol inhalator comprising: a first sensor for obtaining a first value relating to a temperature of a load which atomizes an aerosol source stored in a reservoir or retained by an aerosol base using heat generated by supply of electric power; a second sensor configured to detect an inhalation; and a controller, wherein the controller is configured to obtain a temperature of the load or a time-series change in temperature of the load based on the first value, and, when detecting the inhalation, correct the temperature of the load or the time-series change in temperature of the load.

In order to solve the first problem described above, according to an embodiment of the present disclosure, there is provided a method of operating a control device for an aerosol inhalator, the control device comprising: a first sensor for obtaining a first value relating to a temperature of a load which atomizes an aerosol source stored in a reservoir or retained by an aerosol base using heat generated by supply of electric power; a second sensor configured to detect an inhalation; and a controller, the method comprising, by the controller: obtaining a temperature of the load or a time-series change in temperature of the load based on the first value, and correcting, when detecting the inhalator, the temperature of the load or the time-series change in temperature of the load.

According to the embodiment, since the heater temperature or the temperature profile is corrected when the inhalation is detected, the proper heater temperature or temperature profile can be obtained regardless of the presence or absence of the inhalation.

According to the embodiment, since it can be properly determined whether depletion or insufficiency of the aerosol source has occurred, an energy saving effect can be obtained that the aerosol source can be replaced with new aerosol source after being sufficiently consumed.

In an embodiment, the second value may be any one of the first value, a value of a ratio between a change amount of the first value due to an amount of electric power supplied to the load and the amount of electric power supplied, and a value of a ratio between a change amount of the first value over time and a length of the time elapsed.

According to the embodiment, since various values based on a value relating to the heater temperature can be used, the degree of freedom in design can be enhanced.

In order to solve the first problem described above, according to an embodiment of the present disclosure, there is provided a program that causes a processor to perform the method when executed by the processor.

According to the embodiment, when inhalation is performed during aerosol generation, any one of a value based on a value relating to the heater temperature, a threshold for determining depletion or insufficiency of the aerosol source and the heater temperature or the temperature profile is corrected, or a threshold different from the case where the inhalation is not performed is used. Accordingly, it can be properly determined whether depletion or insufficiency of the aerosol source has occurred regardless of the presence or absence of the inhalation, or the proper heater temperature or temperature profile can be obtained.

In order to solve the second problem described above, according to an embodiment of the present disclosure, there is provided a control device for an aerosol inhalator, the aerosol inhalator being configured so that a temperature, during supply of an electric power or during aerosol generation, of the load which atomizes an aerosol source stored in a reservoir or retained by an aerosol base using heat generated by supply of electric power become higher when an inhalation is performed, the control device comprising a sensor for obtaining a first value relating to a temperature of the load, and a controller, wherein the controller is configured to determine depletion or insufficiency of the aerosol source in the reservoir or the aerosol base based on a comparison between a second value based on the first value and a threshold, the threshold is a value obtained by adding a positive first predefined value to the second value when a first condition that a residual amount of the aerosol source in the reservoir or the aerosol base is sufficient and the aerosol is being generated in the load is satisfied, and the inhalation is not performed, in a case where the first value is increased when the temperature of the load is increased, and the threshold is a value obtained by subtracting the positive first predefined value from the second value when the first condition is satisfied and the inhalation is not performed, in a case where the first value is decreased when the temperature of the load is increased.

According to the embodiment, in a system in which the heater temperature is increased due to the inhalation, since a value obtained by increasing or decreasing a predefined value based on whether a value based on a value relating to a heater temperature when the heater temperature has reached an aerosol generation temperature is increased or decreased due to a heater temperature rise is used for a threshold for determining depletion or insufficiency of an aerosol source, the accuracy of determining whether the depletion or the insufficiency of the aerosol source has occurred can be improved even when the heater temperature or the threshold is not corrected according to the presence or absence of the inhalation.

According to the embodiment, since it can be properly determined whether depletion or insufficiency of the aerosol source has occurred, an energy saving effect can be obtained that the aerosol source can be replaced with new aerosol source after being sufficiently consumed.

In an embodiment, the first predefined value may be an absolute value of a difference between the second value when the first condition is satisfied and the inhalation is not performed and the second value when the first condition is satisfied and the inhalation is performed.

In an embodiment, the first predefined value may be an absolute value of a difference between the second value when the first condition is satisfied and the inhalation is not performed and the second value when the first condition is satisfied and the inhalation of 55 cc per 3 seconds is performed.

According to the embodiment, since a predefined value (buffer) provided when a threshold is calculated results from the inhalation, it can be properly determined whether depletion or insufficiency of the aerosol source has occurred regardless of the presence or absence of the inhalation.

In an embodiment, the first value is increased when a temperature of the load is increased, and the controller may be configured to determine an occurrence of the depletion or the insufficiency only when it is detected a plurality of times that the second value is larger than the threshold.

In an embodiment, the first value is decreased when a temperature of the load is increased, and the controller may be configured to determine an occurrence of the depletion or the insufficiency only when it is detected a plurality of times that the second value is smaller than the threshold.

According to the embodiment, since the depletion or the insufficiency of the aerosol source is not determined unless the relationship of large and small magnitudes between the value based on the value relating to the heater temperature and the threshold satisfies a condition that the depletion or the insufficiency of the aerosol source is suspected a plurality of times, the occurrence of the depletion or the insufficiency of the aerosol source can be more surely detected.

In an embodiment, the first predefined value may be an absolute value of a difference between the second value at steady state when the depletion or the insufficiency has occurred, electric power is supplied to the load, and the inhalation is not performed, and the second value when the first condition is satisfied and the inhalation is not performed.

According to the embodiment, since the occurrence of the depletion or the insufficiency of the aerosol source is detected only when the heater temperature is equal to or higher than a temperature when the aerosol source is depleted or insufficient regardless of the presence or absence of the inhalation, the occurrence of the depletion or the insufficiency of the aerosol source can be more surely detected.

In an embodiment, the first predefined value may be an value obtained by adding a positive second predefined value to an absolute value of a difference between the second value at steady state when a second condition that the depletion or the insufficiency has occurred and electric power is being supplied to the load is satisfied, and the inhalation is not performed and the second value when the first condition is satisfied and the inhalation is not performed.

According to the embodiment, since a value obtained by adding a predefined value to the temperature when the aerosol source is depleted or insufficient is used for a threshold for determining depletion or insufficiency of an aerosol source, the accuracy of determining whether the depletion or the insufficiency of the aerosol source has occurred can be improved even when inhalation is performed when a liquid is depleted.

In an embodiment, the second predefined value may be an absolute value of a difference between the second value at steady state when the second condition is satisfied and the inhalation is not performed and the second value at steady state when the second condition is satisfied and the inhalation is performed.

In an embodiment, the second predefined value may be an absolute value of a difference between the second value at steady state when the second condition is satisfied and the inhalation is not performed and the second value at steady state when the second condition is satisfied and the inhalation of 55 cc per 3 seconds is performed.

According to the embodiment, since a second predefined value (buffer) provided when a threshold is calculated results from the inhalation, it can be properly determined whether depletion or insufficiency of the aerosol source has occurred regardless of the presence or absence of the inhalation when the aerosol source is depleted or insufficient.

In an embodiment, the first value is increased when a temperature of the load is increased, and the controller may be configured to determine an occurrence of the depletion or the insufficiency when it is detected one time that the second value is larger than the threshold.

In an embodiment, the first value is decreased when a temperature of the load is increased, and the controller may be configured to determine an occurrence of the depletion or the insufficiency when it is detected one time that the second value is smaller than the threshold.

According to the embodiment, in the case where the occurrence of the depletion or the insufficiency of the aerosol source is strongly suspected, it is determined that the depletion or the insufficiency of the aerosol source has occurred when the relationship of large and small magnitudes between the value based on the value relating to the heater temperature and the threshold satisfies, at least one time, the condition that the depletion or the insufficiency of the aerosol source is suspected. Accordingly, the quality of the product and the determination speed can be increased.

In order to solve the second problem described above, according to an embodiment of the present disclosure, there is provided an aerosol inhalator comprising: the control device for an aerosol inhalator; a channel in which air taken by the inhalation flows; and the load disposed in a position not to be in contact with the air which is taken in by the inhalation and is outside and inside the channel.

In order to solve the second problem described above, according to an embodiment of the present disclosure, there is provided a method of operating a control device for an aerosol inhalator, the aerosol inhalator being configured so that a temperature, during supply of an electric power or during aerosol generation, of the load which atomizes an aerosol source stored in a reservoir or retained by an aerosol base using heat generated by supply of electric power become higher when an inhalation is performed, the control device comprising a sensor for obtaining a first value relating to a temperature of the load and a controller, the method comprising, by the controller: determining depletion or insufficiency of the aerosol source in the reservoir or the aerosol base based on a comparison between a second value based on the first value and a threshold, wherein the threshold is a value obtained by adding a positive first predefined value to the second value when a first condition that a residual amount of the aerosol source in the reservoir or the aerosol base is sufficient and the aerosol is being generated in the load is satisfied and the inhalation is not performed, in a case where the first value is increased when the temperature of the load is increased, and the threshold is a value obtained by subtracting the positive first predefined value from the second value when the first condition is satisfied and the inhalation is not performed, in a case where the first value is decreased when the temperature of the load is increased.

According to the embodiment, in a system in which the heater temperature is increased due to the inhalation, since a value obtained by increasing or decreasing a predefined value based on whether a value based on a value relating to a heater temperature when the heater temperature has reached an aerosol generation temperature is increased or decreased due to a heater temperature rise is used for a threshold for determining depletion or insufficiency of an aerosol source, the accuracy of determining whether the depletion or the insufficiency of the aerosol source has occurred can be improved even when the heater temperature or the threshold is not corrected according to the presence or absence of the inhalation.

According to the embodiment, since it can be properly determined whether depletion or insufficiency of the aerosol source has occurred, an energy saving effect can be obtained that the aerosol source can be replaced with new aerosol source after being sufficiently consumed.

In order to solve the second problem described above, according to an embodiment of the present disclosure, there is provided a control device for an aerosol inhalator, the aerosol inhalator being configured so that a temperature, during supply of an electric power or during aerosol generation, of the load which atomizes an aerosol source stored in a reservoir or retained by an aerosol base using heat generated by supply of electric power become lower when an inhalation is performed, the control device comprising a sensor for obtaining a first value relating to a temperature of the load and a controller, wherein the controller is configured to determine depletion or insufficiency of the aerosol source in the reservoir or the aerosol base based on a comparison between a second value based on the first value and a threshold, the threshold is equal to or larger than the second value when a first condition that a residual amount of the aerosol source in the reservoir or the aerosol base is sufficient and the aerosol is being generated in the load is satisfied, and the inhalation is not performed, in a case where the first value is increased when a temperature of the load is increased, and the threshold is equal to or lower than the second value when the first condition is satisfied and the inhalation is not performed, in a case where the first value is decreased when a temperature of the load is increased.

According to the embodiment, in a system in which the heater temperature is decreased due to the inhalation, since a proper threshold for determining depletion or insufficiency of the aerosol source is used, the accuracy of determining whether the depletion or the insufficiency of the aerosol source has occurred can be improved even when the heater temperature or the threshold is not corrected according to the presence or absence of the inhalation.

According to the embodiment, since it can be properly determined whether depletion or insufficiency of the aerosol source has occurred, an energy saving effect can be obtained that the aerosol source can be replaced with new aerosol source after being sufficiently consumed.

In an embodiment, the first value is increased when a temperature of the load is increased, and the controller may be configured to determine an occurrence of the depletion or the insufficiency only when it is detected a plurality of times that the second value is larger than the threshold.

In an embodiment, the first value is decreased when a temperature of the load is increased, and the controller may be configured to determine an occurrence of the depletion or the insufficiency only when it is detected a plurality of times that the second value is smaller than the threshold.

According to the embodiment, since the depletion or the insufficiency of the aerosol source is not determined unless the relationship of large and small magnitudes between the value based on the value relating to the heater temperature and the threshold satisfies a condition that the depletion or the insufficiency of the aerosol source is suspected a plurality of times, the occurrence of the depletion or the insufficiency of the aerosol source can be more surely detected.

In an embodiment, in a case where the first value is increased when a temperature of the load is increased, the threshold may be equal to or larger than a value obtained by subtracting a positive predefined value from the second value at steady state when a third condition that the depletion or the insufficient has occurred and electric power is being supplied to the load is satisfied and the inhalation is not performed, and in a case where the first value is decreased when a temperature of the load is increased, the threshold may be equal to or less than a value obtained by adding the positive predefined value to the second value at steady state when the third condition is satisfied and the inhalation is not performed.

According to the embodiment, since a value obtained by increasing or decreasing a predefined value based on whether a value based on a value relating to a heater temperature when the aerosol source is depleted or insufficient is increased or decreased due to a heater temperature rise is used for a threshold for determining depletion or insufficiency of the aerosol source, the accuracy of determining whether the depletion or the insufficiency of the aerosol source has occurred can be improved even when the heater temperature or the threshold is not corrected according to the presence or absence of the inhalation.

In an embodiment, the predefined value may be an absolute value of a difference between the second value at steady state when the third condition is satisfied and the inhalation is not performed and the second value at steady state when the third condition is satisfied and the inhalation is performed.

In an embodiment, the predefined value may be an absolute value of a difference between the second value at steady state when the third condition is satisfied and the inhalation is not performed and the second value at steady state when the third condition is satisfied and the inhalation of 55 cc per 3 seconds is performed.

According to the embodiment, since a predefined value (buffer) provided when a threshold is calculated results from the inhalation, it can be properly determined whether depletion or insufficiency of the aerosol source has occurred regardless of the presence or absence of the inhalation.

In an embodiment, the first value is increased when a temperature of the load is increased, and the controller may be configured to determine an occurrence of the depletion or the insufficiency when it is detected one time that the second value is larger than the threshold.

In an embodiment, the first value is decreased when a temperature of the load is increased, and the controller may be configured to determine an occurrence of the depletion or the insufficiency when it is detected one time that the second value is smaller than the threshold.

According to the embodiment, in the case where the occurrence of the depletion or the insufficiency of the aerosol source is strongly suspected, it is determined that the depletion or the insufficiency of the aerosol source has occurred when the relationship of large and small magnitudes between the value based on the value relating to the heater temperature and the threshold satisfies, at least one time, the condition that the depletion or the insufficiency of the aerosol source is suspected. Accordingly, the quality of the product and the determination speed can be increased.

In order to solve the second problem described above, according to an embodiment of the present disclosure, there is provided an aerosol inhalator comprising: the control device for the aerosol inhalator; an outer tube; an inner tube disposed in the outer tube; the reservoir disposed or formed between the outer tube and the inner tube; the load disposed in the inner tube; and a retainer retained in a position where the load is capable of heating the aerosol source supplied by the reservoir.

In order to solve the second problem described above, according to an embodiment of the present disclosure, there is provided a method of operating a control device for an aerosol inhalator, the aerosol inhalator being configured so that a temperature, during supply of an electric power or during aerosol generation, of the load which atomizes an aerosol source stored in a reservoir or retained by an aerosol base using heat generated by supply of electric power become lower when an inhalation is performed, the control device comprising a sensor for obtaining a first value relating to a temperature of the load and a controller, the method comprising, by the controller: determining depletion or insufficiency of the aerosol source in the reservoir or the aerosol base based on a comparison between a second value based on the first value and a threshold, wherein the threshold is equal to or larger than the second value when a first condition that a residual amount of the aerosol source in the reservoir or the aerosol base is sufficient and the aerosol is being generated in the load is satisfied and the inhalation is not performed, in a case where the first value is increased when a temperature of the load is increased, and the threshold is equal to or lower than the second value when the first condition is satisfied and the inhalation is not performed, in a case where the first value is decreased when a temperature of the load is increased.

According to the embodiment, in a system in which the heater temperature is decreased due to the inhalation, since a proper threshold for determining depletion or insufficiency of the aerosol source is used, the accuracy of determining whether the depletion or the insufficiency of the aerosol source has occurred can be improved even when the heater temperature or the threshold is not corrected according to the presence or absence of the inhalation.

According to the embodiment, since it can be properly determined whether depletion or insufficiency of the aerosol source has occurred, an energy saving effect can be obtained that the aerosol source can be replaced with new aerosol source after being sufficiently consumed.

In an embodiment, the second value may be any one of the first value, a value of a ratio between a change amount of the first value due to an amount of electric power supplied to the load and the amount of electric power supplied, and a value of a ratio between a change amount of the first value over time and a length of the time elapsed.

According to the embodiment, since various values based on a value relating to the heater temperature can be used, the degree of freedom in design can be enhanced.

In order to solve the second problem described above, according to an embodiment of the present disclosure, there is provided a program that causes a processor to perform the method when executed by the processor.

According to the embodiment, since a proper threshold for determining depletion or insufficiency of the aerosol source is used even in both of a system in which the heater temperature is increased due to the inhalation and a system in which the heater temperature is decreased due to the inhalation, and even when the value based on the value relating to the heater temperature is increased or decreased due to the heater temperature rise, the accuracy of determining whether the depletion or the insufficiency of the aerosol source has occurred can be improved even when the heater temperature or the threshold is not corrected according to the presence or absence of the inhalation.

BRIEF DESCRIPTION OF DRAWINGS

FIG. 4B shows graphs showing exemplary temperature profiles of loads of the aerosol inhalators having various structures, respectively.

Figure 1A:
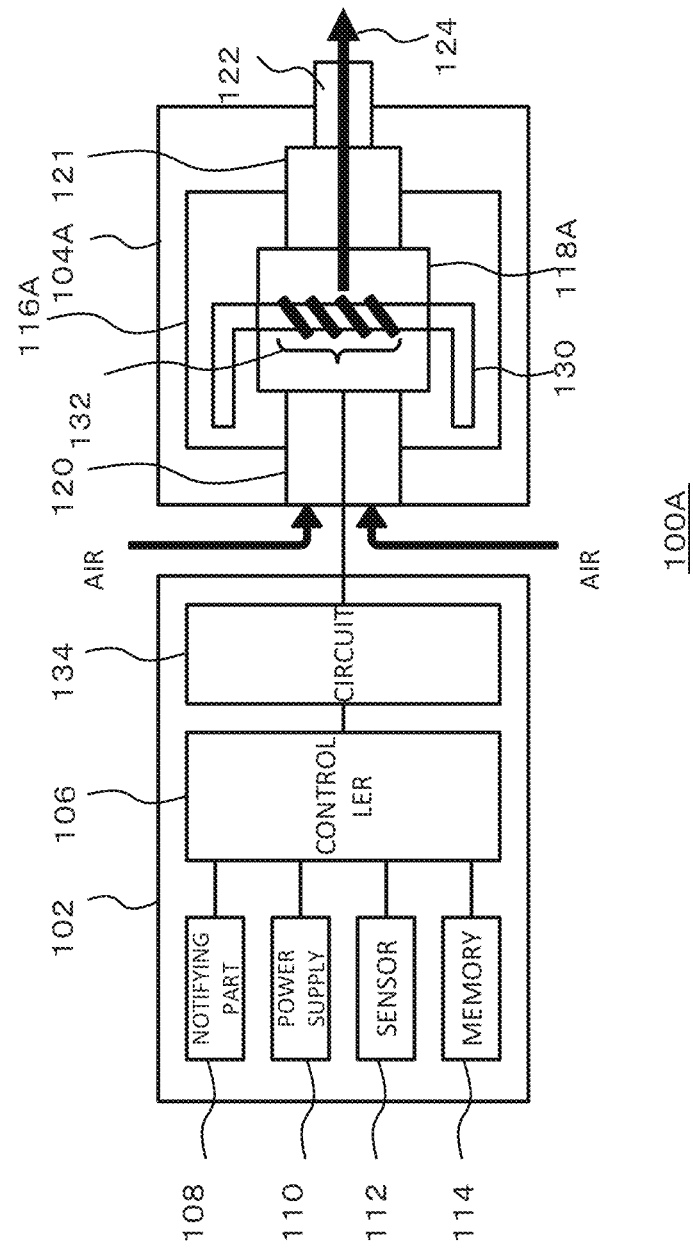
FIG. 1A is a schematic block diagram of a configuration of an aerosol inhalator according to an embodiment of the present disclosure.

The suction port part 122 is located at a terminal end of the aerosol flow path 121 and configured to open the aerosol flow path 121 to the outside of the aerosol inhalator 100A. The user holds the suction port part 122 in the user's mouth and inhales the air including the aerosol to thereby take the air including the aerosol into the oral cavity.

The notifying part 108 may include a light emitting element such as an LED, a display, a speaker, a vibrator or the like. The notifying part 108 is configured to perform some notification to the user with light emission, display, sound production, vibration, or the like according to necessity.

Note that the cartridge 104A can be configured as an outer tube, and one or both of the air intake channel 120 and the aerosol flow path 121 can be configured as inner tubes disposed in the outer tube. The load 132 can be disposed in the air intake channel 120 or the aerosol flow path 121 which is an inner tube. The reservoir 116A can be disposed or formed between the cartridge 104A which is an outer tube and the air intake channel 120 or the aerosol flow path 121 which is an inner tube.

The power supply 110 supplies electric power to the components of the aerosol inhalator 100A such as the notifying part 108, the sensor 112, the memory 114, the load 132, and the circuit 134. The power supply 110 may be a primary battery or a secondary battery that can be charged by being connected to an external power supply via a predetermined port (not illustrated) of the aerosol inhalator 100A. Only the power supply 110 may be detachable from the main body 102 or the aerosol inhalator 100A or may be replaceable with a new power supply 110. The power supply 110 may be replaceable with a new power supply 110 by replacing the entire main body 102 with a new main body 102. As an example, the power supply 110 may be formed of a lithium-ion secondary battery, a nickel-hydride secondary battery, a lithium-ion capacitor, or the like.

The sensor 112 may include one or a plurality of sensors that are used to obtain a value of a voltage applied to the entire or a particular portion of the circuit 134, a value of a current flowing in the entire or a particular portion of the circuit 134, a value relating to a resistance value of the load 132, a value relating to a temperature of the load 132, and the like. The sensor 112 may be incorporated into the circuit 134. The functions of the sensor 112 may be incorporated in the controller 106. The sensor 112 may also include one or more of a pressure sensor that detects fluctuation in pressure in the air intake channel 120 and/or the aerosol flow path 121, a flow velocity sensor that detects a flow velocity in the air intake channel 120 and/or the aerosol flow path 121, and a flow rate sensor that detects a flow rate in the air intake channel 120 and/or the aerosol flow path 121. The sensor 112 may also include a weight sensor that detects the weight of a component such as the reservoir 116A. The sensor 112 may be configured to count the number of times the user puffs using the aerosol inhalator 100A. The sensor 112 may be also configured to integrate an energization time to the atomizing part 118A. The sensor 112 may be also configured to detect the height of a liquid surface in the reservoir 116A. The sensor 112 may be also configured to calculate or detect an SOC (State of Charge), a current integrated value, a voltage, and the like of the power supply 110. The SOC may be calculated by a current integration method (coulomb counting method), an SOC-OCV (Open Circuit Voltage) method, or the like. The sensor 112 may be able to detect an operation relative to an operation button or the like operable by the user.

The controller 106 may be an electronic circuit module configured as a microprocessor or a microcomputer. The controller 106 may be configured to control the operation of the aerosol inhalator 100A according to computer executable instructions stored in the memory 114. The memory 114 is a storage medium such as ROM, RAM, flash memory or the like. In the memory 114, in addition to the above-described computer executable instructions, setting data required for controlling the aerosol inhalator 100A and the like may be stored. For example, the memory 114 may store various pieces of data such as a control method of the notifying part 108 (aspects, etc. of light emission, sound production, vibration, etc.), values obtained and/or detected by the sensor 112, and heating history of the atomizing part 118A. The controller 106 reads data from the memory 114 as required to use it in control of the aerosol inhalator 100A and stores data in the memory 114 as required.

Figure 1B:
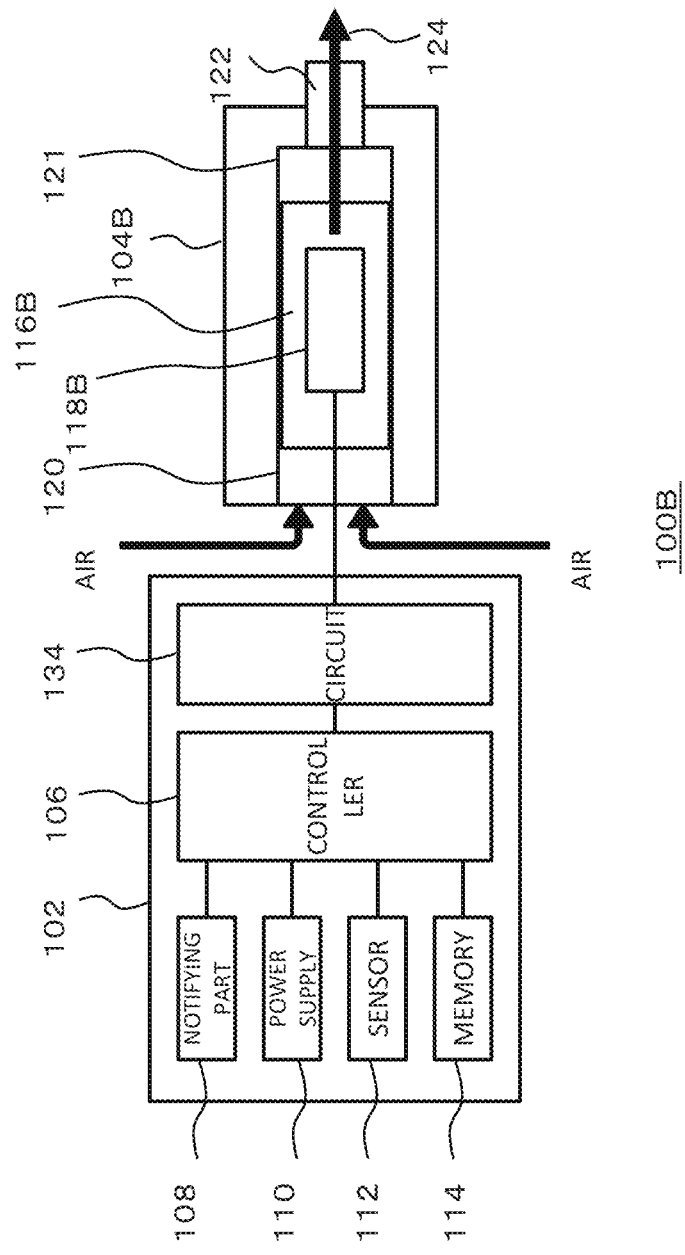
FIG. 1B is a schematic block diagram of a configuration of an aerosol inhalator according to an embodiment of the present disclosure.

FIG. 1B is a schematic block diagram of a configuration of an aerosol inhalator 100B according to an embodiment of the present disclosure.

As illustrated in the figure, the aerosol inhalator 100B has a configuration similar to that of the aerosol inhalator 100A of FIG. 1A. However, a configuration of a second member 104B (hereinafter, referred to as an "aerosol generating article 104B" or a "stick 104B") is different from that of the second member 104A. As an example, the aerosol generating article 104B may include an aerosol base 116B, an atomizing part 118B, an air intake channel 120, an aerosol flow path 121, and a suction port part 122. A part of the components included in the main body 102 may be included in the aerosol generating article 104B. A part of the components included in the aerosol generating article 104B may be included in the main body 102. The aerosol generating article 104B may be configured to be insertable into and removable from the main body 102. Alternatively, all the components included in the main body 102 and the aerosol generating article 104B may be included in the same housing instead of the main body 102 and the aerosol generating article 104B.

The aerosol base 116B may be configured as a solid carrying the aerosol source. As with the reservoir 116A of FIG. 1A, the aerosol source may be liquid, for example, polyalcohol such as glycerin or propylene glycol, or water, or mixing liquid thereof. The aerosol source in the aerosol base 116B may include a cigarette material that emits smoke flavor ingredients by being heated or an extract deriving from the cigarette material. Note that the aerosol base 116B itself may be formed of the cigarette material. When the aerosol inhalator 100B is a medical inhalator such as a nebulizer, the aerosol source may include a drug to be inhaled by a patient. The aerosol base 116B itself may be configured to be replaceable when the aerosol source is consumed. The aerosol source is not limited to the liquid and may be solid.

The atomizing part 118B is configured to atomize the aerosol source and generate aerosol. When an inhaling action or another operation by a user is detected by the sensor 112, the atomizing part 118B generates aerosol. The atomizing part 118B includes a heater (not illustrated) including a load which is electrically connected to the power supply 110. When an inhaling action or another operation by a user is detected, the controller 106 controls power supply to the heater of the atomizing part 118B and heats the aerosol source carried in the aerosol base 116B to thereby atomize the aerosol source. The air intake channel 120 is connected to the atomizing part 118B. The air intake channel 120 communicates with the outside of the aerosol inhalator 100B. The aerosol generated in the atomizing part 118B is mixed with air taken in via the air intake channel 120. Mixed fluid of the aerosol and the air is delivered to the aerosol flow path 121 as indicated by an arrow 124. The aerosol flow path 121 has a tubular structure for transporting the mixed fluid of the aerosol and the air generated in the atomizing part 118B to the suction port part 122.

The controller 106 is configured to control the aerosol inhalators 100A and 100B (hereinafter, also generically referred to as an "aerosol inhalator 100") according to the embodiments of the present disclosure.

Figure 2:
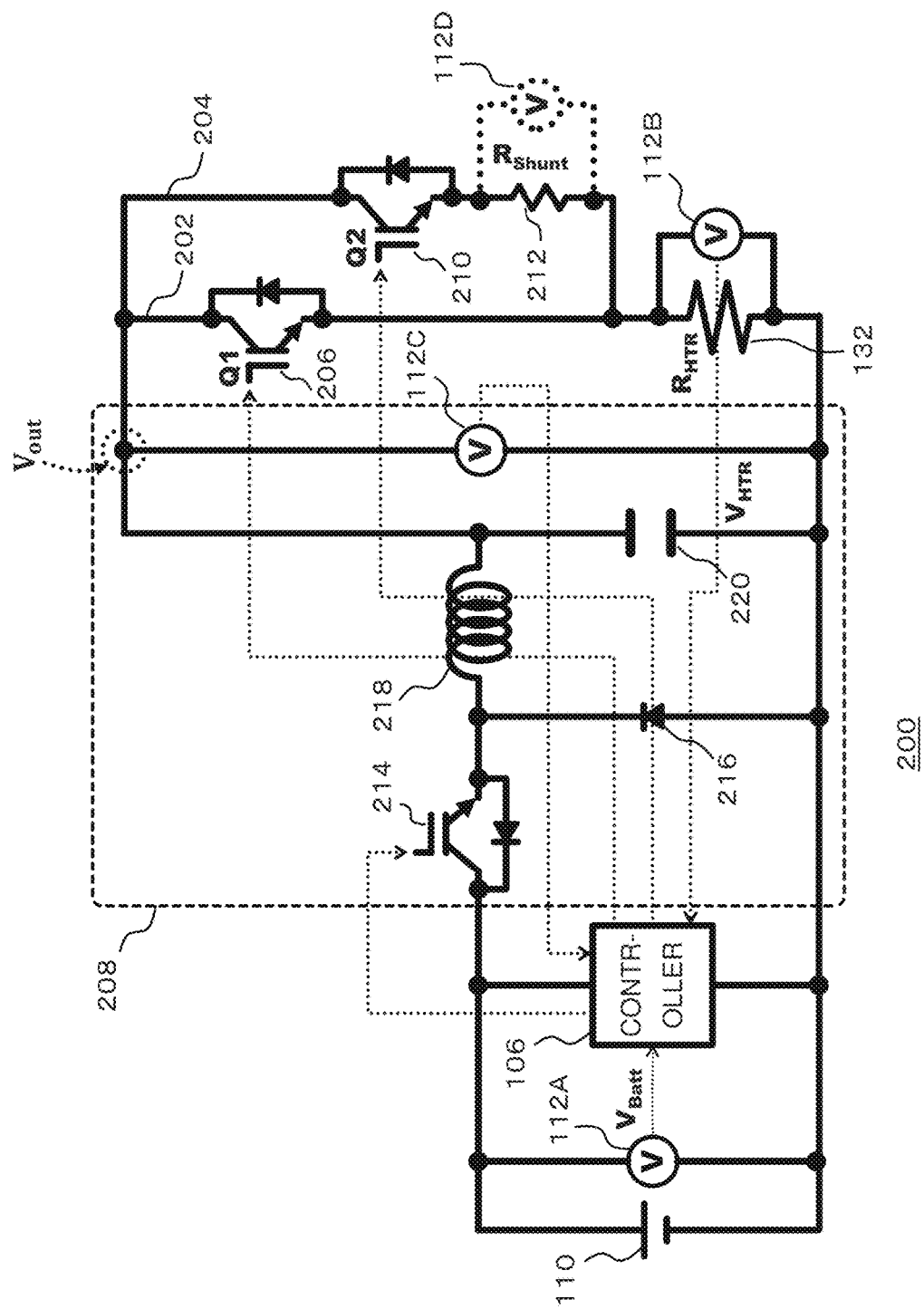
FIG. 2 is a diagram illustrating an exemplary circuit configuration relating to a part of the aerosol inhalator according to an embodiment of the present disclosure.

FIG. 2 is a diagram illustrating an exemplary circuit configuration relating to a part of the aerosol inhalator 100 according to an embodiment of the present disclosure.

A circuit 200 illustrated in FIG. 2 includes the power supply 110, the controller 106, the sensors 112A to 112D (hereinafter, also generically referred to as a "sensor 112"), the load 132 (hereinafter, also referred to as a "heater resistor"), a first circuit 202, a second circuit 204, and a switch Q1 including a first field effect transistor (FET) 206, a converter 208, a switch Q2 including a second field effect transistor 210, and a resistor 212 (hereinafter, also referred to as a "shunt resistor"). The electric resistance value of the load 132 changes depending on temperature. In other words, the load 132 may include a PTC heater. The shunt resistor 212 is connected in series with the load 132, and has the known resistance value. The electric resistance value of the shunt resistor 212 may be almost or completely unchanged relative to the temperature. The shunt resistor 212 has an electric resistance value larger than that of the load 132. Depending on the embodiment, the sensors 112C and 112D may be omitted. It will be apparent to a person skilled in the art that not only FET but also various elements such as IGBT and a contactor can be used as the switches Q1 and Q2. The switches Q1 and Q2 have preferably, but not necessarily, the same characteristics. Accordingly, the FET, the IGBT, the contactor or the like which is used as the switches Q1 and Q2 has preferably, but not necessarily, the same characteristics.

The converter 208 is, for example, a switching converter, and may include an FET 214, a diode 216, an inductor 218, and a capacitor 220. The controller 106 may control the converter 208 so that the converter 208 converts an output voltage of the power supply 110 and the converted output voltage is applied to the entire circuit. Here, the converter 208 is preferably configured to output a constant voltage under control of the controller 106 at least while the switch Q2 is in an on state. The converter 208 may be configured to output a constant voltage under control of the controller 106 even while the switch Q1 is in an on state. Note that the constant voltage output by the converter 208 under control of the controller 106 while the switch Q1 is in an on state and the constant voltage output by the converter 208 under control of the controller 106 while the switch Q2 is in an on state may be the same or may be different. When these constant voltages are different, the constant voltage output by the converter 208 under control of the controller 106 while the switch Q1 is in an on state may be higher or lower than the constant voltage output by the converter 208 under control of the controller 106 while the switch Q2 is in an on state. According to such a configuration, the voltage and the other parameters are stabilized, whereby the accuracy in estimating a residual amount of the aerosol can be improved. Furthermore, the converter 208 may be configured to apply the output voltage of the power supply 110 directly to the first circuit under control of the controller 106 while only the switch Q1 is in an on state. Such an aspect may be achieved by the controller 106 controlling a switching converter in a direct-connection mode so that the switching operation is stopped. Note that the converter 208 is not an essential component and therefore can be omitted.

The circuit 134 illustrated in FIG. 1A and FIG. 1B electrically connects the power supply 110 and the load 132, and may include the first circuit 202 and the second circuit 204. The first circuit 202 and the second circuit 204 are connected in parallel with the power supply 110 and the load 132. The first circuit 202 may include the switch Q1. The second circuit 204 may include the switch Q2 and the resistor 212 (and, optionally, the sensor 112D). The first circuit 202 has a resistance value smaller than that of the second circuit 204. In this example, the sensors 112B and 112D are the voltage sensors, and are configured to detect a potential differential (which may be hereinafter referred to as a "voltage" or a "voltage value") between two terminals of the load 132 and a potential differential (which may be hereinafter referred to as a "voltage" or a "voltage value") between two terminals of the resistor 212, respectively. However, the configuration of the sensor 112 is not limited thereto. For example, the sensor 112 may be a current sensor, and may detect a value of a current flowing through the load 132 and/or the resistor 212.

As indicated by dotted arrows in FIG. 2, the controller 106 can control the switch Q1, the switch Q2 and the like, and can obtain values detected by the sensor 112. The controller 106 may be configured to cause the first circuit 202 to function by switching the switch Q1 from an off state to an on state, and may be configured to cause the second circuit 204 to function by switching the switch Q2 from an off state to an on state. The controller 106 may be configured to cause the first circuit 202 and the second circuit 204 to alternately function by alternately switching the switches Q1 and Q2.

The first circuit 202 is mainly used to atomize the aerosol source. When the switch Q1 is switched to the on state and the first circuit 202 functions, electric power is supplied to the heater (i.e., the load 132 in the heater), and the load 132 is heated. The aerosol source (in the case of the aerosol inhalator 100B of FIG. 1B, the aerosol source carried by the aerosol base 116B) retained by the retainer 130 in the atomizing part 118A is atomized by heating of the load 132, and the aerosol is generated.

The second circuit 204 is used to obtain a value of a voltage applied to the load 132, a value of a current flowing in the load 132, a value of a voltage applied to the resistor 212, a value of a current flowing in the resistor 212, and the like.

The obtained voltage or current value can be used to obtain a resistance value of the load 132. Hereinafter, a case where the switch Q1 is in the off state so that the first circuit 202 does not function, and the switch Q2 is in the on state so that the second circuit 204 functions is considered. In this case, since the current flows through the switch Q2, the shunt resistor 212, and the load 132, the resistance value $R_{HTR}$ ($T_{HTR}$) of the load 132 when the temperature of the load 132 is $T_{HTR}$ can be obtained by calculation using, for example, the following expression.

[Formula 1]

$$R_{HTR}(T_{HTR}) = \frac{V_{HTR}}{V_{out} - V_{HTR}} \cdot R_{shunt} \qquad (1)$$

$$= \frac{V_{out} - V_{shunt}}{V_{shunt}} \cdot R_{shunt} \qquad (2)$$

$$= \frac{V_{out}}{I_{HTR}} - R_{shunt} \qquad (3)$$

$$= \frac{V_{HTR}}{I_{HTR}} \qquad (4)$$

Where $V_{out}$ represents a voltage which may be detected by the sensor 112C or a predetermined target voltage which is output by the converter 208, that is, a voltage applied to the entire of the first circuit 202 and the second circuit 204. Note that when the converter 208 is not used, the voltage $V_{out}$ may be a voltage $V_{Batt}$ which may be detected by the sensor 112A. $V_{HTR}$ represents a voltage applied to the load 132 which may be detected by the sensor 112B, and $V_{shunt}$ represents a voltage applied to the shunt resistor 212 which may be detected by the sensor 112D. $I_{HTR}$ represents a current flowing in the load 132 (in this case, the same as a current flowing in the shunt resistor 212) which may be detected by a sensor (e.g., a hall element) (not illustrated). $R_{shunt}$ represents a known resistance value of a predeterminable shunt resistor 212.

Note that the resistance value of the load 132 can be obtained at least using the expression (4) regardless of whether the switch Q2 functions, even when the switch Q1 is in the on state. This means that in the embodiments of the present disclosure, the output value of the sensor 112 obtained when the switch Q1 is in the on state can be used and a circuit in which the second circuit 204 does not exist can be used. Note that the above-described technique is only illustrative, and the resistance value of the load 132 may be obtained by any technique.

The obtained resistance value of the load 132 can be used to obtain the temperature of the load 132. More specifically, when the load 132 has positive or negative temperature coefficient characteristics (the positive temperature coefficient characteristics may be referred to as "PTC characteristics") in which the resistance value changes depending on the temperature, the temperature $T_{HTR}$ of the load 132 can be estimated based on the relationship between the pre-known resistance value and temperature of the load 132 and the resistance value $R_{HTR}$ ($T_{HTR}$) of the load 132 obtained as described above. It will be appreciated that the temperature of the load 132 can be directly obtained or calculated using the obtained voltage or current value without obtaining or calculating the resistance value of the load 132. In addition, it will be appreciated that the obtained voltage or current value itself may be regarded as corresponding to the temperature of the load 132.

Note that the circuit included in the aerosol inhalator 100 may include a temperature sensor which directly output a value corresponding to the temperature of the load 132, instead of at least one of the above-described sensors or in addition to the above-described sensors.

2. Principle of Determining Occurrence of Depletion or Insufficiency of Aerosol Source The aerosol inhalator 100 according to an embodiment of the present disclosure determines the occurrence of depletion or insufficiency of the aerosol source. Hereinafter, a principle of determining the occurrence of depletion or insufficiency of the aerosol source according to an embodiment of the present disclosure will be described.

Note that in the present disclosure, the residual amount of the aerosol source being "depleted" refers to a state in which the residual amount of the aerosol source is zero or nearly zero.

In addition, in the present disclosure, the residual amount of the aerosol source being "insufficient" refers to a state in which the residual amount of the aerosol source is insufficient but is not depleted. Alternatively, the residual amount of the aerosol source being "insufficient" may refer to a state in which the residual amount of the aerosol source is sufficient for the instantaneous aerosol generation, but is insufficient for the continuous aerosol generation. Alternatively, the residual amount of the aerosol source being "insufficient" may refer to a state in which the residual amount of the aerosol source is insufficient for generating the aerosol having sufficient smoke flavor.

Furthermore, when the aerosol source in the aerosol base 116B or the retainer 130 is in a saturation state, the temperature of the load 132 reaches a steady state at a boiling point of the aerosol source or a temperature when the aerosol generation occurs by evaporation of the aerosol source (hereinafter, referred to as a "boiling point or the like"). This event will be appreciated from that the heat generated in the load 132 by electric power supplied from the power supply 110 is used not to increase the temperature of the aerosol source but to evaporate the aerosol source or generate the aerosol at these temperatures. Here, even when the aerosol source in the aerosol base 116B or the retainer 130 is not in a saturation state but the residual amount of the aerosol source is a certain amount or more, the temperature of the load 132 reaches a steady state at a boiling point or the like. In the present disclosure, the residual amount of the aerosol source in the aerosol base 116B or the retainer 130 being "sufficient" refers to a state such that the residual amount of the aerosol source in the aerosol base 116B or the retainer 130 is the certain amount or more, or the residual amount of the aerosol source in the aerosol base 116B or the retainer 130 reaches a state (including the saturation state) in which the temperature of the load 132 reaches the steady state at the boiling point or the like. Note that in the latter case, a specific residual amount of the aerosol source in the aerosol base 116B or the retainer 130 need not be specified. In addition, the boiling point of the aerosol source and the temperature when the aerosol generation occurs are coincident with each other where the aerosol source is liquid made of a single composition. On the other hand, when the aerosol source is mixing liquid, a theoretical temperature of the mixing liquid obtained by Raoult's law may be regarded as the temperature when the aerosol generation occurs or the temperature when the aerosol is generated by the boiling of the aerosol source may be obtained by an experiment.

Still further, when the residual amount of the aerosol source in the reservoir 116A is less than a certain amount, in principle, the aerosol source is not supplied from the reservoir 116A to the retainer 130 (in some cases, very small amount of the aerosol source may be supplied, or more or less aerosol source may be supplied by inclining or shaking the aerosol inhalator 100). In the present disclosure, the residual amount of the aerosol source in the reservoir 116A being "sufficient" refers to a state such that the residual amount of the aerosol source in the reservoir 116A is a certain amount or more, or the aerosol source in the retainer 130 is in the saturation state or the above-described certain amount or more of the remaining aerosol source in the retainer 130 can be supplied. Note that in the latter case, since it can be estimated or determined that the residual amount of the aerosol source in the reservoir 116A is sufficient when the temperature of the load 132 is in the steady state at the boiling point or the like, the specific residual amount of the aerosol source in the reservoir 116A need not be specified. In this case, when the residual amount of the aerosol source in the retainer 130 is not sufficient (that is, is insufficient or is depleted), it can be estimated or determined that the residual amount of the aerosol source in the reservoir 116A is not sufficient (that is, is insufficient or is depleted).

Hereinafter, the reservoir 116A, the aerosol base 116B, and the retainer 130 are generically referred to as "retainer and the like."

2-1. Basic Principle

Figure 3:
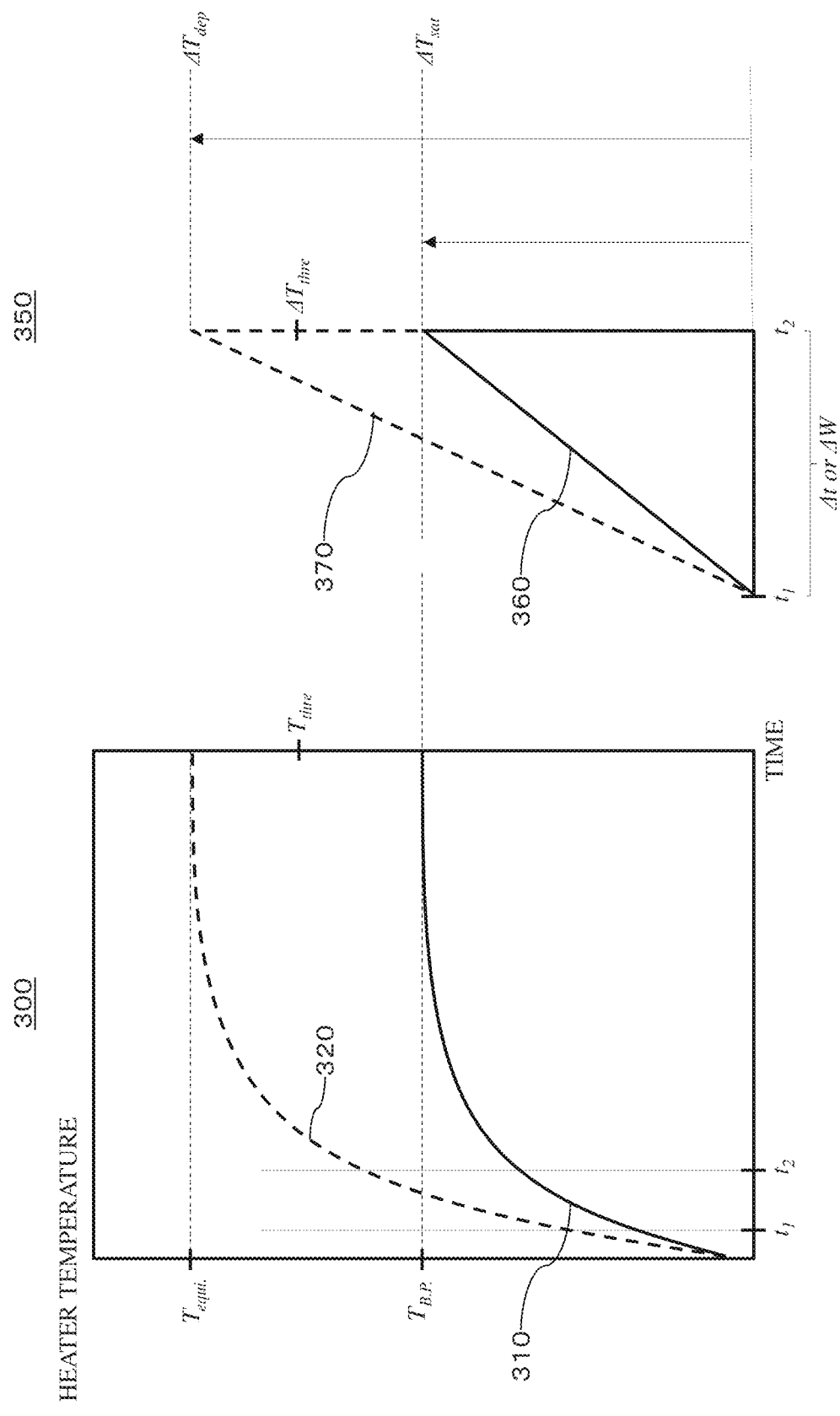
FIG. 3 is a graph schematically showing a temperature profile of a load of the aerosol inhalator and illustrates a temperature change of the load per a predetermined time period or a predetermined amount of electric power.

FIG. 3 is a graph 300 schematically showing a time-series change (hereinafter, also referred to as a "temperature profile") in a temperature of the load 132 (hereinafter, also referred to as a "heater temperature") from the start of power supply to the load 132 and illustrates a temperature change 350 of the load 132 per a predetermined time period or per a predetermined electric power supplied to the load 132.

A reference numeral 310 in the graph 300 represents a schematic temperature profile of the load 132 when the residual amount of the aerosol source in the retainer and the like is sufficient, and a reference symbol "$T_{B.P.}$" denotes a boiling point or the like of the aerosol source. The temperature profile 310 shows that when the residual amount of the aerosol source in the retainer and the like is sufficient, the temperature of the load 132 reaches the steady state at $T_{B.P.}$ which is the boiling point or the like of the aerosol source or in the vicinity of $T_{B.P.}$ which is the boiling point or the like of the aerosol source, after the temperature increase of the load 132 is started. This is presumably because the temperature rise of the load 132 by the electric power supply does not occur when almost all of electric power supplied to the load 132 is finally consumed for atomizing the aerosol source in the retainer and the like.

Note that the outline of the temperature profile 310 is merely schematically represented, and, in practice, localized increases and decreases in the temperature of the load 132 are included in the temperature profile 310, and any transient changes (not shown) may occur. These transient changes may be caused by temperature deviation which may occur temporarily in the load 132, the temperature itself of the load 132, chattering which occurs in the sensor and the like for detecting the electrical parameter corresponding to the temperature of the load 132, and the like. This is applicable to the "schematic temperature profile" described below.

A reference numeral 320 in the graph 300 represents a schematic temperature profile of the load 132 when the residual amount of the aerosol source in the retainer and the like is not sufficient. The temperature profile 320 shows that when the residual amount of the aerosol source in the retainer and the like is not sufficient, the temperature of the load 132 may reach the steady state at an equilibrium temperature $T_{equi.}$ which is higher than the boiling point $T_{B.P.}$ or the like of the aerosol source, after the temperature increase of the load 132 is started. This is presumably because the increase in temperature by electric power applied to the load 132, the decrease in temperature due to heat transfer to substances near the load 132 (including gas around the load 132, a part of the structure of the aerosol inhalator 100), and in some cases, the decrease in temperature due to vaporization heat of a small amount of the aerosol source in the aerosol base 116B or the retainer 130 finally come to an equilibrium. Note that when the residual amount of the aerosol source in the retainer and the like is not sufficient, it has been observed that the temperature of the load 132 may reach the steady state at different temperatures according to the residual amount of the aerosol source in the aerosol base 116B or the retainer 130 and the residual amount of the aerosol source in the reservoir 116A (may influence the supply rate of the aerosol source to the retainer 130), a distribution of the aerosol source in the aerosol base 116B or the retainer 130, or the like. The equilibrium temperature $T_{equi.}$ is one of such temperatures, preferably, is one of such temperatures which is not the highest temperature (which is a temperature when the residual amount of the aerosol source in the aerosol base 116B or the retainer 130 is completely zero). Note that when the residual amount of the aerosol source in the retainer and the like is not sufficient, it has been observed that the temperature of the load 132 may not reach the steady state, but even in such a case, it remains unchanged that the temperature of the load 132 reaches the temperature which is higher than the boiling point $T_{B.P.}$ or the like of the aerosol source.

Based on the schematic temperature profile of the load 132 when the aerosol source in the retainer and the like is sufficient and is not sufficient as described above, it can be basically determined that the residual amount of the aerosol source in the retainer and the like is sufficient or is not sufficient (that is, the residual amount of the aerosol source in the retainer and the like is insufficient or is depleted) by determining whether the temperature of the load 132 has exceeded a predetermined temperature threshold $T_{thre}$ which is equal to or higher than the boiling point Tap. or the like of the aerosol source and equal to or lower than the equilibrium temperature $T_{equi.}$.

The temperature change 350 of the load 132 per a predetermined time period shows a temperature change of the load 132 per a predetermined time period Δt between a time $t_1$ and a time $t_2$ in the graph 300. Reference numerals 360 and 370 correspond to the temperature change when the residual amount of the aerosol source in the retainer and the like is sufficient and the temperature change when the residual amount of the aerosol source in the retainer and the like is not sufficient, respectively. The temperature change 360 shows that the temperature of the load 132 is increased by $\Delta T_{sat}$ per a predetermined time period Δt when the residual amount of the aerosol source in the retainer and the like is sufficient. The temperature change 370 shows that the temperature of the load 132 is increased by $\Delta T_{dep}$ which is larger than $\Delta T_{sat}$ per a predetermined time period Δt, when the residual amount of the aerosol source in the retainer and the like is not sufficient. Note that $\Delta T_{sat}$ and $\Delta T_{dep}$ change depending on a length of the predetermined time period Δt, or change when $t_1$ (and $t_2$) is changed even when the length is fixed. Hereinafter, $\Delta T_{sat}$ and $\Delta T_{dep}$ are the maximum temperature changes which can be obtained when $t_1$ (and $t_2$) is changed in a predetermined time period $\Delta t$ having a certain length.

Based on the temperature change per a predetermined time period of the load 132 when the aerosol source in the retainer and the like is sufficient and is not sufficient as described above, it can be basically determined that the residual amount of the aerosol source in the retainer and the like is sufficient or is not sufficient (that is, the residual amount of the aerosol source in the retainer and the like is insufficient or is depleted) by determining whether the temperature change per a predetermined time period $\Delta t$ has exceeded a predetermined temperature change threshold $\Delta T_{thre}$ which is equal to or larger than $\Delta T_{sat}$ and equal to or smaller than $\Delta T_{dep}$.

Note that it will be appreciated that it can be determined that the residual amount of the aerosol source in the retainer and the like is sufficient or is not sufficient, using the temperature change of the load 132 per a predetermined electric power $\Delta W$ supplied to the load 132 instead of the temperature change per a predetermined time period $\Delta t$.

As described above, the basic principle of determining occurrence of depletion or insufficiency of aerosol source according to an embodiment of the present disclosure has been described. However, the thus set threshold may cause a problem for practical use. This is because it has been observed that the temperature of the load 132 in the steady state and the temperature change of the load 132 per a predetermined time period are changed by inhalation of the aerosol inhalator 100 when the residual amount of the aerosol source in the retainer and the like is sufficient. This point will be described below.

2-2. Behavior of Heater Temperature and Improved Principle

FIG. 4A illustrates an exemplary and schematic structure in a vicinity of the load 132 of the aerosol inhalator 100. A reference numerals 400A to 400C illustrate different exemplary structures, respectively. Reference numeral 410 denotes a component corresponding to the retainer and the like, and a reference numeral 420 denotes a component at least a part of which corresponds to the load 132. A reference numeral 430 represents a flow direction of the air stream caused by inhalation of the aerosol inhalator 100. Note that in the structure 400A, the load 132 is disposed in a position not to be in contact with the above-described air stream. More specifically, in the structure 400A, the load 132 is disposed in a partially recessed portion of the retainer 410, whereby the load 132 is not in contact with the above-described air stream. Note that the load 132 is disposed away from the above-described air stream channel, whereby the above-described air stream does not contact the load 132.

FIG. 4B shows graphs 450A to 450C showing exemplary temperature profiles which are obtained by experiments using the aerosol inhalators 100 having the structures 400A to 400C, respectively. A reference numeral 460 represents an average of a plurality of temperature profiles of the load 132, which are obtained when the residual amount of the aerosol source in the retainer and the like is sufficient and the aerosol inhalator 100 is not inhaled. A reference numeral 470 represents an average of a plurality of temperature profiles of the load 132, which are obtained when the residual amount of the aerosol source in the retainer and the like is sufficient and the aerosol inhalator 100 is inhaled so that the flow rate of 55 cc ($cm^3$) per 3 seconds can be produced. A reference numeral 480 represents an average of a plurality of temperature profiles of the load 132, which are obtained when the residual amount of the aerosol source in the retainer and the like is sufficient and the aerosol inhalator 100 is inhaled so that the flow rate of 110 cc ($cm^3$) per 3 seconds can be produced. Here, note that the inhalation strength according to the temperature profile 480 is larger than the inhalation strength according to the temperature profile 470.

FIG. 5 shows a graph 500 including a schematic temperature profile of the load 132 in which an exemplary temperature profile in the graph 450A of FIG. 4B is simplified for easy understanding, and illustrates a temperature change 550 of the load 132 per a predetermined time period.

A reference numeral 510A in the graph 500 represents a schematic temperature profile of the load 132 when the residual amount of the aerosol source in the retainer and the like is sufficient and the aerosol inhalator 100 is not inhaled, and corresponds to the temperature profile 310 in FIG. 3. On the other hand, a reference numeral 510B represents a schematic temperature profile of the load 132 when the residual amount of the aerosol source in the retainer and the like is sufficient and the aerosol inhalator 100 is inhaled with a first strength. The temperature profile 510B shows that when the residual amount of the aerosol source in the retainer and the like is sufficient and the aerosol inhalator 100 is inhaled with the first strength (hereinafter, the flow velocity is represented as "$v_1$"), the temperature of the load 132 reaches the steady state at a temperature $T'_{satmax}(v_1)$ which is higher than the boiling point $T_{B.P.}$ or the like of the aerosol after the temperature increase of the load 132 is started. A reference numeral 510C represents a schematic temperature profile of the load 132 when the residual amount of the aerosol source in the retainer and the like is sufficient and the aerosol inhalator 100 is inhaled with a second strength which is larger than the first strength. The temperature profile 510C shows that when the residual amount of the aerosol source in the retainer and the like is sufficient and the aerosol inhalator 100 is inhaled with the second strength (hereinafter, the flow velocity is represented as "$v_2$"), the temperature of the load 132 reaches the steady state at a temperature $T'_{satmax}(v_2)$ which is higher than the temperature $T'_{satmax}(v_1)$ after the temperature increase of the load 132 is started.

That is, the temperature profiles 510A to 510C show that there exists a system that depending on the structure of the load 132, the temperature of the load 132 at the steady state is increased as the inhalation strength relative to the aerosol inhalator 100 is increased, when the residual amount of the aerosol source in the retainer and the like is sufficient. In such a system, using the temperature threshold set without taking into consideration the inhaling on the aerosol inhalator 100 leads to a problem in that although the residual amount of the aerosol source in the retainer and the like is sufficient, it may be falsely determined that the residual amount of the aerosol source in the retainer and the like is not sufficient. For example, using $T_{thre}$ as a temperature threshold in the graph 500 leads to a problem in that although the residual amount of the aerosol source in the retainer and the like is sufficient, it is falsely determined that the residual amount of the aerosol source in the retainer and the like is not sufficient when the aerosol inhalator 100 is inhaled with the first strength $v_1$ or higher.

This problem can be addressed by comparing the temperature of the load 132 with a predetermined temperature threshold $T'_{thre}(v)$ which is equal to or higher than the temperature $T'_{satmax}(v)$ of the load 132 at the steady state according to the inhalation strength (hereinabove and hereinafter, the flow velocity is represented as "v") and equal to or lower than the equilibrium temperature $T_{equi.}$. As a specific example, only when the temperature of the load 132 exceeds the temperature threshold $T'_{thre}(v)$, it is necessary to determine that the residual amount of the aerosol source in the retainer and the like is not sufficient.

In another aspect, when it is assumed that $T_{thre}$ in the graph 500 is regarded as the temperature threshold set without taking into consideration the inhaling on the aerosol inhalator 100, and the magnitude of a difference between the boiling point $T_{B.P.}$ or the like of the aerosol source and the temperature $T'_{satmax}(v)$ is represented as $\varepsilon_1(v)$, if the temperature threshold $T'_{thre}(v)$ to be compared is set to $T_{thre}+\varepsilon_1(v)$, the above-described problem does not occur. For example, if the temperature thresholds $T'_{thre}(v_1)$ and $T'_{thre}(v_2)$ to be compared are dynamically set to $T_{thre}+\varepsilon_1(v_1)$ when the aerosol inhalator 100 is inhaled with the first strength $v_1$ and $T_{thre}+\varepsilon_1(v_2)$ when the aerosol inhalator 100 is inhaled with the second strength $v_2$, respectively, the false determination of the residual amount of the aerosol source in the retainer and the like can be prevented.

The inventors have discovered that in such a system, the equilibrium temperature $T_{equi.}$ reached by the load 132 may be increased as the inhalation strength relative to the aerosol inhalator 100 is increased, even when the residual amount of the aerosol source in the retainer and the like is not sufficient. Reference numerals 520A and 520B in the graph 500 represent exemplary and schematic temperature profiles of the load 132, respectively, in which the reference numeral 520A represents the temperature profile when the residual amount of the aerosol source in the retainer and the like is not sufficient and the aerosol inhalator 100 is not inhaled, and the reference numeral 520B represents the temperature profile when the residual amount of the aerosol source in the retainer and the like is not sufficient and the aerosol inhalator 100 is inhaled with a certain strength. Accordingly, hereinafter, when it is assumed that the equilibrium temperature reached by the load 132 according to the inhalation strength is represented as $T'_{depmax}(v)$ when the residual amount of the aerosol source in the retainer and the like is not sufficient, the temperature threshold to be compared may be $T'_{satmax}(v)$ or higher and $T'_{depmax}(v)$ or lower.

Note that values of $T'_{satmax}(v)$, $\varepsilon_1(v)$ and $T'_{depmax}(v)$ or their functions which are set according to various inhalation strengths can be obtained in advance by experiments. Furthermore, $T'_{satmax}(v)$, $\varepsilon_1(v)$ and $T'_{depmax}(v)$ may be not flow velocities v but functions of the corresponding flow rate or pressure. Here, these values of the flow velocity, the flow rate, and the pressure are values associated with the inhalation strengths.

The temperature change 550 of the load 132 per a predetermined time period shows a temperature change of the load 132 per a time period $\Delta t$ between a time $t_1$ and a time $t_2$ in the graph 500. A reference numeral 560A represents a temperature change of the load 132 per a predetermined time period $\Delta t$ when the residual amount of the aerosol source in the retainer and the like is sufficient and the aerosol inhalator 100 is not inhaled, and corresponds to the temperature change 360 in FIG. 3. On the other hand, a reference numeral 560B represents a temperature change of the load 132 per a predetermined time period $\Delta t$ when the residual amount of the aerosol source in the retainer and the like is sufficient and the aerosol inhalator 100 is inhaled with a first strength $v_1$. The temperature change 560B shows that when the residual amount of the aerosol source in the retainer and the like is sufficient and the aerosol inhalator 100 is inhaled with the first strength $v_1$, the temperature of the load 132 per a predetermined time period $\Delta t$ is increased by $\Delta T'_{sat}(v_1)$ which is larger than $\Delta T_{sat}$. A reference numeral 560C represents a temperature change of the load 132 per a predetermined time period $\Delta t$ when the residual amount of the aerosol source in the retainer and the like is sufficient and the aerosol inhalator 100 is inhaled with a second strength $v_2$. The temperature change 560C shows that when the residual amount of the aerosol source in the retainer and the like is sufficient and the aerosol inhalator 100 is inhaled with the second strength $v_2$, the temperature of the load 132 per a predetermined time period $\Delta t$ is increased by $\Delta T'_{sat}(v_2)$ which is larger than $\Delta T'_{sat}(v_1)$.

That is, the temperature changes 560A to 560C show that there exists a system that depending on the structure of the load 132, the temperature rise width of the load 132 per a predetermined time period is increased as the inhalation strength relative to the aerosol inhalator 100 is increased, when the residual amount of the aerosol source in the retainer and the like is sufficient. In such a system, using the temperature change threshold set without taking into consideration the inhaling on the aerosol inhalator 100 leads to a problem in that although the residual amount of the aerosol source in the retainer and the like is sufficient, it may be falsely determined that the residual amount of the aerosol source in the retainer and the like is not sufficient. For example, using $T_{thre}$ in the temperature change 550 as a temperature change threshold leads to a problem in that although the residual amount of the aerosol source in the retainer and the like is sufficient, it is falsely determined that the residual amount of the aerosol source in the retainer and the like is not sufficient when the aerosol inhalator 100 is inhaled with the first strength $v_1$ or higher.

When it is assumed that the maximum temperature change which can be obtained when $t_1$ (and $t_2$) is changed in a predetermined time period $\Delta t$ having a certain length is regarded as $\Delta T'_{sat}(v)$ when the residual amount of the aerosol source in the retainer and the like is sufficient and the flow velocity is v, this problem can be addressed by comparing the temperature change of the load 132 per a predetermined time period $\Delta t$ with a predetermined temperature change threshold $\Delta T'_{thre}(v)$ which is equal to or larger than $\Delta T'_{sat}(v)$ as a temperature change according to the inhalation strength and equal to or smaller than $\Delta T_{dep}$ as a temperature change according to the inhalation strength. As a specific example, only when the temperature change of the load 132 per a predetermined time period $\Delta t$ exceeds the temperature change threshold $\Delta T'_{thre}(v)$, it is necessary to determine that the residual amount of the aerosol source in the retainer and the like is not sufficient.

In another aspect, when it is assumed that $\Delta T_{thre}$ in the temperature change 550 is regarded as the temperature change threshold set without taking into consideration the inhaling on the aerosol inhalator 100, and the magnitude of a difference between $\Delta T_{sat}$ and $\Delta T'_{sat}(v)$ is represented as $\Delta \varepsilon_1(v)$, if the temperature change threshold $\Delta T'_{thre}(v)$ to be compared is set to $\Delta T_{thre}+\Delta \varepsilon_1(v)$, the above-described problem does not occur. For example, if the temperature change thresholds $\Delta T'_{thre}(v_1)$ and $\Delta T'_{thre}(v_2)$ to be compared are dynamically set to $\Delta T_{thre}+\Delta \varepsilon_1(v_1)$ when the aerosol inhalator 100 is inhaled with the first strength $v_1$ and $\Delta T_{thre}+\Delta \varepsilon_1(v_2)$ when the aerosol inhalator 100 is inhaled with the second strength $v_2$, respectively, the false determination of the residual amount of the aerosol source in the retainer and the like can be prevented.

The inventors have discovered that in such a system, the temperature change of the load 132 per a predetermined time period $\Delta t$ may be increased as the inhalation strength relative to the aerosol inhalator 100 is increased, even when the residual amount of the aerosol source in the retainer and the like is not sufficient. Reference numerals 570A and 570B in the temperature change 550 represent exemplary temperature changes of the load 132, respectively, in which the reference numeral 570A represents the temperature change when the residual amount of the aerosol source in the retainer and the like is not sufficient and the aerosol inhalator 100 is not inhaled, and the reference numeral 570B represents the temperature change when the residual amount of the aerosol source in the retainer and the like is not sufficient and the aerosol inhalator 100 is inhaled with a certain strength. Accordingly, hereinafter, when it is assumed that the maximum temperature change which can be obtained when $t_1$ (and $t_2$) is changed in a predetermined time period $\Delta t$ having a certain length is regarded as $\Delta T'_{dep}(v)$ when the residual amount of the aerosol source in the retainer and the like is not sufficient and the flow velocity is v, the temperature change threshold $\Delta T'_{thre}(v)$ to be compared may be $\Delta T'_{sat}(v)$ or more and $\Delta T'_{dep}(v)$ or less.

Note that values of $\Delta T'_{sat}(v)$, $\Delta \varepsilon_1(v)$ and $\Delta T'_{dep}(v)$ or their functions which are set according to various inhalation strengths can be obtained in advance by experiments. Furthermore, $\Delta T'_{sat}(v)$, $\Delta \varepsilon_1(v)$ and $\Delta T'_{dep}(v)$ may be not flow velocities v but functions of the corresponding flow rate or pressure.

Figure 4A:
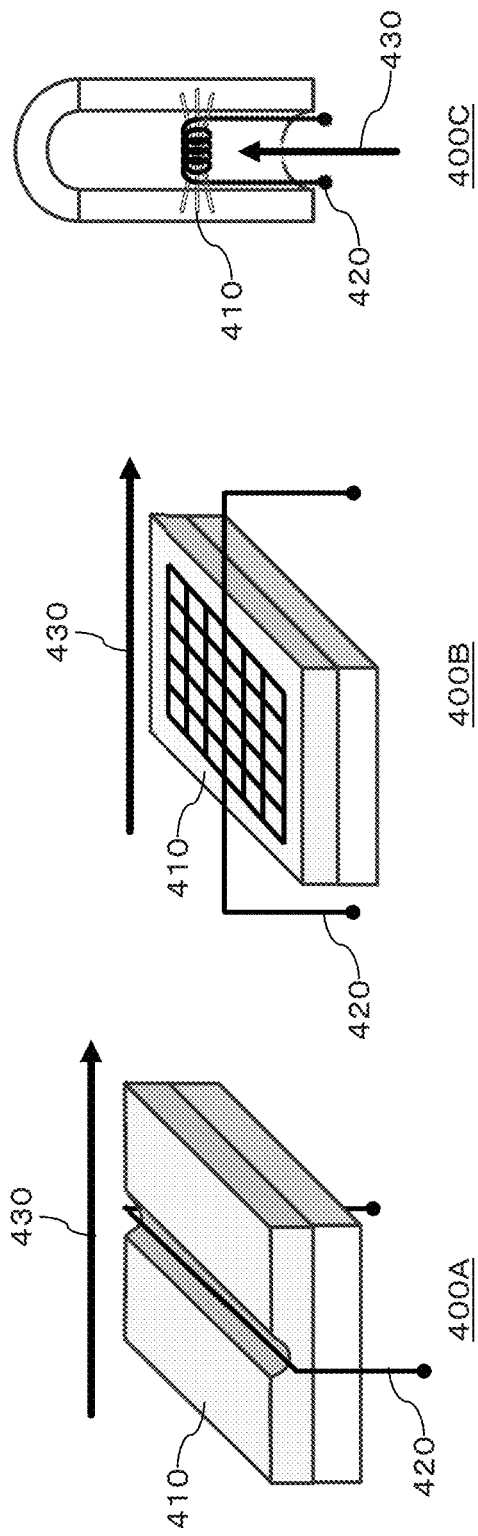
FIG. 4A illustrates an exemplary and schematic structure in a vicinity of the load of the aerosol inhalator.
Figure 6:
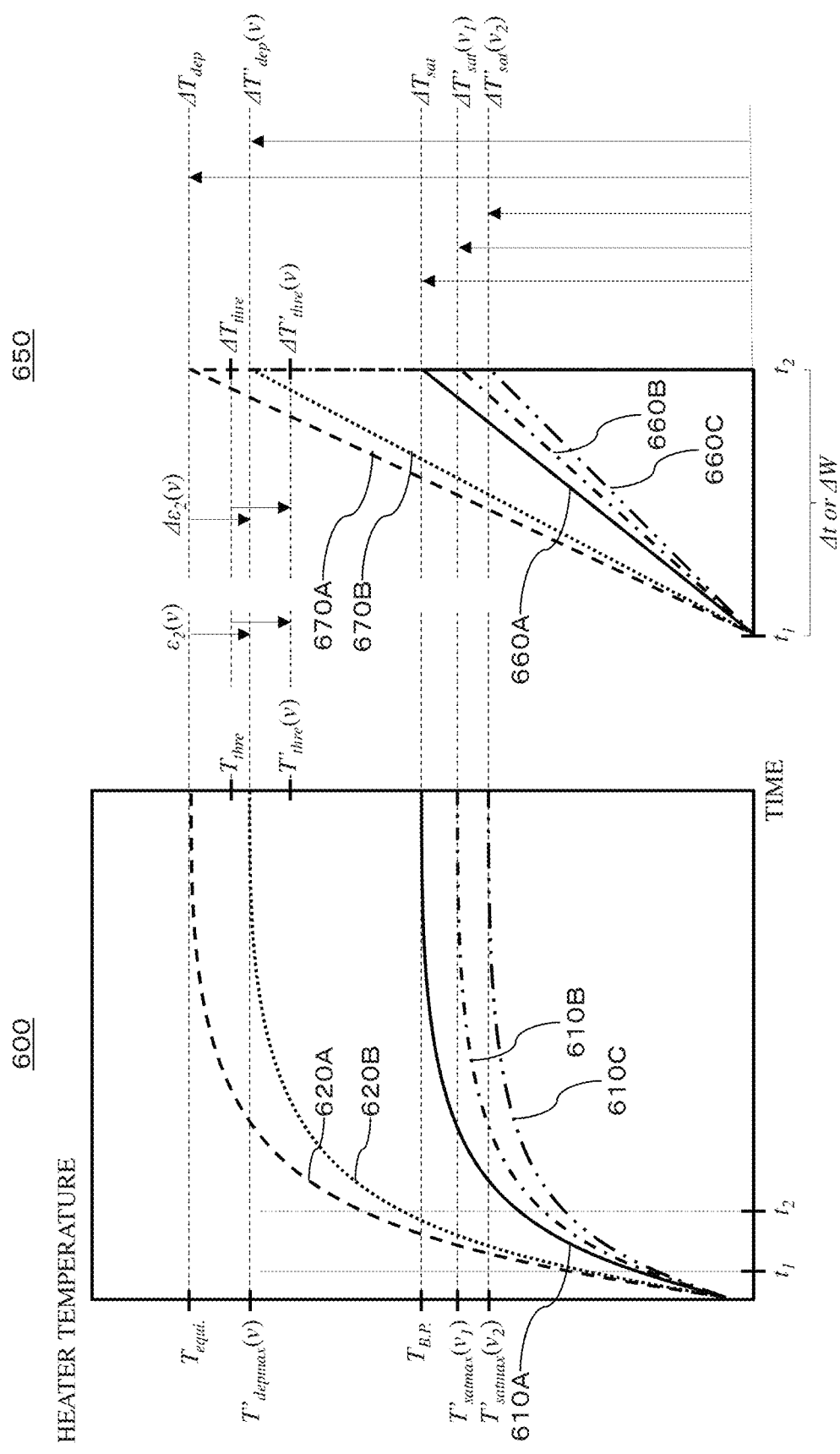
FIG. 6 is a graph schematically showing a temperature profile of a load of an aerosol inhalator having a certain structure, taking inhalation into consideration, and illustrates a temperature change of a load per a predetermined time period or a predetermined amount of electric power.

FIG. 6 shows a graph 600 including a schematic temperature profile of the load 132 in which an exemplary temperature profile in the graph 450B of FIG. 4B is simplified for easy understanding, and illustrates a temperature change 650 of the load 132 per a predetermined time period.

A reference numeral 610A in the graph 600 represents a schematic temperature profile of the load 132 when the residual amount of the aerosol source in the retainer and the like is sufficient and the aerosol inhalator 100 is not inhaled, and corresponds to the temperature profile 310 in FIG. 3. On the other hand, a reference numeral 610B represents a schematic temperature profile of the load 132 when the residual amount of the aerosol source in the retainer and the like is sufficient and the aerosol inhalator 100 is inhaled with a first strength $v_1$. The temperature profile 610B shows that when the residual amount of the aerosol source in the retainer and the like is sufficient and the aerosol inhalator 100 is inhaled with the first strength $v_1$, the temperature of the load 132 reaches the steady state at a temperature $T'_{satmax}(v_1)$ which is lower than the boiling point $T_{B.P.}$ or the like of the aerosol after the temperature increase of the load 132 is started. A reference numeral 610C represents a schematic temperature profile of the load 132 when the residual amount of the aerosol source in the retainer and the like is sufficient and the aerosol inhalator 100 is inhaled with a second strength $v_2$. The temperature profile 610C shows that when the residual amount of the aerosol source in the retainer and the like is sufficient and the aerosol inhalator 100 is inhaled with the second strength $v_2$, the temperature of the load 132 reaches the steady state at a temperature $T'_{satmax}(v_2)$ which is lower than the temperature $T'_{satmax}(v_1)$ after the temperature increase of the load 132 is started.

That is, the temperature profiles 610A to 610C show that there exists a system that depending on the structure of the load 132, the temperature of the load 132 at the steady state is decreased as the inhalation strength relative to the aerosol inhalator 100 is increased, when the residual amount of the aerosol source in the retainer and the like is sufficient. In such a system, even when the residual amount of the aerosol source in the retainer and the like is not sufficient, the equilibrium temperature $T_{equi.}$ reached by the load 132 may be decreased as the inhalation strength relative to the aerosol inhalator 100 is increased. Accordingly, in such a system, using the temperature threshold set without taking into consideration the inhaling on the aerosol inhalator 100 leads to a problem in that although the residual amount of the aerosol source in the retainer and the like is not sufficient, it may be falsely determined that the residual amount of the aerosol source in the retainer and the like is sufficient. Reference numerals 620A and 620B in the graph 600 represent exemplary and schematic temperature profiles of the load 132, respectively, in which the reference numeral 620A represents the temperature profile when the residual amount of the aerosol source in the retainer and the like is not sufficient and the aerosol inhalator 100 is not inhaled, and the reference numeral 620B represents the temperature profile when the residual amount of the aerosol source in the retainer and the like is not sufficient and the aerosol inhalator 100 is inhaled with a certain strength. For example, using $T_{thre}$ as a temperature threshold in the graph 600 leads to a problem in that although the residual amount of the aerosol source in the retainer and the like is not sufficient, it is falsely determined that the residual amount of the aerosol source in the retainer and the like is sufficient when the aerosol inhalator 100 is inhaled with a certain strength or higher.

This problem can be addressed by comparing the temperature of the load 132 with a predetermined temperature threshold $T'_{thre}(v)$ which is equal to or higher than the temperature $T'_{satmax}(v)$ which is the boiling point Tap. or the like of the aerosol source or the temperature according to the inhalation strength and equal to or lower than the equilibrium temperature $T'_{depmax}(v)$ according to the inhalation strength. As a specific example, only when the temperature of the load 132 exceeds the temperature threshold $T'_{thre}(v)$, it is necessary to determine that the residual amount of the aerosol source in the retainer and the like is not sufficient.

In another aspect, when it is assumed that $T_{thre}$ in the graph 600 is regarded as the temperature threshold set without taking into consideration the inhaling on the aerosol inhalator 100, and the magnitude of a difference between the equilibrium temperature $T_{equi.}$ and the temperature $T'_{depmax}(v)$ is represented as $\varepsilon_2(v)$, if the temperature threshold $T'_{thre}(v)$ to be compared is set to $T_{thre} - \varepsilon_2(v)$, the above-described problem does not occur.

The temperature change 650 of the load 132 per a predetermined time period shows a temperature change of the load 132 per a time period $\Delta t$ between a time $t_1$ and a time $t_2$ in the graph 600. A reference numeral 660A represents a temperature change of the load 132 per a predetermined time period $\Delta t$ when the residual amount of the aerosol source in the retainer and the like is sufficient and the aerosol inhalator 100 is not inhaled, and corresponds to the temperature change 360 in FIG. 3. On the other hand, a reference numeral 660B represents a temperature change of the load 132 per a predetermined time period $\Delta t$ when the residual amount of the aerosol source in the retainer and the like is sufficient and the aerosol inhalator 100 is inhaled with a first strength $v_1$. The temperature change 660B shows that when the residual amount of the aerosol source in the retainer and the like is sufficient and the aerosol inhalator 100 is inhaled with the first strength $v_1$, the temperature of the load 132 per a predetermined time period $\Delta t$ is increased by $\Delta T'_{sat}(v_1)$ which is smaller than $\Delta T_{sat}$. A reference numeral 660C represents a temperature change of the load 132 per a predetermined time period $\Delta t$ when the residual amount of the aerosol source in the retainer and the like is sufficient and the aerosol inhalator 100 is inhaled with a second strength $v_2$. The temperature change 660C shows that when the residual amount of the aerosol source in the retainer and the like is sufficient and the aerosol inhalator 100 is inhaled with the second strength $v_2$, the temperature of the load 132 per a predetermined time period $\Delta t$ is increased by $\Delta T'_{sat}(v_2)$ which is smaller than $\Delta T'_{sat}(v_1)$.

That is, the temperature changes 660A to 660C show that there exists a system that depending on the structure of the load 132, the temperature rise width of the load 132 per a predetermined time period is decreased as the inhalation strength relative to the aerosol inhalator 100 is increased, when the residual amount of the aerosol source in the retainer and the like is sufficient. In such a system, even when the residual amount of the aerosol source in the retainer and the like is not sufficient, the temperature change of the load 132 per a predetermined time period $\Delta t$ may be reduced as the inhalation strength relative to the aerosol inhalator 100 is increased. Accordingly, in such a system, using the temperature change threshold set without taking into consideration the inhaling on the aerosol inhalator 100 leads to a problem in that although the residual amount of the aerosol source in the retainer and the like is not sufficient, it may be falsely determined that the residual amount of the aerosol source in the retainer and the like is sufficient. Reference numerals 670A and 670B in the graph 650 represent exemplary temperature profiles of the load 132, respectively, in which the reference numeral 670A represents the temperature profile when the residual amount of the aerosol source in the retainer and the like is not sufficient and the aerosol inhalator 100 is not inhaled, and the reference numeral 670B represents the temperature profile when the residual amount of the aerosol source in the retainer and the like is not sufficient and the aerosol inhalator 100 is inhaled with a certain strength. For example, using $\Delta T_{thre}$ in the temperature change 650 as a temperature threshold leads to a problem in that although the residual amount of the aerosol source in the retainer and the like is not sufficient, it is falsely determined that the residual amount of the aerosol source in the retainer and the like is sufficient when the aerosol inhalator 100 is inhaled with the above-described certain strength or higher.

This problem can be addressed by comparing the temperature change of the load 132 per a predetermined time period $\Delta t$ with $\Delta T_{sat}$ or a predetermined temperature change threshold $\Delta T'_{thre}(v)$ which is equal to or larger than $\Delta T'_{sat}(v)$ as a temperature change according to the inhalation strength and equal to or smaller than $\Delta T'_{dep}$ as a temperature change according to the inhalation strength. As a specific example, only when the temperature change of the load 132 per a predetermined time period $\Delta t$ exceeds the temperature change threshold $\Delta T'_{thre}(v)$, it is necessary to determine that the residual amount of the aerosol source in the retainer and the like is not sufficient.

In another aspect, when it is assumed that $\Delta T_{thre}$ in the temperature change 650 is regarded as the temperature change threshold set without taking into consideration the inhaling on the aerosol inhalator 100, and the magnitude of a difference between $\Delta T_{dep}$ and $\Delta T'_{dep}(v)$ is represented as $\Delta \varepsilon_2(v)$, if the temperature change threshold $\Delta T'_{thre}(v)$ to be compared is dynamically set to $\Delta T_{thre} - \Delta \varepsilon_2(v)$, the above-described problem does not occur.

Figure 7:
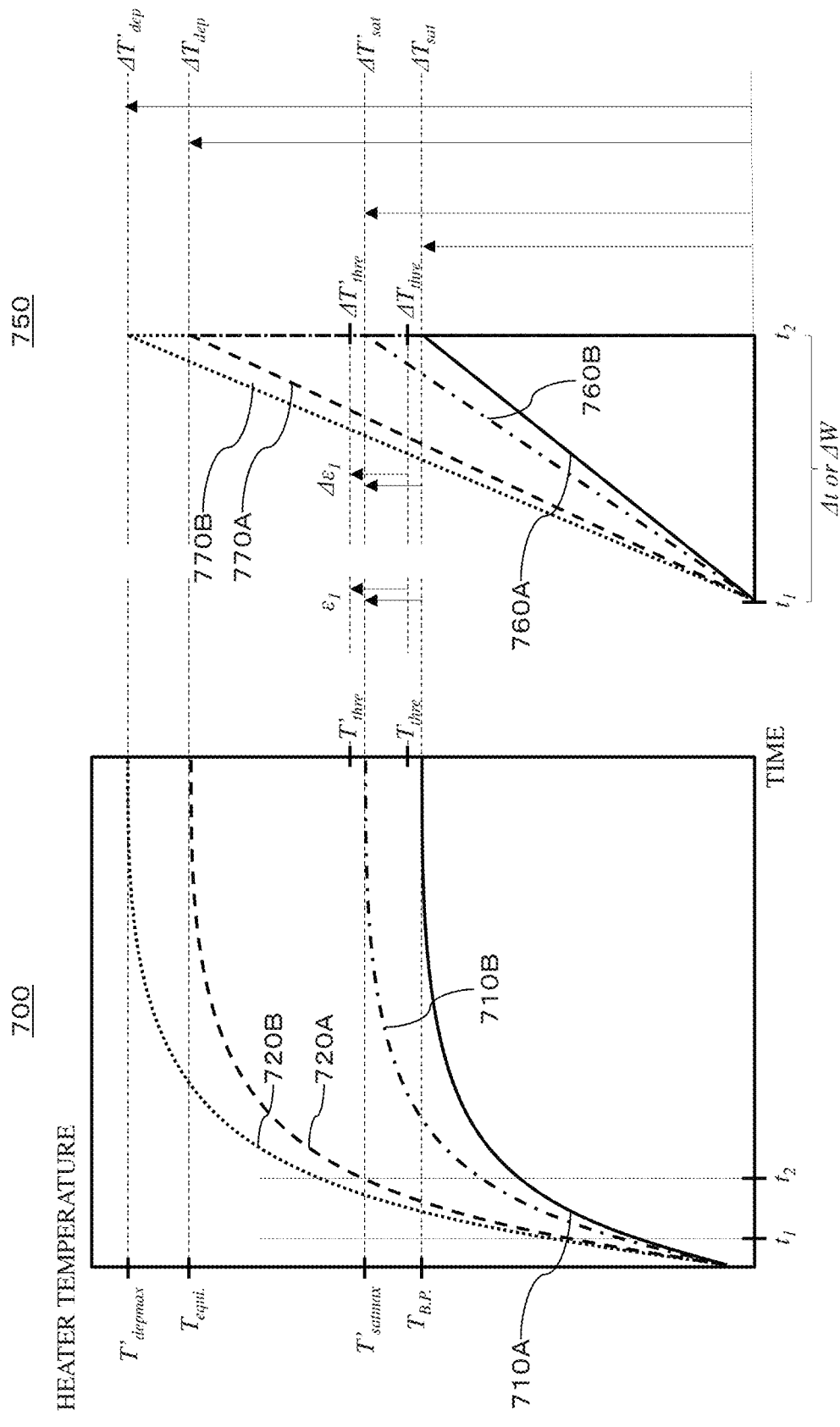
FIG. 7 is a graph schematically showing a temperature profile of a load of an aerosol inhalator having a certain structure, taking inhalation into consideration, and illustrates a temperature change of a load per a predetermined time period or a predetermined amount of electric power.

FIG. 7 shows a graph 700 including a schematic temperature profile of the load 132 in which an exemplary temperature profile in the graph 450C of FIG. 4B is simplified for easy understanding, and illustrates a temperature change 750 of the load 132 per a predetermined time period.

A reference numeral 710A in the graph 700 represents a schematic temperature profile of the load 132 when the residual amount of the aerosol source in the retainer and the like is sufficient and the aerosol inhalator 100 is not inhaled, and corresponds to the temperature profile 310 in FIG. 3. On the other hand, a reference numeral 710B represents a schematic temperature profile of the load 132 when the residual amount of the aerosol source in the retainer and the like is sufficient and the aerosol inhalator 100 is inhaled with a first strength. The temperature profile 710B shows that when the residual amount of the aerosol source in the retainer and the like is sufficient and the aerosol inhalator 100 is inhaled with the first strength, the temperature of the load 132 reaches the steady state at a temperature $T'_{satmax}$ which is higher than the boiling point $T_{B.P.}$ or the like of the aerosol after the temperature increase of the load 132 is started. However, a reference numeral 710B represents a schematic temperature profile of the load 132 when the residual amount of the aerosol source in the retainer and the like is sufficient and the aerosol inhalator 100 is inhaled with a second strength which is different from the first strength. Accordingly, the temperature profile 710B shows that even when the residual amount of the aerosol source in the retainer and the like is sufficient and the aerosol inhalator 100 is inhaled with the second strength, the temperature of the load 132 reaches the steady state at a temperature $T'_{satmax}$ after the temperature increase of the load 132 is started.

That is, the temperature profiles 710A and 710B show that there exists a system that depending on the structure of the load 132, the temperature of the load 132 at the steady state is increased by the inhaling on the aerosol inhalator 100 but the temperature rise width is nearly unchanged at least for a range of inhalation strengths, when the residual amount of the aerosol source in the retainer and the like is sufficient. In such a system, using the temperature threshold set without taking into consideration the inhaling on the aerosol inhalator 100 leads to a problem in that although the residual amount of the aerosol source in the retainer and the like is sufficient, it may be falsely determined that the residual amount of the aerosol source in the retainer and the like is not sufficient. For example, using $T_{thre}$ as a temperature change threshold in the graph 700 leads to a problem in that although the residual amount of the aerosol source in the retainer and the like is sufficient, it may be falsely determined that the residual amount of the aerosol source in the retainer and the like is not sufficient when the aerosol inhalator 100 is inhaled.

Figure 5:
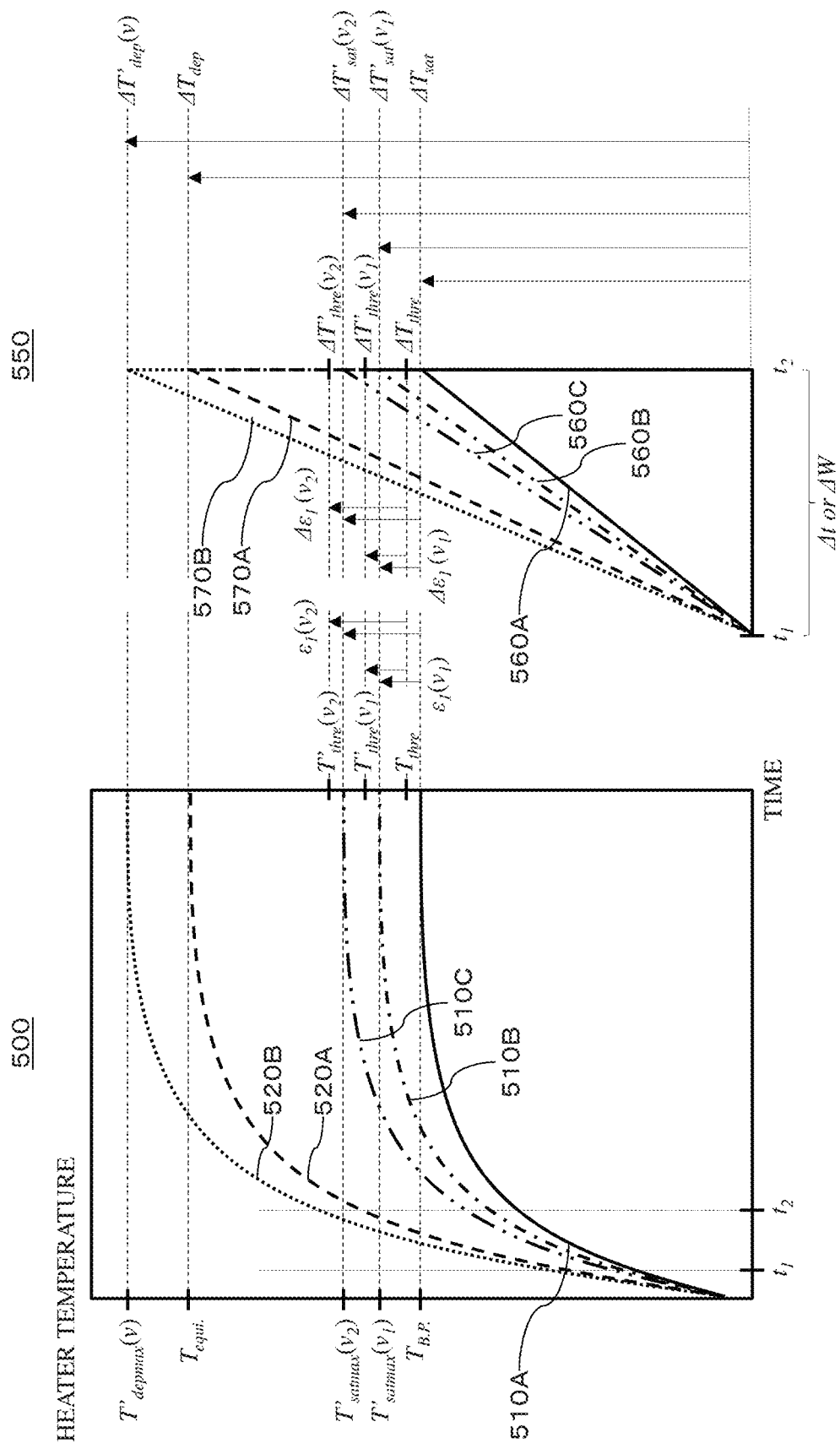
FIG. 5 is a graph schematically showing a temperature profile of a load of an aerosol inhalator having a certain structure, taking inhalation into consideration, and illustrates a temperature change of a load per a predetermined time period or a predetermined amount of electric power.

The problem occurring in such a system can be similarly addressed by regarding $T_{satmax}(v)$, $\varepsilon_1(v)$ and $T'_{depmax}(v)$ according to the inhalation strength and $T'_{thre}(v)$ as constants $T'_{satmax}$, $\varepsilon_1$ and $T'_{depmax}$ and $T'_{thre}$ in the technique described above with respect to the graph 500 of FIG. 5.

The inventors have discovered that there may exist a system that depending on the structure of the load 132, the temperature of the load 132 at the steady state is decreased by the inhaling on the aerosol inhalator 100 but the temperature decrease width is nearly unchanged at least for a range of inhalation strengths, when the residual amount of the aerosol source in the retainer and the like is sufficient. The problem occurring in such a system can be similarly addressed by regarding $T_{satmax}(v)$, $\varepsilon_2(v)$ and $T'_{depmax}(v)$ according to the inhalation strength and $T'_{thre}(v)$ as constants $T'_{satmax}$, $\varepsilon_2$ and $T'_{depmax}$ and $T'_{thre}$ in the technique described above with respect to the graph 600 of FIG. 6.

The temperature change 750 of the load 132 per a predetermined time period shows a temperature change of the load 132 per a time period $\Delta t$ between a time $t_1$ and a time $t_2$ in the graph 700. A reference numeral 760A represents a temperature change of the load 132 per a predetermined time period $\Delta t$ when the residual amount of the aerosol source in the retainer and the like is sufficient and the aerosol inhalator 100 is not inhaled, and corresponds to the temperature change 360 in FIG. 3. On the other hand, a reference numeral 760B represents a temperature change of the load 132 per a predetermined time period Δt when the residual amount of the aerosol source in the retainer and the like is sufficient and the aerosol inhalator 100 is inhaled with a first strength. The temperature change 760B shows that when the residual amount of the aerosol source in the retainer and the like is sufficient and the aerosol inhalator 100 is inhaled with the first strength, the temperature of the load 132 per a predetermined time period Δt is increased by ΔT'$_{sat}$ which is larger than ΔT$_{sat}$. However, a reference numeral 760B represents a temperature change of the load 132 per a predetermined time period Δt when the residual amount of the aerosol source in the retainer and the like is sufficient and the aerosol inhalator 100 is inhaled with a second strength which is different from the first strength. Accordingly, the temperature change 760B shows that even when the residual amount of the aerosol source in the retainer and the like is sufficient and the aerosol inhalator 100 is inhaled with the second strength, the temperature of the load 132 per a predetermined time period Δt is increased by ΔT'$_{sat}$.

That is, the temperature changes 760A and 760B show that there exists a system that depending on the structure of the load 132, the temperature rise width of the load 132 per a predetermined time period is increased by the inhaling on the aerosol inhalator 100 but the degree of an increase in the temperature rise width is nearly unchanged at least for a range of inhalation strengths, when the residual amount of the aerosol source in the retainer and the like is sufficient. In such a system, using the temperature change threshold set without taking into consideration the inhaling on the aerosol inhalator 100 leads to a problem in that although the residual amount of the aerosol source in the retainer and the like is sufficient, it may be falsely determined that the residual amount of the aerosol source in the retainer and the like is not sufficient. For example, using ΔT$_{thre}$ in the temperature change 750 as a temperature change threshold leads to a problem in that although the residual amount of the aerosol source in the retainer and the like is sufficient, it may be falsely determined that the residual amount of the aerosol source in the retainer and the like is not sufficient when the aerosol inhalator 100 is inhaled.

The problem occurring in such a system can be similarly addressed by regarding ΔT'$_{sat}$(v), Δε$_1$(v) and ΔT'$_{dep}$(v) according to the inhalation strength and ΔT'$_{thre}$(v) as constants ΔT'$_{sat}$, Δε$_1$ and ΔT'$_{dep}$ and ΔT'$_{thre}$ in the technique described above with respect to the graph 550 of FIG. 5.

The inventors have discovered that that there may exist a system that depending on the structure of the load 132, the temperature rise width of the load 132 per a predetermined time period is decreased by the inhaling on the aerosol inhalator 100 but the degree of decrease in the temperature rise width is nearly unchanged at least for a range of inhalation strengths, when the residual amount of the aerosol source in the retainer and the like is sufficient. The problem occurring in such a system can be similarly addressed by regarding ΔT'$_{sat}$(v), Δε$_2$(v) and ΔT'$_{dep}$(v) according to the inhalation strength and ΔT'$_{thre}$(v) as constants ΔT'$_{sat}$, Δε$_2$ and ΔT'$_{dep}$ and ΔT'$_{thre}$ in the technique described above with respect to the temperature change 650 of FIG. 6.

2-3. Discussion about Behavior of Heater Temperature

Hereinafter, one potential cause that the above-described systems exist will be described.

The temperature $T_{HTR}(t+\Delta t)$ of the load 132 after the elapse of a predetermined time period Δt from a time t can be basically represented as follows.

[Formula 2]

$$T_{HTR}(t + \Delta t) = T_{HTR}(t) + \frac{d}{dt}T_{HTR}(t) \cdot \Delta t \quad (5)$$
$$= T_{HTR}(t) + v_{rising} \cdot \Delta t - |v_{cooling}| \cdot \Delta t$$

Where, $v_{rising}$ and $v_{cooling}$ represent a temperature rise rate of the load 132 resulting from a factor to increase the temperature of the load 132 and a cooling rate of the load 132 resulting from a factor to decrease the temperature of the load 132, respectively. Since the cooling rate $v_{cooling}$ can be divided into $v_{coolant}$ resulting from refrigerant in the system (that is, heat transfer to the aerosol source and air constantly existing in the system) and $v_{air}$ resulting from air cooling due to the inhaling on the aerosol inhalator 100 (that is, cooling effect of air positively contacting the load 132 only at the time of inhaling), the expression (5) is rewritten as follows. Note that although $v_{coolant}$ and $v_{air}$ are influenced by air existing around the load 132, $v_{coolant}$ acts at the time of both of inhaling and non-inhaling, and $v_{air}$ acts only at the time of inhaling.

[Formula 3]

$$T_{HTR}(t+\Delta t)=T_{HTR}(t)+v_{rising} \cdot \Delta t-(|v_{coolant}|+|v_{air}|) \cdot \Delta t \quad (6)$$

Since the temperature rise of the load 132 depends on the electric power applied to the load 132, the temperature rise rate $v_{rising}$ is represented as follows.

[Formula 4]

$$v_{rising} = \frac{dQ_{HTR}}{dt} \cdot \frac{1}{C_{HTR}} \quad (4)$$
$$= \frac{P_{HTR}(T_{HTR}(t))}{C_{HTR}} = \frac{V_{HTR} \cdot I_{HTR}(T_{HTR}(t))}{C_{HTR}} = \frac{V_{HTR}^2}{C_{HTR} \cdot R_{HTR}(T_{HTR}(t))}$$

Where, $P_{HTR}$, $V_{HTR}$, $I_{HTR}$, and $R_{HTR}$ represent an electric power applied to the load 132, a voltage applied to the load 132, a current flowing in the load 132, and a resistance of the load 132, respectively. Note that since the voltage $V_{HTR}$ may be constant but the resistance $R_{HTR}$ depends on the temperature $T_{HTR}$ of the load 132, that is a function of the temperature $T_{HTR}$, the electric power $P_{HTR}$ and the current $I_{HTR}$ are a function of the temperature $T_{HTR}$. $Q_{HTR}$ and $C_{HTR}$ represent the total amount of heat and the sum of heat capacities of components (including the load 132 itself, at least part of the aerosol base 116B or the retainer 130, at least part of the aerosol source retained in the aerosol base 116B or the retainer 130) that produce the temperature change together with the load 132, respectively.

The cooling rate $v_{coolant}$ resulting from the refrigerant in the system of the load 132 is represented as follows by Newton's law of cooling.

[Formula 5]

$$|v_{coolant}| = \left| -\frac{\alpha_1 \cdot S_1}{C_{HTR}}(T_{HTR}(t) - T_{m1}) \right| + \left| -\frac{\alpha_2 \cdot S_2}{C_{HTR}}(T_{HTR}(t) - T_{m2}) \right| \quad (8)$$

Where $\alpha_1$, $\alpha_2$, $S_1$ and $S_2$ represent coefficients determined by the structures in a vicinity of the load 132 of the aerosol inhalator 100. $T_{m1}$ and $T_{m2}$ represent the temperature of the gas in the vicinity of the load 132 and the temperature of the aerosol source in the vicinity of the load 132, respectively.

When the expression (6) is rewritten using the expressions (7) and (8), the following expression is obtained.

[Formula 6]

$$T_{HTR}(t + \Delta t) = T_{HTR}(t) + \quad (9)$$
$$\frac{V_{HTR}^2}{C_{HTR} \cdot R_{HTR}(T_{HTR}(t))} \cdot \Delta t -$$
$$\left\{ \left| -\frac{a_1 \cdot S_1}{C_{HTR}}(T_{HTR}(t) - T_{m1}) \right| + \left| -\frac{\alpha_2 \cdot S_2}{C_{HTR}}(T_{HTR}(t) - T_{m2}) \right| \right\} \cdot \Delta t - |v_{air}| \cdot \Delta t$$

The heat capacity $C_{HTR}$ will be discussed below. When the electric power is supplied to the load 132 in the case where the aerosol source exists in the aerosol base 116B or the retainer 130, the aerosol source in the vicinity of the load 132 in the aerosol base 116B or the retainer 130 is atomized and thereby the aerosol is generated. This means that the aerosol source in the vicinity of the load 132 in the aerosol base 116B or the retainer 130 is consumed by atomizing the aerosol source. The amount of consumed aerosol source is filled with the surrounding aerosol source which has not been atomized. In this regard, when there is no inhaling, the generated aerosol remains in the atomizing part 118A or 118B (hereinafter, referred to as an "atomizing part 118"), and the atomizing part 118 becomes saturated with the aerosol. Therefore, the generation of aerosol is suppressed, and an amount of the aerosol source in the vicinity of the load 132 in the aerosol base 116B or the retainer 130 which is consumed by atomizing the aerosol source tends to be relatively reduced. On the other hand, when there is inhaling, the generated aerosol is inhaled. Therefore, the generation of the aerosol is promoted, and an amount of the aerosol source in the vicinity of the load 132 in the aerosol base 116B or the retainer 130 which is consumed by atomizing the aerosol source tends to be relatively increased. Accordingly, assuming that the rate of filling the aerosol source is not influenced by the inhalation or the influence is smaller than an influence on an amount of the aerosol source consumed, if any, in the case where there is inhaling, an amount or mass of the aerosol source in the vicinity of the load 132 in the aerosol base 116B or the retainer 130 while power is being supplied tends to be low as compared with the case where there is no inhaling. Here, since the heat capacity of a certain substance is determined by the product of the specific heat of the substance and the mass or the substance, assuming that the aerosol source in the vicinity of the load 132 is included in the above-described "components that produce the temperature change together with the load 132," the heat capacity $C_{HTR}$ changes according to the inhalation.

The cooling rate $v_{air}$ changes according to the inhalation by the definition. In light of the above, when the heat capacity $C_{HTR}$ and the cooling rate $v_{air}$ are represented as the functions of the flow velocity v, $C_{HTR}(v)$ and $v_{air}(v)$, the expression (9) is rewritten as follows.

[Formula 7]

$$T_{HTR}(t + \Delta t) = T_{HTR}(t) + \quad (10)$$
$$\frac{V_{HTR}^2}{C_{HTR}(v) \cdot R_{HTR}(T_{HTR}(t))} \cdot \Delta t -$$
$$\left\{ \left| -\frac{a_1 \cdot S_1}{C_{HTR}(v)}(T_{HTR}(t) - T_{m1}) \right| + \left| -\frac{\alpha_2 \cdot S_2}{C_{HTR}(v)}(T_{HTR}(t) - T_{m2}) \right| \right\} \cdot \Delta t -$$
$$|v_{air}(v)| \cdot \Delta t$$

The expression (10) represents that the temperature of the load 132 is also the function of the flow velocity v. The reason why the above-described systems having different properties exist is presumably because the degree of change in each of the second to fourth terms of the expression (10) according to the change in the flow velocity v depends on at least the structure in the vicinity of the load 132.

2-4. Relationship Between Structure in a Vicinity of the Load 132 and Behavior of Heater Temperature The relationship between the structure in the vicinity of the load 132 illustrated in FIG. 4A and the behavior of the heater temperature will be further discussed using the temperature of the load 132 modeled with the expression (10).

In all of the structures 400A to 400C in the vicinity of the load 132, when the user performs inhaling, the generation of aerosol by the load 132 is promoted, whereby the aerosol source in the vicinity of the load 132 in the aerosol base 116B or the retainer 130 is reduced. That is, the heat capacity is reduced as the inhalation strength of the user is increased, resulting that the second term on the right side of the expression (10) is increased.

In the structure 400A in the vicinity of the load 132, the load 132 (420) is disposed in a partially recessed portion of the retainer 410, and therefore in the structure 400A, the air stream does not directly contact the load 132. In this way, an air-cooling effect resulting from the inhaling shown in the fourth term on the right side of the expression (10) is weakened. In the structure 400A in the vicinity of the load 132, since there is a tendency that the temperature rise rate resulting from the second term on the right side of the expression (10) is stronger than the cooling rate resulting from the third term and the fourth term on the right side of the expression (10), the heater temperature may be increased depending on the inhalation strength.

In the structure 400B in the vicinity of the load 132, the air stream contacts the entire load 132 (420). In this way, an air-cooling effect resulting from the inhaling shown in the fourth term on the right side of the expression (10) is strengthened. In the structure 400B in the vicinity of the load 132, since there is a tendency that the cooling rate resulting from the third term and the fourth term on the right side of the expression (10) is stronger than the temperature rise rate resulting from the second term on the right side of the expression (10), the heater temperature may be decreased depending on the inhalation strength.

In the structure 400C in the vicinity of the load 132, the air stream contacts a center portion of the load 132 (420). In this way, an air-cooling effect resulting from the inhaling shown in the third term on the right side of the expression (10) is slightly strengthened. In the structure 400C in the vicinity of the load 132, there is a tendency that the cooling rate resulting from the third term and the fourth term on the right side of the expression (10) and the temperature rise rate resulting from the second term on the right side of the expression (10) come to an equilibrium with stronger inhaling, and therefore although the heater temperature is increased, the heater temperature may not depend on the inhalation strength.

2-5. Remarks about Principle

As described above, the temperature of the load 132 can be obtained from a resistance value of the load 132, a value of the voltage applied to the load 132 and the like, a value of the current flowing in the load 132 and the like. Therefore, the residual amount of the aerosol source in the retainer and the like can be determined by comparing the resistance value of the load 132, the value of the voltage applied to the load 132 and the like, and the value of the current flowing in the load 132 and the like with the resistance threshold, the voltage threshold or the current threshold corresponding to the above-described predetermined temperature threshold $T'_{thre}(v)$ or $T'_{thre}$.

In addition, the residual amount of the aerosol source in the retainer and the like can be determined by comparing the change in the resistance value of the load 132 per a predetermined time period $\Delta t$, the change in the value of the voltage applied to the load 132 and the like, or the change in the value of the current flowing in the load 132 and the like with the resistance change threshold, the voltage change threshold or the current change threshold corresponding to the above-described predetermined temperature change threshold $\Delta T'_{thre}(v)$ or $\Delta T'_{thre}$.

Furthermore, although the above description has been made on the change in the temperature per a predetermined time period $\Delta t$, the residual amount of the aerosol source in the retainer and the like can be also determined using the temperature change, the resistance change, the voltage change or the current change per a predetermined amount of electric power $\Delta W$ supplied to the load 132.

3. Process for Determining Occurrence of Depletion or Insufficiency of Aerosol Source Hereinafter, a process for determining occurrence of depletion or insufficiency of the aerosol source based on the above-described principle, according to an embodiment of the present disclosure, will be described. In the process to be described later, it is assumed that the controller 106 performs all of the steps. However, note that a part of the steps may be performed by another component of the aerosol inhalator 100.

3-1. Overview of Process

Figure 8A:
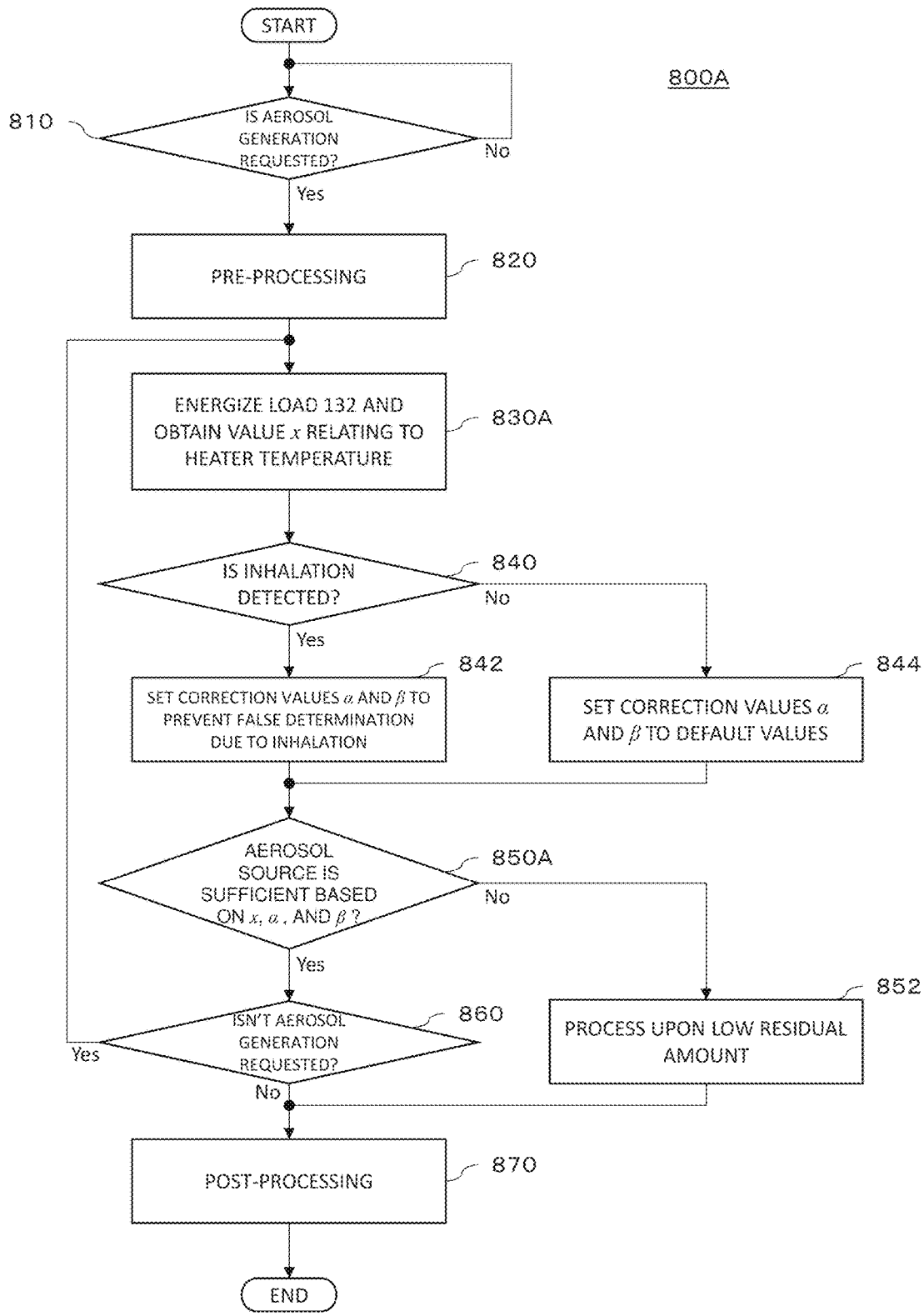
FIG. 8A is a flowchart of an exemplary process for determining occurrence of depletion or insufficiency of the aerosol source according to an embodiment of the present disclosure.

FIG. 8A is a flowchart of an exemplary process 800A for determining occurrence of depletion or insufficiency of the aerosol source according to an embodiment of the present disclosure. The exemplary process 800A is suitable for the aerosol inhalator 100 in which the temperature of the load 132 changes according to the inhalation.

A reference numeral 810 denotes a step of determining whether the generation of the aerosol has been requested. For example, when the controller 106 detects the inhalation start by the user based on the information obtained from the pressure sensor and the flow velocity sensor or the flow rate sensor, and the like, the controller 106 may determine that the generation of the aerosol has been requested. More specifically, for example, the controller 106 can determine that the inhalation start by the user has been detected when an output value or a pressure of the pressure sensor has fallen below a predetermined threshold. In addition, for example, the controller 106 can determine that the inhalation start by the user has been detected when an output value, i.e., a flow velocity or a flow rate of the flow velocity sensor or the flow rate sensor has exceeded a predetermined threshold. In such a determining method, the aerosol can be generated to match the feeling of the user, and therefore the flow velocity sensor or the flow rate sensor is particularly suitable. Alternatively, when the output values of these sensors start to change continuously, the controller 106 may determine that the inhalation start by the user has been detected. Alternatively, the controller 106 may determine that the inhalation start by the user has been detected based on the fact that a button for starting the generation of the aerosol has been pressed. Alternatively, the controller 106 may determine that the inhalation start by the user has been detected based on both of the information obtained from the flow velocity sensor or the flow rate sensor and the pressing of the button.

The method 800A includes a loop process, and a reference numeral 820 denotes a step of performing pre-processing to be performed prior to the loop process. Note that step 820 may not be necessary in some embodiments.

A reference numeral 830A denotes a step of energizing the load 132 and obtaining a value x relating to the heater temperature. The value x relating to the heater temperature may be any value capable of changing according to the resistance value, the voltage value, the current value, and the other heater temperature or obtaining the heater temperature. Note that the value x relating to the heater temperature may be the heater temperature itself. In addition, the value x relating to the heater temperature includes a value relating to the resistance value of the load 132. The value relating to the resistance value of the load 132 may be any value capable of changing according to the voltage value, the current value, and the other resistance value of the load 132 or obtaining the resistance value of the load 132. Note that the value relating to the resistance value of the load 132 may be the resistance value itself of the load 132.

A reference numeral 840 denotes a step of determining whether the inhalation has been detected. In step 840, a method similar to the method of detecting the inhalation in step 810 may be used, but it is necessary to detect that the user actually inhales the aerosol inhalator 100. Accordingly, the above-described pressure sensor and flow velocity sensor or flow rate sensor are suitable for the detection. It is not necessary to apply the same method for the detection of the inhalation in step 810 and the detection of the inhalation in step 840. For example, in one of step 810 and step 840, the pressure sensor may be used for the detection of the inhalation, and in the other, the flow rate sensor may be used for the detection of the inhalation. Furthermore, when the inhalation is detected using the threshold, the thresholds used in steps 810 and 840 may be the same or different. When it is determined that the inhalation has been detected, the process proceeds to step 842, otherwise the process proceeds to step 844.

A reference numeral 842 denotes a step of setting correction values $\alpha$ and $\beta$ which are used in step 850A and the like described later, to prevent false determination caused by the inhalation. A reference numeral 844 denotes a step of setting the correction values $\alpha$ and $\beta$ to default values.

A reference numeral 850A denotes a step of determining whether the aerosol source is sufficient, based on the value x relating to the heater temperature and the correction values $\alpha$ and $\beta$. When it is determined that the aerosol source is sufficient, the process proceeds to step 860, otherwise the process proceeds to step 852.

A reference numeral 852 denotes a step of performing a process upon low residual amount performed when the residual amount of the aerosol is low.

A reference numeral 860 denotes a step of determining whether the generation of the aerosol is not requested. For example, when the controller 106 detects the inhalation completion by the user based on the information obtained from the pressure sensor and the flow velocity sensor or the flow rate sensor, and the like, the controller 106 may determine that the generation of the aerosol is not requested. Here, for example, the controller 106 can determine that the inhalation completion by the user has been detected, in other words, the generation of the aerosol is not requested, when the output value or the pressure of the pressure sensor has exceeded a predetermined threshold. In addition, for example, the controller 106 can determine that the inhalation completion by the user has been detected, in other words, the generation of the aerosol is not requested, when an output value, i.e., a flow velocity or a flow rate of the flow velocity sensor or the flow rate sensor has fallen below a predetermined threshold. Note that this threshold may be larger than, equal to, or smaller than the threshold in step 810. Alternatively, the controller 106 may determine that the inhalation completion by the user has been detected, in other words, the generation of the aerosol is not requested based on the fact that a button for starting the generation of the aerosol has been released. Alternatively, the controller 106 may determine that the inhalation completion by the user has been detected, in other words, the generation of the aerosol is not requested when a predetermined condition that a predetermined time period has elapsed after the button for starting the generation of the aerosol is pressed has been satisfied. When it is determined that the generation of the aerosol is not requested, the process proceeds to step 870, otherwise the process returns to step 830A and loops.

A reference numeral 870 denotes a step of performing post-processing to be performed after exiting from the loop process. Note that step 870 may not be necessary in some embodiments.

Figure 8B:
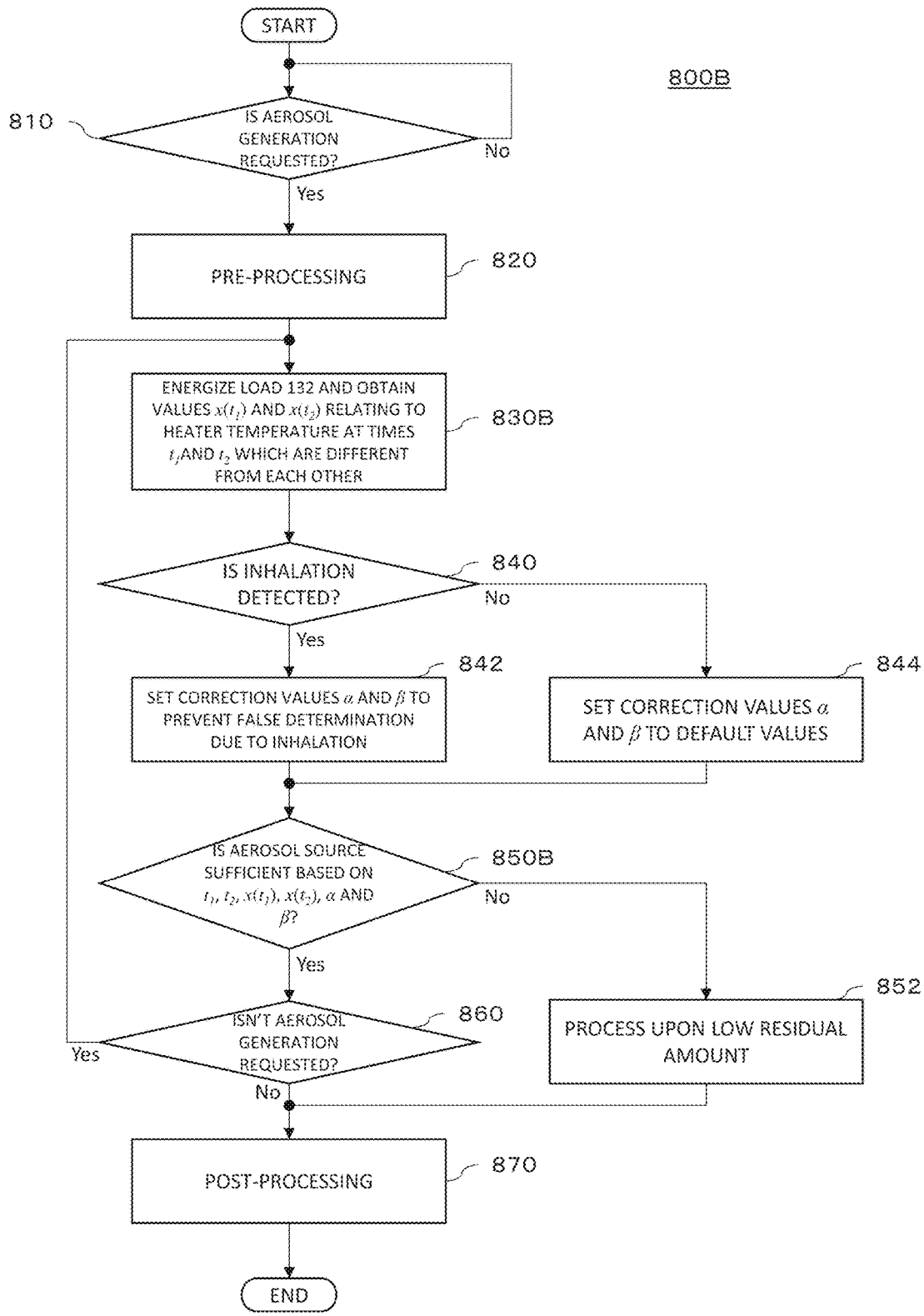
FIG. 8B is a flowchart of an exemplary process for determining occurrence of depletion or insufficiency of the aerosol source according to an embodiment of the present disclosure.

FIG. 8B is a flowchart of another exemplary process 800B for determining occurrence of depletion or insufficiency of the aerosol source according to an embodiment of the present disclosure. The exemplary process 800B is suitable for the aerosol inhalator 100 in which the temperature change of the load 132 per a predetermined time period is changed due to the inhalation. A part of steps included in the exemplary process 800B is the same as that already described above. Hereinafter, the steps included in the exemplary process 800B which are not described above will be described.

A reference numeral 830B denotes a step of energizing the heater and obtaining values $x(t_1)$ and $x(t_2)$ relating to the heater temperature at a different point of the time $t_1$ and $t_2$. The values $x(t_1)$ and $x(t_2)$ relating to the heater temperature are similar to the value x relating to the heater temperature which has been described with respect to step 830A.

A reference numeral 850B denotes a step of determining whether the aerosol source is sufficient based on the times $t_1$ and $t_2$, values $x(t_1)$ and $x(t_2)$ relating to the heater temperature, and the correction values α and β. When it is determined that the aerosol source is sufficient, the process proceeds to step 860, otherwise the process proceeds to step 852.

Figure 8C:
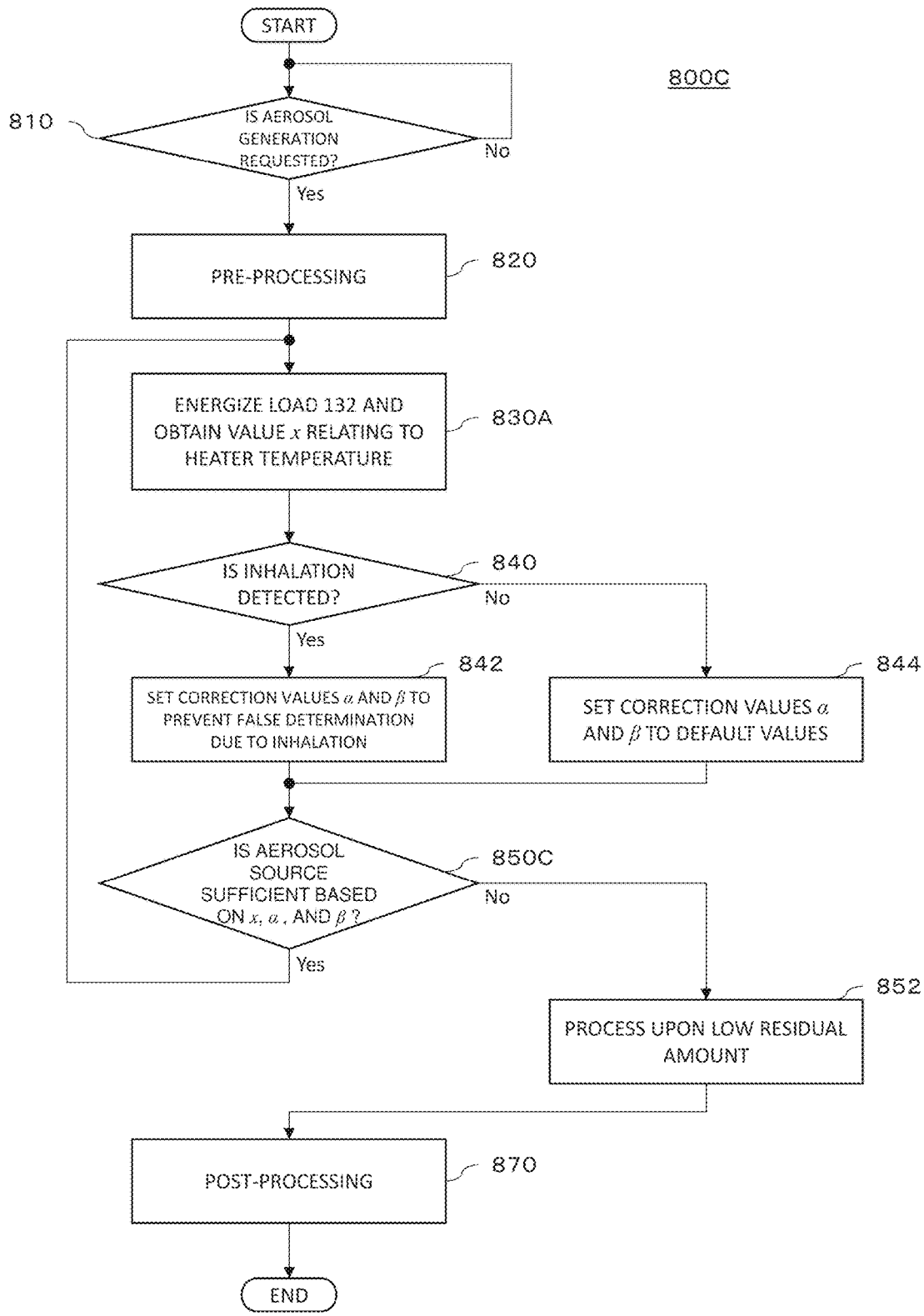
FIG. 8C is a flowchart of an exemplary process for determining occurrence of depletion or insufficiency of the aerosol source according to an embodiment of the present 118A or may communicate with the inside of the reservoir 116A again through the atomizing part 118A. The aerosol source is carried from the reservoir 116A to the atomizing part 118A by a capillary effect of the retainer 130. As an example, the atomizing part 118A includes a heater including the load 132 electrically connected to the power supply 110. The heater is disposed in contact with or in close contact with the retainer 130. When an inhaling action or another operation by a user is detected, the controller 106 controls power supply to the heater of the atomizing part 118A and heats the aerosol source carried through the retainer 130 to thereby atomize the aerosol source. The air intake channel 120 is connected to the atomizing part 118A. The air intake channel 120 communicates with the outside of the aerosol inhalator 100A. The aerosol generated in the atomizing part 118A is mixed with air taken in via the air intake channel 120. Mixed fluid of the aerosol and the air is delivered to the aerosol flow path 121 as indicated by an arrow 124. The aerosol flow path 121 has a tubular structure for transporting the mixed fluid of the aerosol and the air generated in the atomizing part 118A to the suction port part 122.

FIG. 8C is a flowchart of still another exemplary process 800C for determining occurrence of depletion or insufficiency of the aerosol source according to an embodiment of the present disclosure. In the exemplary process 800C, a part of the exemplary process 800A is performed as another process or an interrupt process (described later with respect to FIG. 8I) which is performed in parallel. Accordingly, the exemplary process 800C is suitable for the aerosol inhalator 100 in which the temperature of the load 132 changes according to the inhalation. A part of steps included in the exemplary process 800C is the same as that already described above. Hereinafter, the steps included in the exemplary process 800C which are not described above will be described.

A reference numeral 850C denotes a step of determining whether the aerosol source is sufficient, based on the value x relating to the heater temperature and the correction values α and β. Although the content of the process in step 850C is the same as that in step 850A, the branch from step 850C is different from that from step 850A. That is, when it is determined that the aerosol source is sufficient, the process returns to step 830A and loops. Otherwise, the process proceeds to step 852.

Figure 8D:
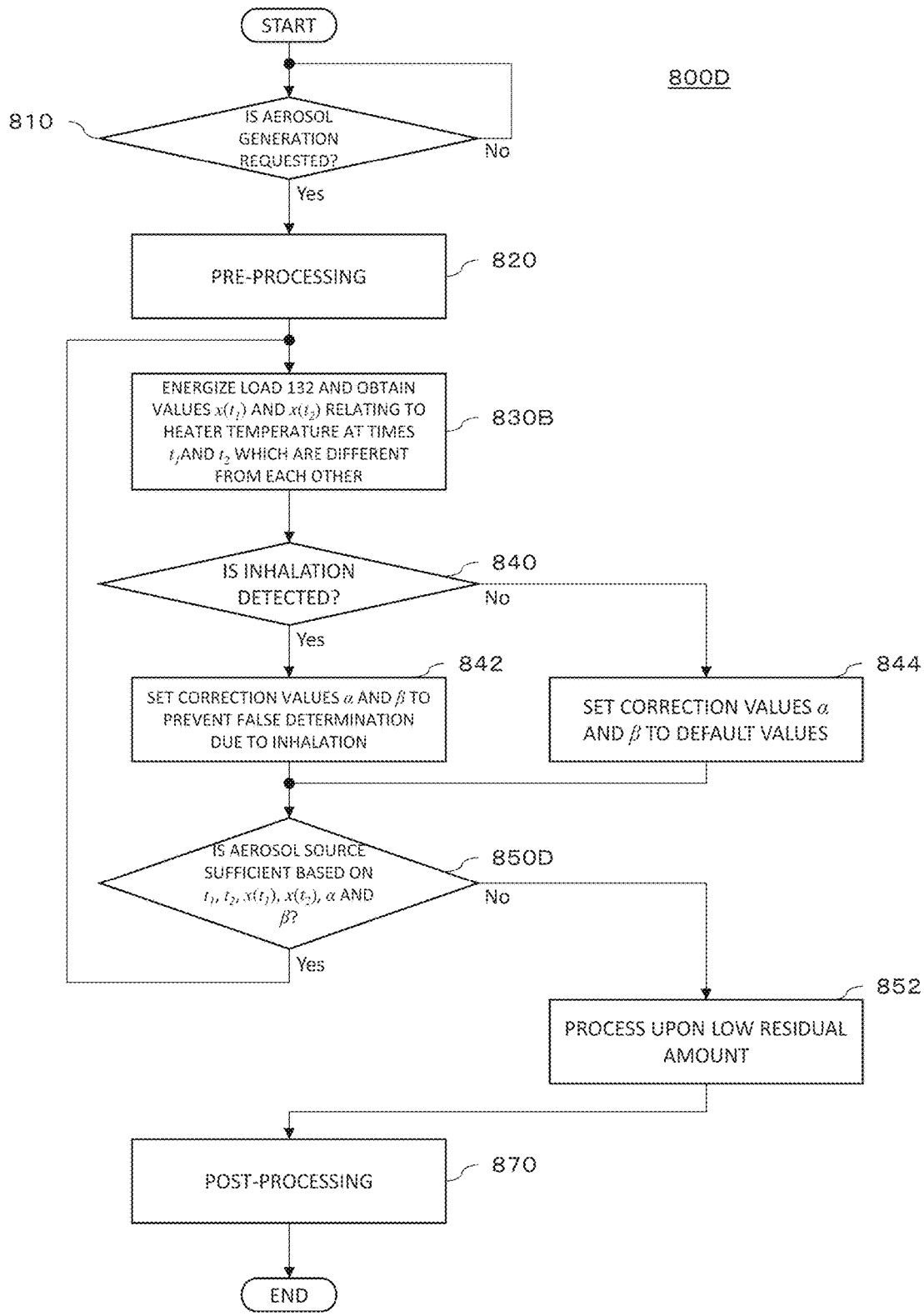

FIG. 8D is a flowchart of yet another exemplary process 800D for determining occurrence of depletion or insufficiency of the aerosol source according to an embodiment of the present disclosure. In the exemplary process 800D, a part of the exemplary process 800B is performed as another process or an interrupt process (described later with respect to FIG. 8I) which is performed in parallel. Accordingly, the exemplary process 800D is suitable for the aerosol inhalator 100 in which the temperature of the load 132 changes according to the inhalation. A part of steps included in the exemplary process 800D is the same as that already described above. Hereinafter, the steps included in the exemplary process 800D which are not described above will be described.

A reference numeral 850D denotes a step of determining whether the aerosol source is sufficient based on the times $t_1$ and $t_2$, values $x(t_1)$ and $x(t_2)$ relating to the heater temperature, and the correction values α and β. Although the content of the process in step 850D is the same as that in step 850B, the branch from step 850D is different from that from step 850B. That is, when it is determined that the aerosol source is sufficient, the process returns to step 830B and loops. Otherwise, the process proceeds to step 852.

Figure 8E:
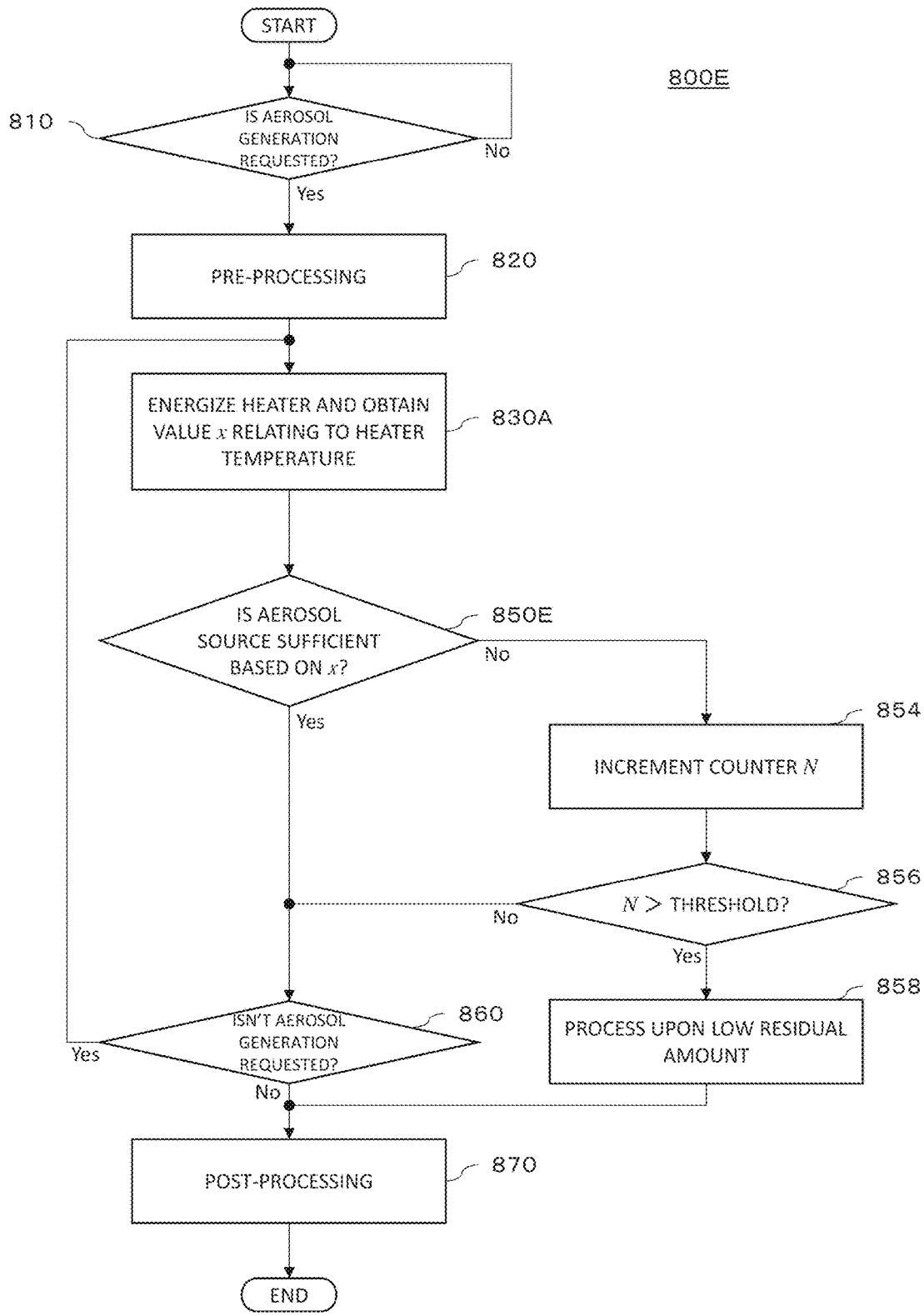

FIG. 8E is a flowchart of an exemplary process 800E for determining occurrence of depletion or insufficiency of the aerosol source according to an embodiment of the present disclosure. The exemplary process 800E is particularly suitable for the aerosol inhalator 100 and the like in which although the temperature of the load 132 is changed due to the inhalation, the magnitude of the change does not depend on the inhalation strength. A part of steps included in the exemplary process 800E is the same as that already described above. Hereinafter, the steps included in the exemplary process 800E which are not described above will be described.

A reference numeral 850E denotes a step of determining whether the aerosol source is sufficient based on the values x relating to the heater temperature. When it is determined that the aerosol source is sufficient, the process proceeds to step 860, otherwise, the process proceeds to step 854.

Reference numerals 854 and 856 denote a step of incrementing a counter N, for example, by 1, and a step of determining whether the counter N is larger than a predetermined threshold which is zero or more, respectively. Note that the counter N may be initialized to, for example, zero at the time of shipment of the aerosol inhalator 100. When the counter N is larger than a predetermined threshold, the process proceeds to step 858, otherwise the process proceeds to step 860.

According to steps 854 and 856, when it is determined a predetermined threshold plus one times that the aerosol is not sufficient, the process proceeds to step 858. Note that the predetermined threshold may be the initial value of the counter N, for example, zero. In such a case, when it is determined one time that the aerosol is not sufficient, the process proceeds to step 858. This means that steps 854 and 856 are not necessary in some embodiments.

A reference numeral 858 denotes a step of performing a process upon low residual amount performed when the residual amount of the aerosol is low. This step may be a step in which a step of initializing the counter N which has been described with respect to steps 854 and 856 to step 852 (process upon low residual amount) is added.

The exemplary processes 800A to 800D each include steps 840, 842, and 844, whereas the exemplary process 800E does not include these steps. That is, in the exemplary processes 800A to 800D, at least one of a threshold used in each of steps 850A, 850B, 850C and 850D of determining whether the aerosol source is sufficient and a variable (value) used to compare with the threshold is corrected according to the presence or absence of the inhalation. On the other hand, in the exemplary process 800E, a threshold used in step 850E corresponding to these steps and a variable (value) used to compare with the threshold are not corrected regardless of the presence or absence of the inhalation. In other words, in the exemplary process 800E, it is determined whether the aerosol source is sufficient by comparing the threshold which is the same value at the time of both of inhaling and non-inhaling with the variable (value) which is different between at the time of inhaling and at the time of non-inhaling.

In this way, in the exemplary process 800E, it can be determined whether the aerosol source is sufficient, even when the threshold and the variable (value) to be compared with the threshold are not corrected according to the presence or absence of the inhalation. A method of setting the threshold enabling such a determination will be described later.

Note that, as described later, the exemplary process 800E can be also used for the aerosol inhalator 100 and the like in which the magnitude of the change in temperature of the load 132 due to the inhalation depends on the inhalation strength.

Figure 8F:
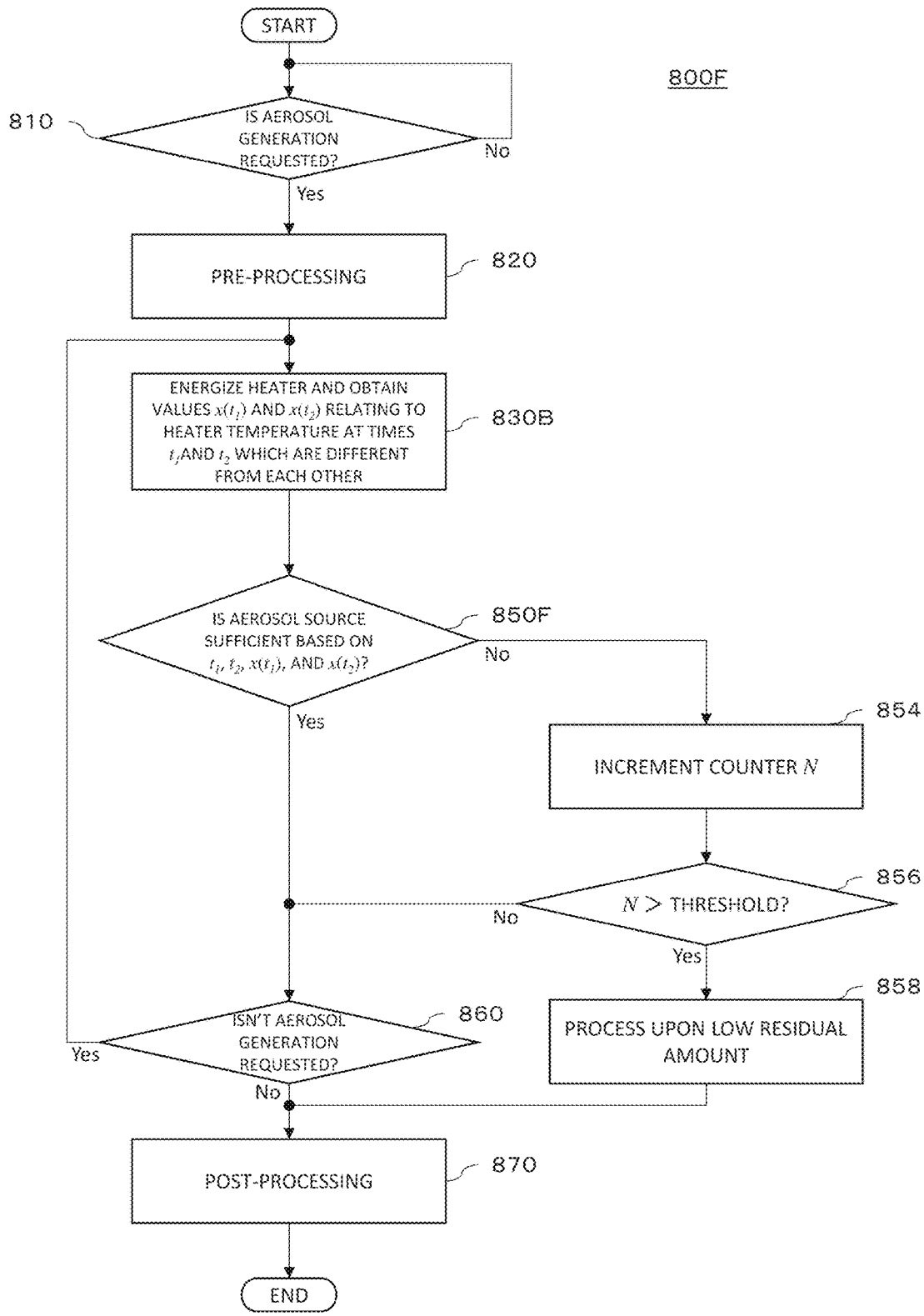

FIG. 8F is a flowchart of an exemplary process 800F for determining occurrence of depletion or insufficiency of the aerosol source according to an embodiment of the present disclosure. The exemplary process 800F is particularly suitable for the aerosol inhalator 100 and the like in which although the temperature change of the load 132 per a predetermined time period is changed due to the inhalation, the magnitude of the change does not depend on the inhalation strength. A part of steps included in the exemplary process 800F is the same as that already described above. Hereinafter, the steps included in the exemplary process 800F which are not described above will be described.

A reference numeral 850F denotes a step of determining whether the aerosol source is sufficient based on the times $t_1$ and $t_2$, and values $x(t_1)$ and $x(t_2)$ relating to the heater temperature. When it is determined that the aerosol source is sufficient, the process proceeds to step 860, otherwise the process proceeds to step 854.

Similar to the exemplary process 800E, in the exemplary process 800F, it can be determined whether the aerosol source is sufficient, even when the threshold and the variable (value) to be compared with the threshold are not corrected according to the presence or absence of the inhalation. A method of setting the threshold enabling such a determination will be described later.

Note that, as described later, the exemplary process 800F can be also used for the aerosol inhalator 100 and the like in which the magnitude of the change in temperature of the load 132 due to the inhalation depends on the inhalation strength.

Figure 8G:
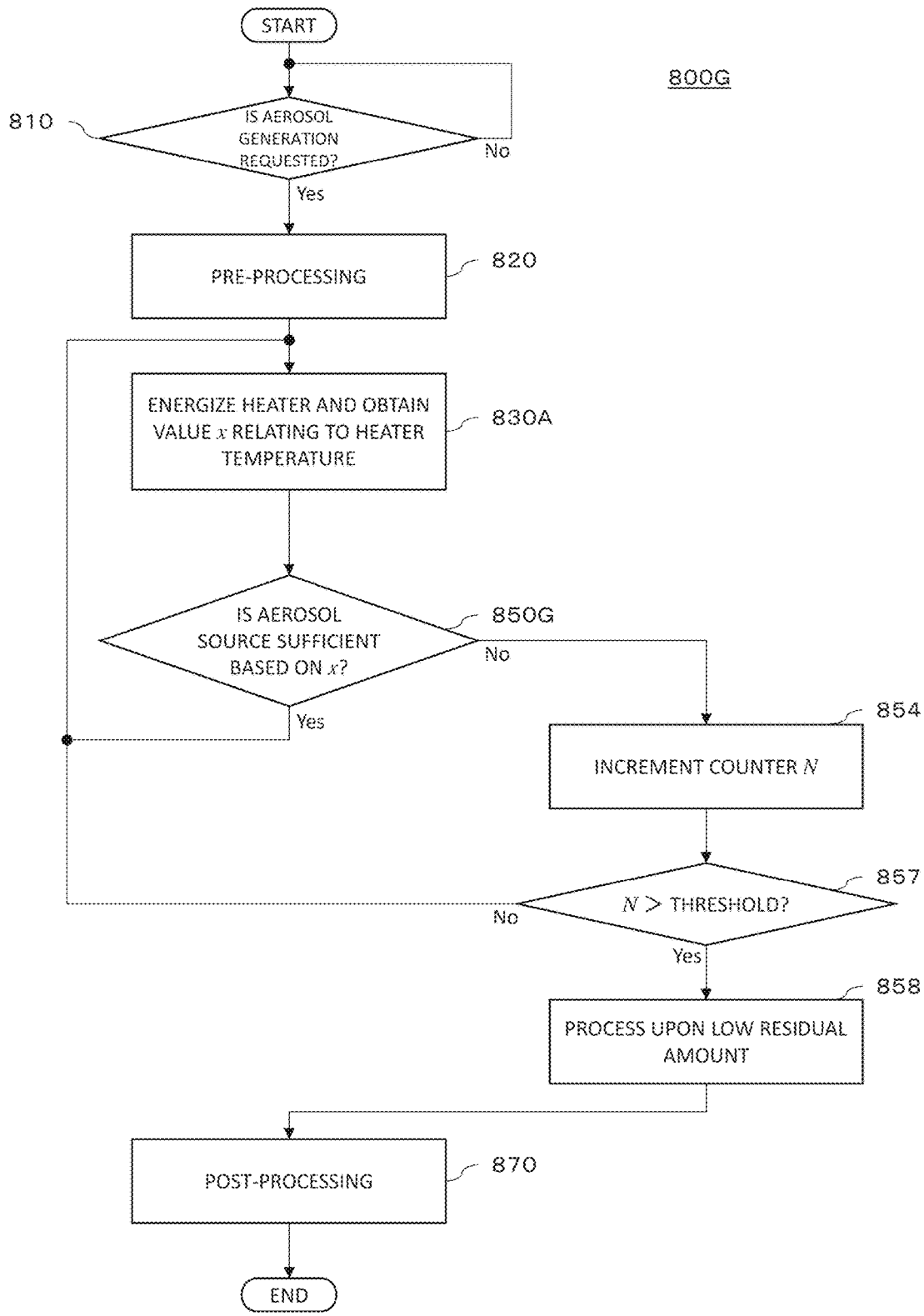

FIG. 8G is a flowchart of yet another exemplary process 800G for determining occurrence of depletion or insufficiency of the aerosol source according to an embodiment of the present disclosure. In the exemplary process 800G, a part of the exemplary process 800E is performed as another process or an interrupt process (described later with respect to FIG. 8I) which is performed in parallel. Accordingly, the exemplary process 800G is particularly suitable for the aerosol inhalator 100 and the like in which although the temperature change of the load 132 is changed due to the inhalation, the magnitude of the change does not depend on the inhalation strength. A part of steps included in the exemplary process 800G is the same as that already described above. Hereinafter, the steps included in the exemplary process 800G which are not described above will be described.

A reference numeral 850G denotes a step of determining whether the aerosol source is sufficient based on the values x relating to the heater temperature. Although the content of the process in step 850G is the same as that in step 850E, the branch from step 850G is different from that from step 850E. That is, when it is determined that the aerosol source is sufficient, the process returns to step 830A and loops. Otherwise, the process proceeds to step 854.

A reference numeral 857 denotes a step of determining whether the counter N is larger than a predetermined threshold. Although the content of the process in step 857 is the same as that in step 856, the branch from step 857 is different from that from step 856. That is, when it is determined that the counter N is larger than a predetermined threshold, the process proceeds to step 858, otherwise, the process returns to step 830A and loops.

Similar to the exemplary processes 800E and 800F, in the exemplary process 800G, it can be determined whether the aerosol source is sufficient, even when the threshold and the variable (value) to be compared with the threshold are not corrected according to the presence or absence of the inhalation. A method of setting the threshold enabling such a determination will be described later.

Note that, as described later, the exemplary process 800G can be also used for the aerosol inhalator 100 and the like in which the magnitude of the change in temperature of the load 132 due to the inhalation depends on the inhalation strength.

Figure 8H:
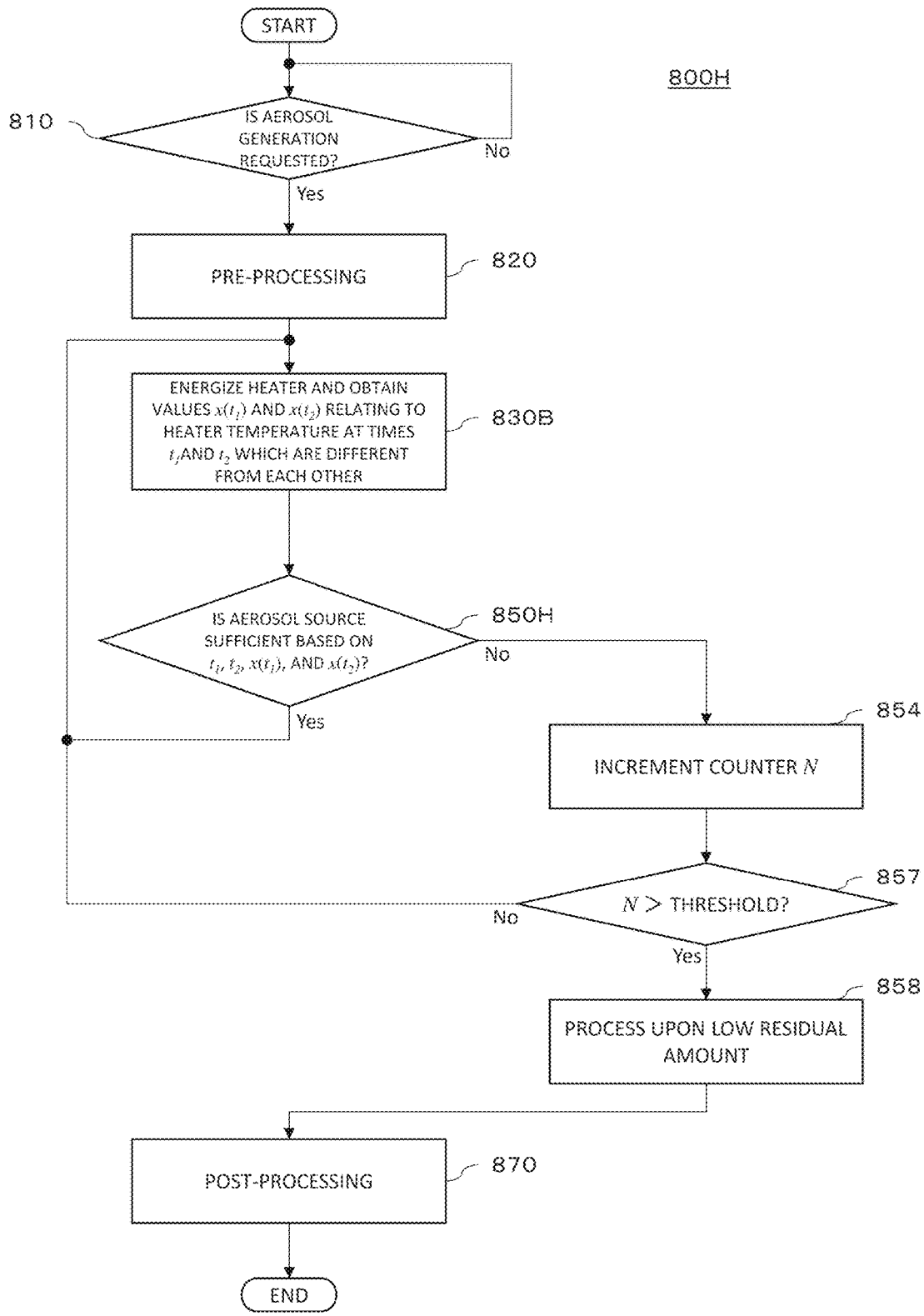

FIG. 8H is a flowchart of still another exemplary process 800H for determining occurrence of depletion or insufficiency of the aerosol source according to an embodiment of the present disclosure. In the exemplary process 800H, a part of the exemplary process 800F is performed as another process or an interrupt process (described later with respect to FIG. 8I) which is performed in parallel. Accordingly, the exemplary process 800H is particularly suitable for the aerosol inhalator 100 and the like in which although the temperature change of the load 132 per a predetermined time period is changed due to the inhalation, the magnitude of the change does not depend on the inhalation strength. Since a part of steps included in the exemplary process 800H has been already been described above, hereinafter, the steps included in the exemplary process 800H which are not described above will be described.

A reference numeral 850H denotes a step of determining whether the aerosol source is sufficient based on the times $t_1$ and $t_2$, and values $x(t_1)$ and $x(t_2)$ relating to the heater temperature. Although the content of the process in step 850H is the same as that in step 850F, the branch from step 850H is different from that from step 850F. That is, when it is determined that the aerosol source is sufficient, the process returns to step 830B and loops. Otherwise, the process proceeds to step 854.

Similar to the exemplary processes 800E, 800F, and 800G, in the exemplary process 800H, it can be determined whether the aerosol source is sufficient, even when the threshold and the variable (value) to be compared with the threshold are not corrected according to the presence or absence of the inhalation. Note that a method of setting the threshold enabling such a determination will be described later.

Note that, as described later, the exemplary process 800H can be also used for the aerosol inhalator 100 and the like in which the magnitude of the change in temperature of the load 132 due to the inhalation depends on the inhalation strength.

Figure 8I:
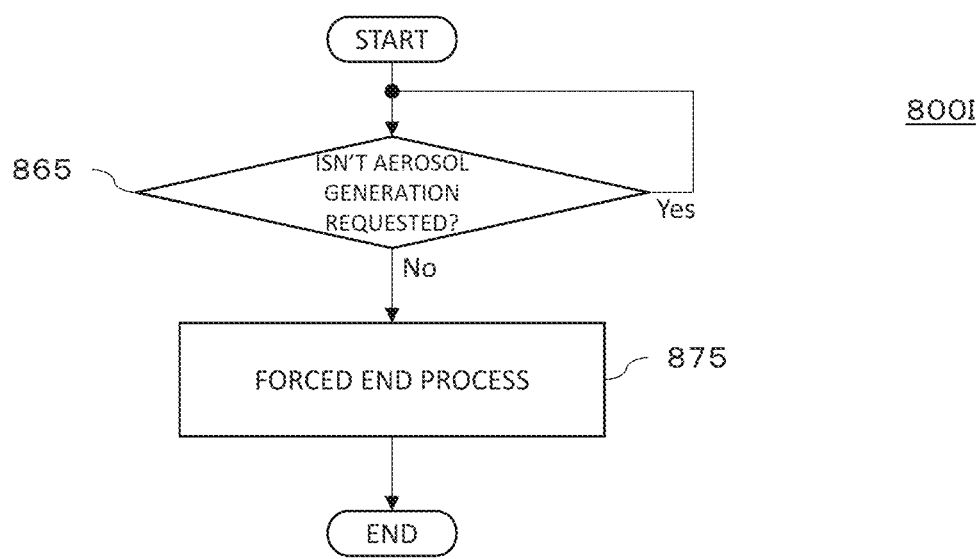

FIG. 8I is a flowchart of an exemplary process 800I for ending (forcibly ending) the exemplary processes 800C, 800D, 800G, and 800H according to an embodiment of the present disclosure. The exemplary process 800I is performed at the same time as, that is, in parallel with the exemplary processes 800C, 800D, 800G, and 800H.

A reference numeral 865 denotes a step of determining whether the generation of the aerosol is not requested. Although the content of the process in step 865 is the same as that in step 860, the branch from step 865 is different from that from step 860. That is, when it is determined that the generation of the aerosol is not requested, the process returns to step 865, otherwise the process proceeds to step 875.

Step 875 includes a step of ending in progress or forcibly ending the exemplary processes 800C, 800D, 800G, and 800H which are performed in parallel.

Note that the exemplary processes 800C, 800D, 800G, and 800H may be ended not by performing the exemplary process 800I in parallel but by some interruption which is generated when the generation of the aerosol is not requested. In this case, the controller 106 may be configured to enable the interruption before performing the exemplary processes 800C, 800D, 800G or 800H, or step 820, and forcibly end the exemplary process 800C, 800D, 800G or 800H with the interruption as a trigger, and turn off the switches Q1 and Q2 (or only the switch Q1) as described later. Note that the interruption is for purposes of ending the exemplary process 800C, 800D, 800G, or 800H, and therefore after the interruption, the process does not return to the exemplary process 800C, 800D, 800G, or 800H which has been performed (the exemplary process 800C, 800D, 800G, or 800H is not newly started).

3-2. Detail of Process

Hereinafter, a more detailed exemplary process to be performed in a part of steps in the exemplary processes 800A to 800I will be described.

3-2-1. Regarding Step 830A

Figure 9A:
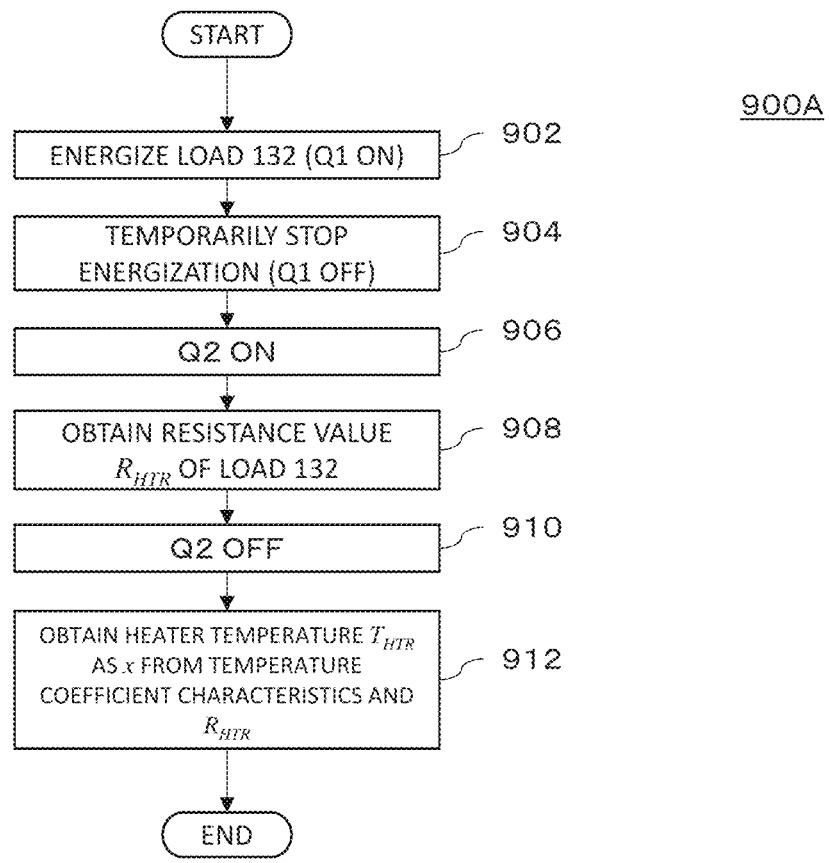

FIG. 9A is a flowchart of a more specific exemplary process 900A which is performed in step 830A in the exemplary process 800A, 800C, 800E or 800G (hereinafter, referred to as the "exemplary process 800A or the like").

A reference numeral 902 denotes a step of turning on the switch Q1. When this step is performed, the current flows in the load 132 via the switch Q1, and the load 132 generates heat.

Reference numerals 904 and 906 denote a step of turning off the switch Q1 and a step of turning on the switch Q2, respectively. When this step is performed, the current flows in the shunt resistor 212 and the load 132 via the switch Q2.

Reference numeral 908 denotes a step of obtaining the resistance value $R_{HTR}$ of the load 132. This step can include a step of calculating the resistance value $R_{HTR}$ of the load 132 using the output value from one or both of the sensors 112B and 112D, for example.

A reference numeral 910 denotes a step of turning off the switch Q2.

A reference numeral 912 denotes a step of obtaining the temperature $T_{HTR}$ of the load 132, as the value x relating to the heater temperature, from the temperature coefficient characteristics of the load 132 and the obtained resistance value $R_{HTR}$ of the load 132.

Note that, in step 908, the voltage value itself applied to the load 132 or the shunt resistor 212 may be obtained, instead of the resistance value $R_{HTR}$ of the load 132. Note that, in this case, in step 912, the temperature $T_{HTR}$ of the load 132 is obtained, as the value x relating to the heater temperature, from the temperature coefficient characteristics of the load 132, and the obtained voltage value applied to the load 132 or the shunt resistor.

Note that when the exemplary process 900A is performed, steps 820 (pre-processing) and 870 (post-processing) in the exemplary process 800A and the like are not necessary. In addition, when the exemplary process 900A is performed, step 875 (forced end process) in the exemplary process 9001 can further include a step of turning off the switches Q1 and Q2 regardless of the states of the switches.

3-2-2. Regarding Step 830B

Figure 9B:
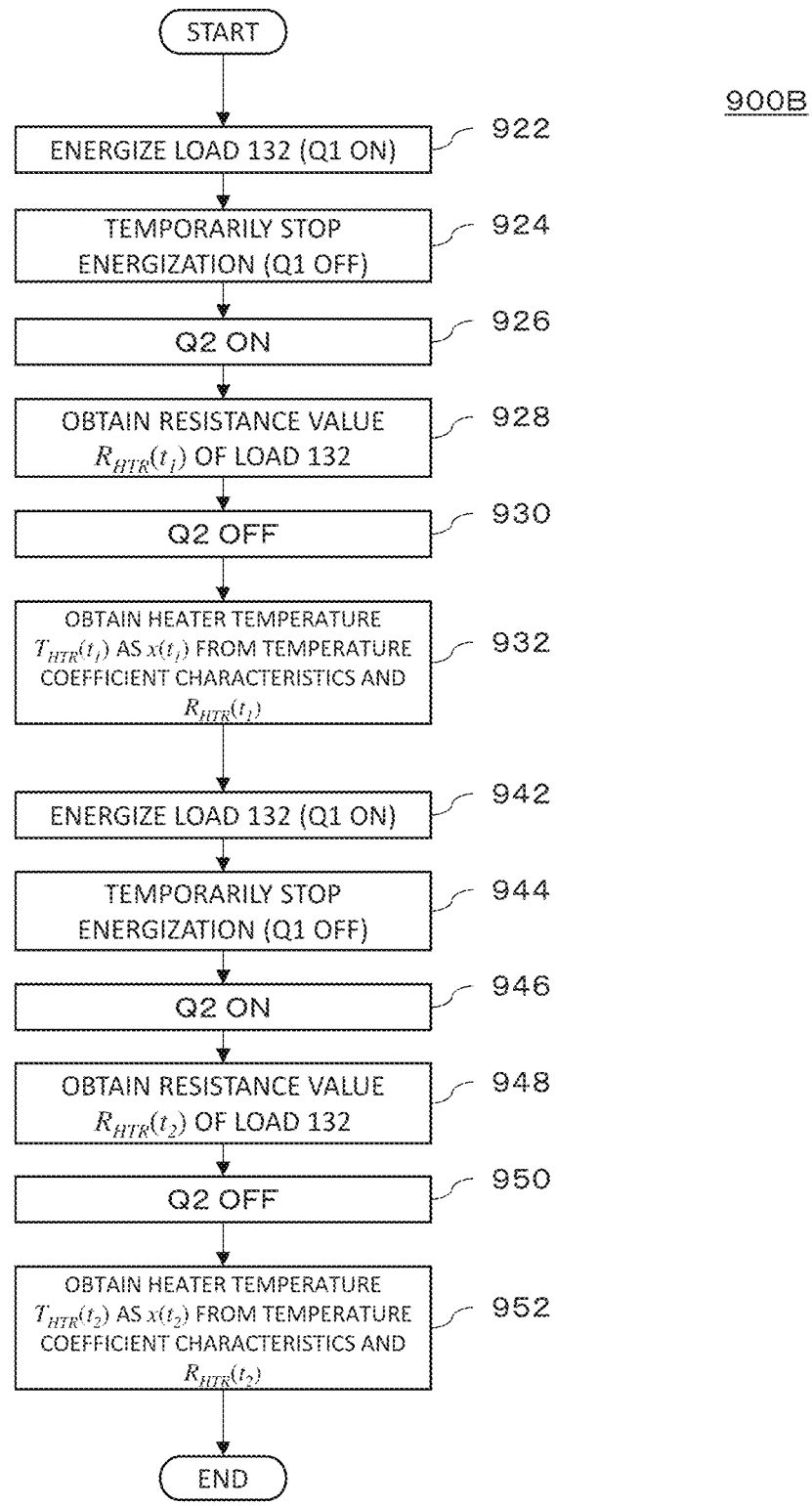

FIG. 9B is a flowchart of a more specific exemplary process 900B which is performed in step 830B in the exemplary process 800B, 800D, 800F or 800H (hereinafter, referred to as the "exemplary process 800B or the like").

A reference numeral 922 denotes a step of turning on the switch Q1. When this step is performed, the current flows in the load 132 via the switch Q1, and the load 132 generates heat.

Reference numerals 924 and 926 denote a step of turning off the switch Q1 and a step of turning on the switch Q2, respectively. When this step is performed, the current flows in the shunt resistor 212 and the load 132 via the switch Q2.

Reference numeral 928 denotes a step of obtaining the resistance value of the load 132. This step can include a step of calculating the resistance value of the load 132 using the output value from one or both of the sensors 112B and 112D, for example. Here, in step 928, a point of time when a resistance value of the load 132 is obtained or a point of time when an output value of the sensor for obtaining the resistance value is represented as $t_1$, and the resistance value of the load 132 at the time $t_1$ is represented as $R_{HTR}(t_1)$.

A reference numeral 930 denotes a step of turning off the switch Q2.

A reference numeral 932 denotes a step of obtaining the temperature $T_{HTR}(t_1)$ of the load 132 at the time $t_1$, as the value $x(t_1)$ relating to the heater temperature at the time $t_1$, from the temperature coefficient characteristics of the load 132 and the obtained resistance value $R_{HTR}(t_1)$ of the load 132. Note that step 932 may be performed at the same time as step 930, or may be performed at an arbitrary timing after step 928 and before step 952.

Reference numerals 942 to 952 are the same as steps 922 to 932, respectively, except the respective steps are performed not at time $t_1$ but at time $t_2$.

Note that when the exemplary process 900B is performed, step 820 (pre-processing) in the exemplary process 800B or the like can include step of activating a timer for determining the time $t_1$ and $t_2$, while step 870 (post-processing) is not necessary. In addition, when the exemplary process 900B is performed, step 875 (forced end process) in the exemplary process 9001 can further include a step of turning off the switches Q1 and Q2 regardless of the states of the switches.

Note that, in step 928 and step 948, the voltage value itself applied to the load 132 or the shunt resistor 212 may be obtained, instead of the resistance value $R_{HTR}$ of the load 132. Note that, in this case, in step 932 and step 952, the temperature $T_{HTR}$ of the load 132 is obtained, as the value x relating to the heater temperature, from the temperature coefficient characteristics of the load 132, and the obtained voltage value applied to the load 132 or the shunt resistor.

Figure 9C:
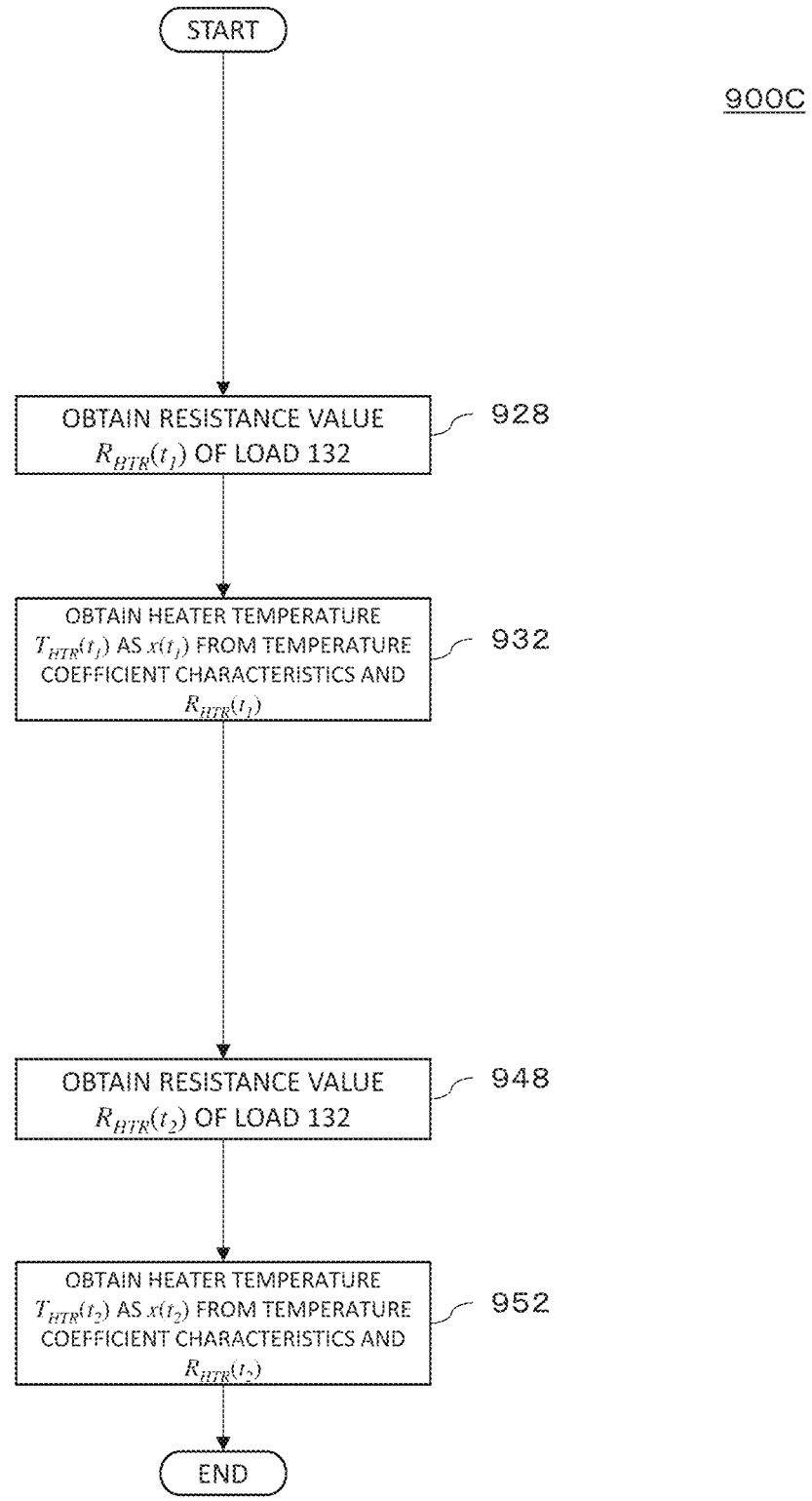

FIG. 9C is a flowchart of a more specific another exemplary process 900C which is performed in step 830B in the exemplary process 800B or the like. The exemplary process 900C corresponds to a process in which steps 922 to 926, 930, 934 to 946, and 950 are excluded from the exemplary process 900B. The exemplary process 900C is suitable for a circuit configuration having only the second circuit 204, instead of the circuit configuration in which the first circuit 202 and the second circuit 204 illustrated in FIG. 2 are connected in parallel.

Note that when the exemplary process 900C is performed, step 820 (pre-processing) in the exemplary process 800B or the like can include step of activating a timer for determining the time $t_1$ and $t_2$, and a step of turning on the switch Q1, and step 870 (post-processing) can include a step of turning off the switch Q1. In addition, when the exemplary process 900C is performed, step 875 (forced end process) in the exemplary process 800I can further include a step of turning off the switch Q1 regardless of the states of the switch.

Note that, in step 928 and step 948, the voltage value itself applied to the load 132 or the shunt resistor 212 may be obtained, instead of the resistance value $R_{HTR}$ of the load 132. Note that, in this case, in step 932 and step 952, the temperature $T_{HTR}$ of the load 132 is obtained, as the value x relating to the heater temperature, from the temperature coefficient characteristics of the load 132, and the obtained voltage value applied to the load 132 or the shunt resistor.

Figure 9D:
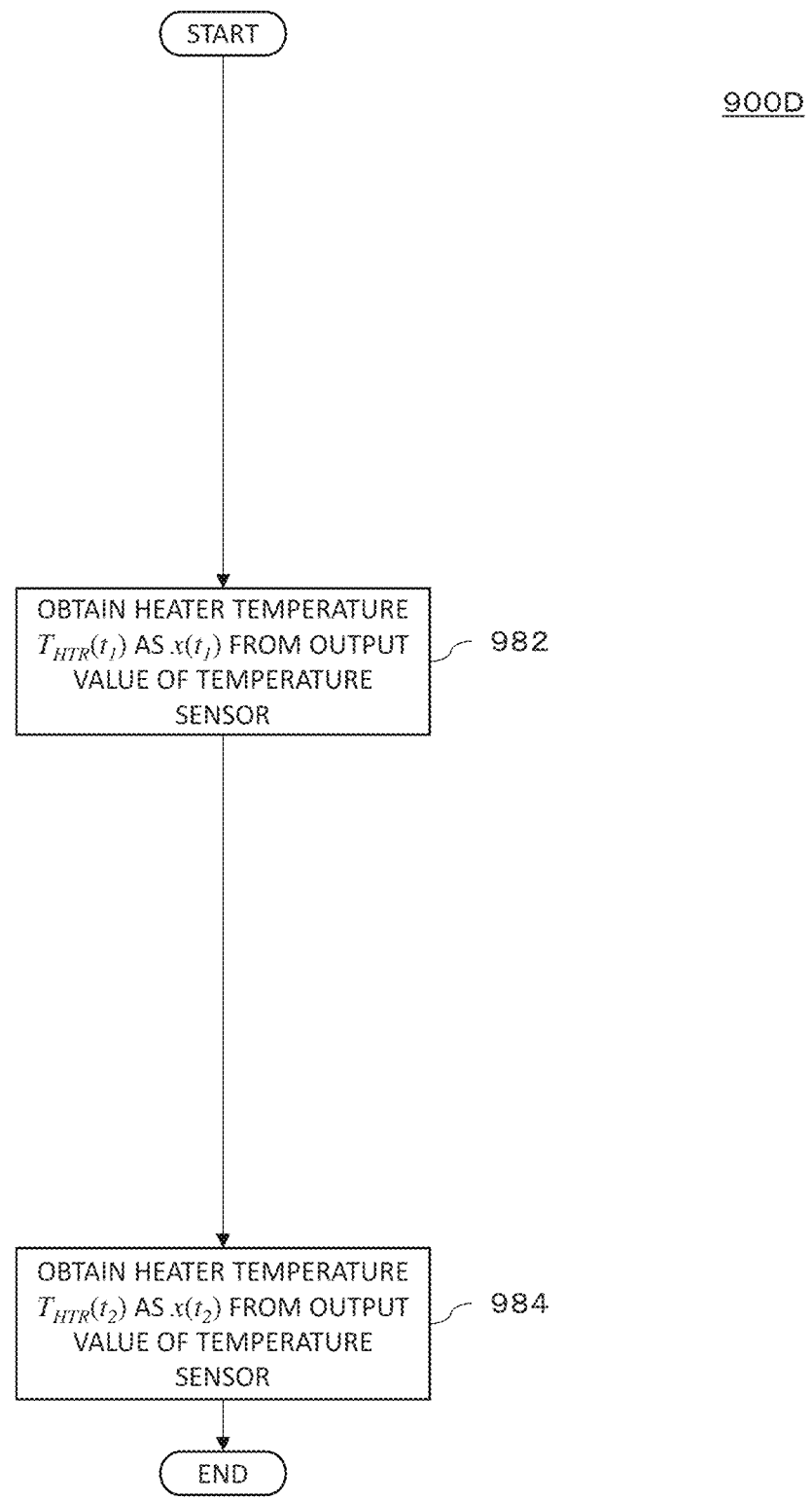

FIG. 9D is a flowchart of a more specific yet another exemplary process 900D which is performed in step 830B in the exemplary process 800B or the like. The exemplary process 900D is suitable for a circuit configuration having the temperature sensor 112 which outputs the temperature of the load 132, instead of the circuit configuration having the voltage sensors 112B and 112D illustrated in FIG. 2.

A reference numeral 982 denotes a step of obtaining the heater temperature $T_{HTR}(t_1)$ at the time $t_1$, as the value $x(t_1)$ relating to the heater temperature at the time $t_1$, based on the output value of the temperature sensor which measures the temperature of the load 132.

A reference numeral 984 is the same as step 982, except the step is performed not at time $t_1$ but at time $t_2$.

Note that when the exemplary process 900D is performed, step 820 (pre-processing) in the exemplary process 800B or the like can include step of activating a timer for determining the time $t_1$ and $t_2$, and a step of turning on the switch Q1, and step 370 (post-processing) can include a step of turning off the switch Q1. In addition, when the exemplary process 900D is performed, step 875 (forced end process) in the exemplary process 800I can include a step of turning off the switch Q1 regardless of the states of the switch.

3-2-3. Regarding Steps 850A and 850C (Hereinafter, Referred to as the "Step 850A or the Like")

3-2-3-1. Regarding Overview of Determination

In step 850A or the like, when a predetermined inequality, which is a function of the value x relating to the heater temperature and the correction values α and β, is satisfied, it can be determined that the aerosol source is sufficient, and when the inequality is not satisfied, it can be determined that the aerosol source is not sufficient. Such an inequality depends on whether the value x relating to the heater temperature is increased or decreased when the temperature of the load 132 is increased, and whether the temperature reached by the load 132 is increased or decreased as described above with respect to graphs 500, 600 and 700 due to the inhalation. In the description below, it is assumed that the value x relating to the heater temperature is a value of the temperature of the load 132, and the value x relating to the heater temperature is increased when the temperature of the load 132 is increased.

As described above, it can be determined whether the residual amount of the aerosol source in the retainer and the like is sufficient by comparing the temperature of the load 132 with the temperature threshold $T'_{thre}(v)$. This comparison can be represented by the following inequality (11).

[Formula 8]

$$x \leq T'_{thre}(v) \tag{11}$$

Here, the temperature threshold which can be obtained by an experiment and set without taking into consideration the inhaling by the user on the aerosol inhalator 100 is represented as $T_{thre}$ (equal to or higher than the boiling point $T_{B.P.}$ or the like of the aerosol source and equal to or lower than the equilibrium temperature $T_{equi.}$), and the correction values which may be positive, zero, or negative value are represented as α and β.

$$T'_{thre}(v) = T_{thre} + \alpha + \beta \quad \text{[Formula 9]}$$

Using the above expression, the inequality (11) can be rearranged to the following inequality (12).

[Formula 10]

$$x \leq T_{Thre} + \alpha + \beta$$

$$x - \alpha \leq T_{thre} + \beta \tag{12}$$

Accordingly, in step 850A and the like, it can be determined whether the inequality (11) or (12) is satisfied. That is, it may be determined that the aerosol source is sufficient when the inequality (12) holds, and it may be determined that the aerosol source is depleted or insufficient when the inequality (12) does not hold. Note that these inequality signs in these inequalities may be "<."

Note that "x−α" in the inequality (12) is obtained by correcting the value x relating to the heater temperature. In addition, "$T_{thre}+\beta$" in the inequality (12) is obtained by correcting the threshold $T_{thre}$. In other words, a has an effect of correcting the value x relating to the heater temperature, and β has an effect of correcting the threshold $T_{thre}$.

The step 850A and the like are repeatedly performed. Accordingly, note that each of the step 850A and the like is an example of a step of correcting a value relating to the heater temperature or a time-series change in a value relating to the heater temperature.

3-2-3-2. Regarding Parameter Used for Determination

When the temperature reached by the load 132 is increased as the inhalation strength relative to the aerosol inhalator 100 is increased, the temperature threshold $T'_{thre}(v)$ may be $T'_{satmax}(v)$ or more and $T_{equi.}$ or less, or $T'_{satmax}(v)$ or more and $T'_{depmax}(v)$ or less, as described above. This condition can be represented by the following inequality (13) or (14).

[Formula 11]

$$T'_{satmax}(v) \leq T'_{thre}(v) \leq T_{equi.}$$

$$T'_{satmax}(v) \leq T_{thre} + \alpha + \beta \leq T_{equi.}$$

$$T'_{satmax}(v) - T_{thre} \leq \alpha + \beta \leq T_{equi.} - T_{thre} \quad (13)$$

$$T'_{satmax}(v) \leq T'_{thre}(v) \leq T'_{depmax}(v)$$

$$T'_{satmax}(v) \leq T_{thre} + \alpha + \beta \leq T'_{depmax}(v)$$

$$T'_{satmax}(v) - T_{thre} \leq \alpha + \beta \leq T'_{depmax}(v) - T_{thre} \quad (14)$$

Accordingly, the correction values α and β can satisfy the inequality (13) or (14). More specifically, the correction values α and β can be represented as α=0 and β=Δ(v), α=Δ(v) and β=0, or α=Δ'(v) and β=Δ"(v), where Δ(v) is the predetermined linear or non-linear function which satisfies the following inequality (15) or (16), and Δ'(v) and Δ"(v) each are the predetermined linear or non-linear function which satisfies the following inequality (17) or (18).

[Formula 12]

$$T'_{satmax}(v) - T_{thre} \leq \Delta(v) \leq T_{equi.} - T_{thre} \quad (15)$$

$$T'_{satmax}(v) - T_{thre} \leq \Delta(v) \leq T'_{depmax}(v) - T_{thre} \quad (16)$$

$$T'_{satmax}(v) - T_{thre} \leq \Delta'(v) + \Delta''(v) \leq T_{equi.} - T_{thre} \quad (17)$$

$$T'_{satmax}(v) - T_{thre} \leq \Delta'(v) + \Delta''(v) \leq T'_{depmax}(v) - T_{thre} \quad (18)$$

In another aspect, when the temperature reached by the load 132 is increased as the inhalation strength relative to the aerosol inhalator 100 is increased, the temperature threshold $T'_{thre}(v)$ may be $T_{thre} + \varepsilon_1(v)$ as described above. Accordingly, Δ(v), Δ'(v), and Δ"(v) each may be a function which satisfies the following expressions.

$$\Delta(v) = \varepsilon_1(v)$$

$$\Delta'(v) + \Delta''(v) = \varepsilon_1(v) \quad \text{[Formula 13]}$$

In addition, when the temperature reached by the load 132 is decreased as the inhalation strength relative to the aerosol inhalator 100 is increased, the temperature threshold $T'_{thre}(v)$ may be $T_{B.P.}$ or more and $T As described above, it can be determined whether the residual amount of the aerosol source in the retainer and the like is sufficient by comparing the temperature change of the load 132 per a predetermined time period Δt with the temperature change threshold $\Delta T'_{thre}(v)$. However, as described above, the magnitude of the temperature change of the load 132 changes depending on the length of the predetermined time period Δt. Accordingly, it is preferred to use, for this comparison, a value of a ratio between the change amount of the heater temperature over time and the length of the time elapsed, for example, a rate of temperature change of the load 132.

Specifically, this comparison can be represented by the following inequality (25).

[Formula 19]

$$\frac{x(t_2) - x(t_1)}{t_2 - t_1} \leq Thre_1(v) \quad (25)$$

Here, the threshold which can be obtained by an experiment, and can be used for determining whether the residual amount of the aerosol source is sufficient without taking into consideration the inhaling on the aerosol inhalator 100 is represented as $Thre_1$ (corresponding to $\Delta T_{thre}/\Delta t$ in FIG. 3. $\Delta T_{thre}$ is $\Delta T_{sat}$ or more and $\Delta T_{dep}$ or less), and the correction values which may be positive, zero, or negative value are represented as α and β.

$$Thre'_1(v) = Thre_1 + \alpha + \beta \quad \text{[Formula 18]}$$

Using the above expression, the inequality (25) can be rearranged to the following inequality (26).

[Formula 19]

$$\frac{x(t_2) - x(t_1)}{t_2 - t_1} \leq Thre_1 + \alpha + \beta \quad (26)$$

$$\frac{x(t_2) - x(t_1)}{t_2 - t_1} - \alpha \leq Thre_1 + \beta$$

Note that the left side of the inequality (26) is obtained by correcting the temperature change of the load 132 per a predetermined time period Δt or the rate of temperature change of the load 132. In addition, $Thre_1+\beta$ in the inequality (26) is obtained by correcting the threshold $\Delta T_{thre}$ or $Thre_1$. In other words, a has an effect of correcting the temperature change of the load 132 per a predetermined time period Δt or the rate of temperature change of the load 132, and β has an effect of correcting the threshold $\Delta T_{thre}$ or $Thre_1$.

In addition, as described above, it can be determined whether the residual amount of the aerosol source in the retainer and the like is sufficient by comparing the temperature change of the load 132 per a predetermined amount of electric power ΔW with the temperature change threshold $\Delta T'_{thre}(v)$. However, similarly, the magnitude of the temperature change of the load 132 changes depending on the magnitude of the predetermined amount of electric power ΔW. Accordingly, it is preferred to use, for this comparison, a value of a ratio between a change amount of the value relating to the heater temperature due to power supply to the load 132 and an amount of electric power supplied to the load 132 (hereinafter, referred to as the "rate of the temperature change" for the sake of convenience, similar to a value of a ratio between the change amount of the heater temperature over time and the length of the time elapsed).

Specifically, this comparison can be represented by the following inequality (27), when the threshold which can be obtained by an experiment, and can be used for determining whether the residual amount of the aerosol source is sufficient without taking into consideration the inhaling by the user on the aerosol inhalator 100 is represented as $Thre_2$ (corresponding to $\Delta T_{thre}/\Delta W$ in FIG. 3), the correction values which may be positive, zero, or negative value are represented as α and β, $Thre'_2 = Thre_2 + \alpha + \beta$, and the electric power supplied to the load 132 at the time t is represented as P(t).

[Formula 20]

$$\frac{x(t_2) - x(t_1)}{\int_{t_1}^{t_2} P(t)dt} \leq Thre'_2 \quad (27)$$

$$\frac{x(t_2) - x(t_1)}{\int_{t_1}^{t_2} P(t)dt} - \alpha \leq Thre_2 + \beta \quad (28)$$

Note that the left side of the inequality (26) is obtained by correcting the temperature change of the load 132 per a predetermined amount of electric power ΔW or the rate of temperature change of the load 132. In addition, $Thre_2+\beta$ in the inequality (26) is obtained by correcting the threshold $\Delta T_{thre}$ or $Thre_2$. In other words, a has an effect of correcting the temperature change of the load 132 per a predetermined amount of electric power ΔW or the rate of temperature change of the load 132, and β has an effect of correcting the threshold $\Delta T_{thre}$ or $Thre_2$.

Accordingly, in step 850B and the like, it can be determined whether any one of the inequalities (25) to (28) is satisfied. That is, it may be determined that the aerosol source is sufficient when the inequality (26) or (28) holds, and it may be determined that the aerosol source is depleted or insufficient when the inequality (26) or (28) does not hold. Note that when the inequality (27) or (28) is used, rather than determining the time $t_2$ as the time $t_1$+a predetermined time period Δt, the controller 106 may monitor the total amount of electric power supplied to the load 132 from the time $t_1$ and determine, as the time $t_2$, the point of time when the total amount of electric power becomes a predetermined amount of electric power. In addition, these inequality signs in these inequalities may be "<."

3-2-4-2. Regarding Parameter Used for Determination

Hereinafter, it is assumed that the inequality (26) is used in step 850B and the like.

When the temperature change of the load 132 per a predetermined time period Δt is increased as the inhalation strength relative to the aerosol inhalator 100 is increased, the temperature change threshold $\Delta T'_{thre}(v)$ may be $\Delta T'_{sat}(v)$ or more and $\Delta T_{dep}$ or less, or $\Delta T'_{sat}(v)$ or more and $\Delta T'_{dep}(v)$ or less, as described above. This condition can be represented by the following inequality (29) or (30).

[Formula 21]

$$\frac{\Delta T'_{sat}(v)}{\Delta t} \leq Thre'_1(v) \leq \frac{\Delta T_{dep}}{\Delta t} \quad (29)$$

$$\frac{\Delta T'_{sat}(v)}{\Delta t} \leq Thre_1 + \alpha + \beta \leq \frac{\Delta T_{dep}}{\Delta t}$$

-continued $$\frac{\Delta T'_{sat}(v)}{\Delta t} - Thre_1 \leq \alpha + \beta \leq \frac{\Delta T_{dep}}{\Delta t} - Thre_1$$

$$\frac{\Delta T'_{sat}(v)}{\Delta t} \leq Thre'_1(v) \leq \frac{\Delta T'_{dep}(v)}{\Delta t} \tag{30}$$

$$\frac{\Delta T'_{sat}(v)}{\Delta t} \leq Thre_1 + \alpha + \beta \leq \frac{\Delta T'_{dep}(v)}{\Delta t}$$

$$\frac{\Delta T'_{sat}(v)}{\Delta t} - Thre_1 \leq \alpha + \beta \leq \frac{\Delta T'_{dep}(v)}{\Delta t} - Thre_1$$

Accordingly, the correction values $\alpha$ and $\beta$ can satisfy the inequality (29) or (30). More specifically, the correction values $\alpha$ and $\beta$ can be represented as $\alpha=0$ and $\beta=\Delta(v)$, $\alpha=\Delta(v)$ and $\beta=0$, or $\alpha=\Delta'(v)$ and $\beta=\Delta''(v)$, where $\Delta(v)$ is the predetermined function which satisfies the following inequality (31) or (32), and $\Delta'(v)$ and $\Delta''(v)$ each are the predetermined function which satisfies the following inequality (33) or (34).

[Formula 22]

$$\frac{\Delta T'_{sat}(v)}{\Delta t} - Thre_1 \leq \Delta(v) \leq \frac{\Delta T_{dep}}{\Delta t} - Thre_1 \tag{31}$$

$$\frac{\Delta T'_{sat}(v)}{\Delta t} - Thre_1 \leq \Delta(v) \leq \frac{\Delta T'_{dep}}{\Delta t} - Thre_1 \tag{32}$$

$$\frac{\Delta T'_{sat}(v)}{\Delta t} - Thre_1 \leq \Delta'(v) + \Delta''(v) \leq \frac{\Delta T_{dep}}{\Delta t} - Thre_1 \tag{33}$$

$$\frac{\Delta T'_{sat}(v)}{\Delta t} - Thre_1 \leq \Delta'(v) + \Delta''(v) \leq \frac{\Delta T'_{dep}(v)}{\Delta t} - Thre_1 \tag{34}$$

In another aspect, when the temperature change of the load 132 per a predetermined time period $\Delta t$ is increased as the inhalation strength relative to the aerosol inhalator 100 is increased, the temperature change threshold $\Delta T'_{thre}(v)$ may be $\Delta T_{thre} + \Delta\varepsilon_1(v)$ as described above. Accordingly, $\Delta(v)$, $\Delta'(v)$, and $\Delta''(v)$ each may be a function which satisfies the following expressions.

[Formula 23]

$$\Delta(v) = \frac{\Delta\varepsilon_1(v)}{\Delta t}$$

$$\Delta'(v) + \Delta''(v) = \frac{\Delta\varepsilon_1(v)}{\Delta t}$$

When the temperature change of the load 132 per a predetermined time period $\Delta t$ is decreased as the inhalation strength relative to the aerosol inhalator 100 is increased, the temperature change threshold $\Delta T'_{thre}(v)$ may be $\Delta T_{sat}$ or more and $\Delta T'_{dep}$ or less, or $\Delta T'_{sat}(v)$ or more and $\Delta T'_{dep}(v)$ or less, as described above. This condition can be represented by the following inequality (35) or (36).

[Formula 24]

$$\frac{\Delta T_{sat}}{\Delta t} \leq Thre'_1(v) \leq \frac{\Delta T'_{dep}(v)}{\Delta t} \tag{35}$$

$$\frac{\Delta T_{sat}}{\Delta t} \leq Thre_1 + \alpha + \beta \leq \frac{\Delta T'_{dep}(v)}{\Delta t}$$

$$\frac{\Delta T_{sat}}{\Delta t} - Thre_1 \leq \alpha + \beta \leq \frac{\Delta T'_{dep}(v)}{\Delta t} - Thre_1$$

$$\frac{\Delta T'_{sat}(v)}{\Delta t} \leq Thre'_1(v) \leq \frac{\Delta T'_{dep}(v)}{\Delta t} \tag{36}$$

$$\frac{\Delta T'_{sat}(v)}{\Delta t} \leq Thre_1 + \alpha + \beta \leq \frac{\Delta T'_{dep}(v)}{\Delta t}$$

$$\frac{\Delta T'_{sat}(v)}{\Delta t} - Thre_1 \leq \alpha + \beta \leq \frac{\Delta T'_{dep}(v)}{\Delta t} - Thre_1$$

Accordingly, when the correction values $\alpha$ and $\beta$ are represented by $\Delta(v)$, $\Delta'(v)$ and $\Delta''(v)$ as described above, in this case, $\Delta(v)$ is the predetermined function which satisfies the following inequality (37) or (38), and $\Delta'(v)$ and $\Delta''(v)$ each are the predetermined function which satisfies the following inequality (39) or (40).

[Formula 25]

$$\frac{\Delta T_{sat}}{\Delta t} - Thre_1 \leq \Delta(v) \leq \frac{\Delta T'_{dep}(v)}{\Delta t} - Thre_1 \tag{37}$$

$$\frac{\Delta T'_{sat}(v)}{\Delta t} - Thre_1 \leq \Delta(v) \leq \frac{\Delta T'_{dep}(v)}{\Delta t} - Thre_1 \tag{38}$$

$$\frac{\Delta T_{sat}(v)}{\Delta t} - Thre_1 \leq \Delta'(v) + \Delta''(v) \leq \frac{\Delta T'_{dep}(v)}{\Delta t} - Thre_1 \tag{39}$$

$$\frac{\Delta T'_{sat}(v)}{\Delta t} - Thre_1 \leq \Delta'(v) + \Delta''(v) \leq \frac{\Delta T'_{dep}(v)}{\Delta t} - Thre_1 \tag{40}$$

In another aspect, when the temperature change of the load 132 per a predetermined time period $\Delta t$ is decreased as the inhalation strength relative to the aerosol inhalator 100 is increased, the temperature change threshold $\Delta T'_{thre}(v)$ may be $\Delta T_{thre} - \Delta\varepsilon_2(v)$ as described above. Accordingly, $\Delta(v)$, $\Delta'(v)$, and $\Delta''(v)$ each may be a function which satisfies the following expressions.

[Formula 26]

$$\Delta(v) = \frac{-\Delta\varepsilon_2(v)}{\Delta t}$$

$$\Delta'(v) + \Delta''(y) = -\frac{\Delta\varepsilon_2(v)}{\Delta t}$$

As described above, the correction value $\alpha$ has an effect of correcting the temperature change of the load 132 per a predetermined time period $\Delta t$ or per a predetermined amount of electric power $\Delta W$ or the rate of temperature change of the load 132 (hereinafter, referred to as the "temperature change or the like"), and the correction value $\beta$ has an effect of correcting the threshold $\Delta T_{thre}$, $Thre_1$ or $Thre_2$ (hereinafter, referred to as the "$\Delta T_{thre}$ or the like"). In the case of $\alpha=0$ and $\beta=\Delta(v)$, this means that only the threshold $\Delta T_{thre}$ or the like of the temperature change or the like of the load 132 and the threshold $\Delta T_{thre}$ or the like is corrected. In the case of $\alpha=\Delta(v)$ and $\beta=0$, this means that only the temperature change or the like of the load 132 of the temperature change or the like of the load 132 and the threshold $\Delta T_{thre}$ or the like is corrected. In the case of $\alpha=\Delta'(v)$ and $\beta=\Delta''(v)$, this means that both of the temperature change or the like of the load 132 and the threshold $\Delta T_{thre}$ or the like are corrected.

3-2-4-3. Remarks about Determination

In the above description, although it is assumed that the inequality (26) is used in step 850B or the like, when the inequality (27) or (28) is used in step 850B or the like, Δt of the denominator in the above-described inequality may be replaced with ΔW. In addition, in the above description, although it is assumed that the value x relating to the heater temperature is a value of the temperature of the load, note that when the value x relating to the heater temperature which is not the value of the temperature of the load is used, Δ(v), Δ'(v) and Δ"(v) each may be a function obtained based on such a value x relating to the heater temperature. In particular, note that when the value x relating to the heater temperature is decreased in the case where the temperature of the load 132 is increased, the inequality signs in the inequalities (25) to (28) may be reversed or the like.

3-2-5. Regarding Step 842

3-2-5-1. When Inhalation Strength is Taken into Consideration

Figure 10A:
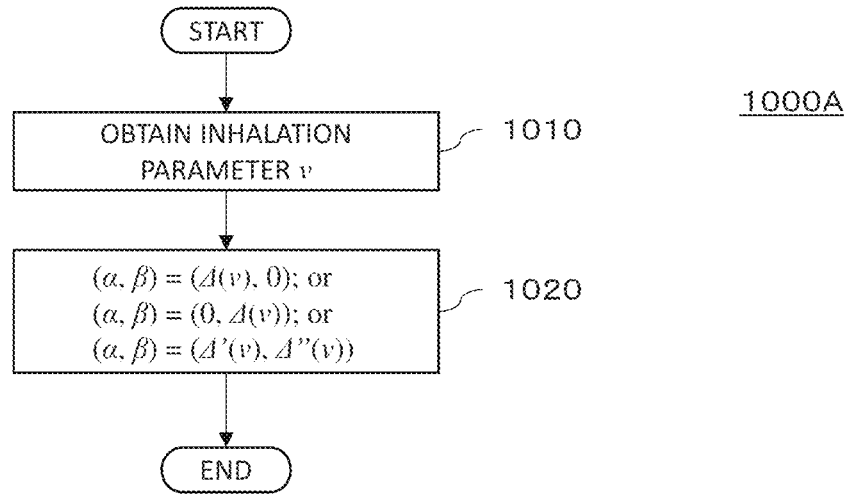

In step 842, a process 1000A illustrated by the flowchart in FIG. 10A can be performed. A reference numeral 1010 denotes a step of obtaining a flow velocity v as a parameter representing the inhalation strength. The parameter to be obtained may be a flow rate or a pressure. A reference numeral 1020 denotes a step of setting to α=0 and β=Δ(v), setting to α=Δ(v) and β=0, or setting α=Δ'(v) and β=Δ"(v) based on the obtained parameter.

Note that, in step 1020, a value corresponding to the temperature threshold $T'_{thre}(v)$ or the temperature change threshold $\Delta T'_{thre}(v)$ used in steps 850A to 850D may be directly set without setting α and β. The value corresponding to the temperature threshold $T'_{thre}(v)$ or the temperature change threshold $\Delta T'_{thre}(v)$ may be achieved by the table using, as a key, a parameter representing the inhalation strength such as the flow velocity v.

3-2-5-2. When Inhalation Strength is not Taken into Consideration

When, although the temperature reached by the load 132 is increased or decreased due to the inhalation, the magnitude of the increase or decrease in temperature is not changed according to the inhalation strength, or although the temperature change of the load 132 per a predetermined time period Δt or per a predetermined amount of electric power ΔW is increased or reduced due to the inhalation, the degree of the temperature change is not changed according to the inhalation strength, the above-described $T'_{satmax}(v)$ and $T'_{depmax}(v)$, or $\Delta T'_{sat}(v)$ and $\Delta T'_{dep}(v)$ can be assumed to be constants.

In addition, when the magnitude of increase or decrease in temperature reached by the load 132 or the degree of increase or decrease in the temperature change of the load 132 is not changed due to the inhalation having a range of strength, or is not changed due to the inhalation having a certain strength or higher, the above-described $T'_{satmax}(v)$ and $T'_{depmax}(v)$ according to the inhalation strength, or $\Delta T'_{sat}(v)$ and $\Delta T'_{dep}(v)$ can be assumed to be constants $T'_{satmax}$ and $T'_{depmax}$, or $\Delta T'_{sat}$ and $\Delta T'_{dep}$. For example, in the aerosol inhalator 100 having a certain structure, it has been found that the magnitude of increase in temperature reached by the load 132 or the degree of increase in the above-described temperature change of the load 132 is not changed due to the inhalation strength causing the flow rate of 55 cc (cm³) or more per 3 seconds.

Figure 10B:
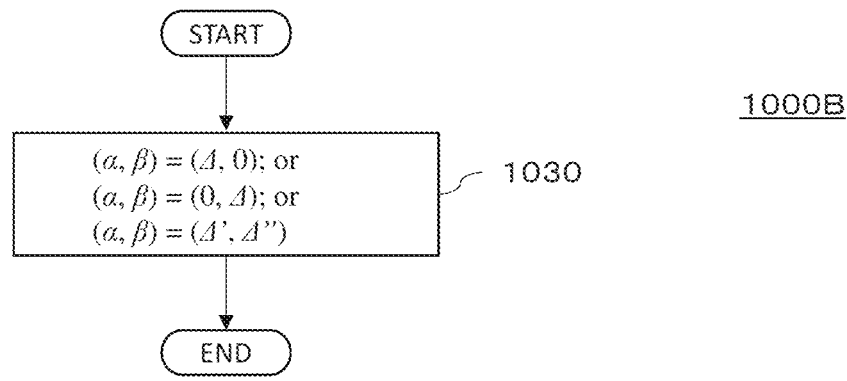

In such cases, the functions Δ(v), Δ'(v) and Δ"(v) are assumed to be the predetermined constants Δ, Δ', and Δ" which satisfy the corresponding inequalities, respectively, and in step 842, a process 1000B illustrated by the flowchart in FIG. 10B can be performed. A reference numeral 1030 denotes a step of setting to α=0 and β=Δ, setting to α=Δ and β=0, or setting α=Δ' and β=Δ". That is, in the exemplary process 1000B, it is not necessary to obtain the parameter representing the inhalation strength.

Note that, in step 1030, a value corresponding to the temperature threshold $T'_{thre}$ or the temperature change threshold $\Delta T'_{thre}$ used in steps 850A to 850D may be directly set without setting α and β.

As described above, the correction value α has an effect of correcting a variable (value) for comparing with the threshold $T_{thre}$ or $\Delta T_{thre}$ or the like (hereinafter, referred to as the "$T_{thre}$ or the like"), and the correction value β has an effect of correcting the threshold $T_{thre}$. In the case of α=0 and β=Δ(v), this means that only the threshold $T_{thre}$ or the like of the variable (value) to be compared with the threshold $T_{thre}$ or the like and the threshold $T_{thre}$ or the like is corrected. In the case of α=Δ(v) and β=0, this means that only the variable (value) to be compared with the threshold $T_{thre}$ or the like of the variable (value) to be compared with the threshold $T_{thre}$ or the like and the threshold $T_{thre}$ or the like is corrected. In the case of α=Δ'(v) and β=Δ"(v), this means that both of the variable (value) to be compared with the threshold $T_{thre}$ or the like and the threshold $T_{thre}$ or the like are corrected.

3-2-6. Regarding Step 844

Figure 10C:
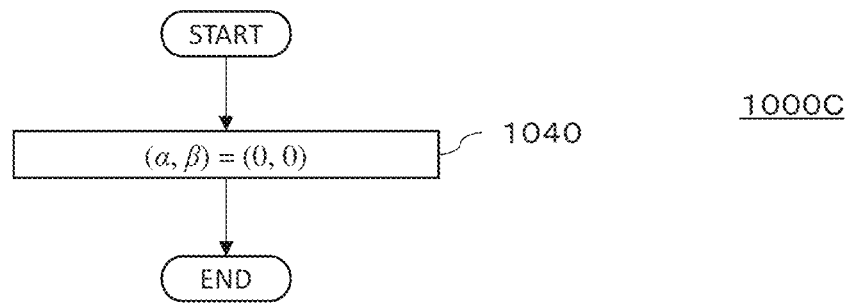

FIG. 10C is a flowchart of an exemplary process 1000C performed in step 844. A reference numeral 1040 denotes a step of setting to α=0 and β=0. Here, "0" is an example of a default value. This step enables the comparison using the threshold set without taking into consideration the inhaling by the user on the aerosol inhalator 100, that is, set at the time of non-inhaling, in steps 850A to 850D.

Note that, in step 1040, a value corresponding to the temperature threshold $T'_{thre}(v)$ or $T'_{thre}$, or the temperature change threshold $\Delta T'_{thre}$ used in steps 850A to 850D may be directly set without setting α and β.

3-2-7. Regarding Step 850E or 850G (Hereinafter, Referred to as the "Step 850E or the Like")

3-2-7-1. Regarding Overview of Determination

In step 850E or the like, when a predetermined inequality which is a function of the value x relating to the heater temperature is satisfied, it can be determined that the aerosol source is sufficient, and when the inequality is not satisfied, it can be determined that the aerosol source is not sufficient. Such an inequality depends on whether the value x relating to the heater temperature is increased or decreased when the temperature of the load 132 is increased, and whether the temperature reached by the load 132 is increased or decreased as described above with respect to the graph 700. In the description below, it is assumed that the value x relating to the heater temperature is a value of the temperature of the load 132, and the value x relating to the heater temperature is increased when the temperature of the load 132 is increased.

As described above, when, although the temperature reached by the load 132 is increased or decreased due to the inhalation, the magnitude of the increase or decrease in temperature is not changed according to the inhalation strength, it can be determined whether the residual amount of the aerosol source in the retainer and the like is sufficient by comparing the temperature of the load 132 with the temperature threshold $T'_{thre}$ as a constant. This comparison can be represented by the following inequality (41).

[Formula 27]

$$x \leq T'_{thre} \tag{41}$$

Here, the temperature threshold which can be obtained by an experiment, and is set without taking into consideration the inhaling on the aerosol inhalator 100 is represented as $T_{thre}$ (equal to or higher than the boiling point $T_{B.P.}$ or the like of the aerosol source and equal to or lower than the equilibrium temperature $T_{equi.}$, accordingly, may be $T_{B.P.}$), and the correction value which may be positive or negative value is represented as γ.

[Formula 28]
$$T'_{thre} = T_{thre} + \gamma$$

Using the above expression, the inequality (41) can be rearranged to the following inequality (42).

[Formula 29]
$$x \leq T_{thre} + \gamma \tag{42}$$

Accordingly, in step 850E and the like, it can be determined whether the inequality (41) or (42) is satisfied. That is, it may be determined that the aerosol source is sufficient when the inequality (42) holds, and it may be determined that the aerosol source is depleted or insufficient when the inequality (42) does not hold. Note that these inequality signs in these inequalities may be "<."

3-2-7-2. Regarding Parameter Used for Determination

When the temperature reached by the load 132 is increased due to the inhalation, the temperature threshold $T'_{thre}$ may be constant $T'_{satmax}$ or more and $T_{equi.}$ or less, or constant $T'_{satmax}$ or more and constant $T'_{depmax}$ or less. This condition can be represented by the following inequality (43) or (44).

[Formula 30]
$$T'_{satmax} \leq T'_{thre} \leq T_{equi.} \tag{43}$$
$$T'_{satmax} \leq T_{thre} + \gamma \leq T_{equi.}$$
$$T'_{satmax} - T_{thre} \leq \gamma \leq T_{equi.} - T_{thre}$$

$$T'_{satmax} \leq T'_{thre} \leq T'_{depmax} \tag{44}$$
$$T'_{satmax} \leq T_{thre} + \gamma \leq T'_{depmax}$$
$$T'_{satmax} - T_{thre} \leq \gamma \leq T'_{depmax} - T_{thre}$$

Here, since the inequalities (43) and (44) do not depend on the inhalation strength, the correction value γ or the temperature threshold $T'_{thre}$ which satisfies these inequalities can be obtained in advance. Note that when γ which satisfies these inequalities is a positive value, the right side of the inequality (42) is a value obtained by adding the positive predefined value γ to the temperature threshold $T_{thre}$ ($T_{thre}$ may be $T_{B.P.}$). In addition, when $T'_{depmax} = T_{equi.} + \delta$ ($0 < \delta \leq T'_{depmax} - T_{equi.}$), the inequality (43) shows that γ may be $T_{equi.} - T_{thre} + \delta$ (as described above, $T_{thre}$ may be $T_{B.P.}$).

In another aspect, when the temperature reached by the load 132 is increased due to the inhalation, the temperature threshold $T'_{thre}$ may be $T_{thre} + \varepsilon_1$ (as described above, $T_{thre}$ may be $T_{B.P.}$) as described above. Here, since $\varepsilon_1$ (is, by definition, a positive value) does not depend on the inhalation strength, $\varepsilon_1$ may be used as γ in the inequality (42).

Note that even when the magnitude of increase in temperature reached by the load 132 is not changed due to the inhalation having a range of strength, or is not changed due to the inhalation having a certain strength or higher, the above-described $T'_{satmax}(v)$, $T'_{depmax}(v)$ and $\varepsilon_1(v)$ according to the inhalation strength can be constants $T'_{satmax}$, $T'_{depmax}$ and $\varepsilon_1$. As described above, for example, in the aerosol inhalator 100 having a certain structure, it has been found that the magnitude of increase in temperature reached by the load 132 is not changed due to the inhalation strength causing the flow rate of 55 cc (cm³) or more per 3 seconds.

In addition, when the temperature reached by the load 132 is decreased due to the inhalation, the temperature threshold $T'_{thre}(v)$ may be $T_{B.P.}$ or more and a constant $T'_{depmax}$ or less, or a constant $T'_{satmax}$ or more and $T'_{depmax}$ or less, as described above. This condition can be represented by the following inequality (45) or (46).

[Formula 31]
$$T_{B.P.} \leq T'_{thre} \leq T'_{depmax} \tag{45}$$
$$T_{B.P.} \leq T_{thre} + \gamma \leq T'_{depmax}$$
$$T_{B.P.} - T_{thre} \leq \gamma \leq T'_{depmax} - T_{thre}$$

$$T'_{satmax} \leq T'_{thre} \leq T'_{depmax} \tag{46}$$
$$T'_{satmax} \leq T_{thre} + \gamma \leq T'_{depmax}$$
$$T'_{satmax} - T_{thre} \leq \gamma \leq T'_{depmax} - T_{thre}$$

Here, since the inequalities (45) and (46) do not depend on the inhalation strength, the correction value γ or the temperature threshold $T'_{thre}$ which satisfies these inequalities can be obtained in advance. Note that when γ which satisfies these inequalities is a negative value, the right side of the inequality (42) is a value obtained by subtracting the positive predefined value |γ| from the temperature threshold $T_{thre}$ (since the temperature reached by the load 132 is decreased due to the inhalation, $T'_{depmax} < T_{equi.}$ holds, and therefore $T_{thre}$ may be $T'_{depmax}$.)

In another aspect, when the temperature reached by the load 132 is decreased due to the inhalation, the temperature threshold $T'_{thre}$ may be $T_{thre} - \varepsilon_2$ (as described above, $T_{thre}$ may be $T'_{depmax}$) as described above. Here, since $\varepsilon_2$ (is, by definition, a positive value) does not depend on the inhalation strength, $-\varepsilon_2$ may be used as γ in the inequality (42).

The temperature threshold $T'_{thre}$ can be obtained in advance. Accordingly, the determination in step 850E and the like can be performed using the inequality (41), as long as the value x relating to the heater temperature is obtained using the sensor 112. In particular, it can be determined whether the aerosol source is sufficient, using the temperature threshold $T'_{thre}$ which satisfies the inequality (45) or (46), even when the temperature threshold $T'_{thre}$ and the value x relating to the heater temperature are not corrected according to the presence or absence of the inhalation in the exemplary process 800E and the like.

Note that even when the magnitude of decrease in temperature reached by the load 132 is not changed due to the inhalation having a range of strength, or is not changed due to the inhalation having a certain strength or higher, the above-described $T'_{satmax}(v)$, $T'_{depmax}(v)$ and $\varepsilon_2(v)$ according to the inhalation strength can be constants $T'_{satmax}$, $T'_{depmax}$, and $\varepsilon_2$. Such an inhalation may have the strength causing the flow rate of 55 cc (cm³) per 3 seconds.

In the system in which the magnitude of change in the temperature of the load 132 due to the inhalation depends on the inhalation strength, the temperature threshold $T'_{thre}$ may be set with respect to a predetermined inhalation strength. As an example, the predetermined inhalation strength may be set based on the statistical information obtained in advance from the inhalation information of a plurality of users. As an example, the predetermined inhalation strength may be the strength causing the flow rate of 55 cc (cm³) per 3 seconds.

In this way, even when in the system in which the magnitude of change in the temperature of the load 132 due to the inhalation depends on the inhalation strength, it can be determined whether the aerosol source is sufficient even when the temperature threshold $T'_{thre}$ and the value x relating to the heater temperature are not corrected according to the presence or absence of the inhalation in the exemplary process 800E and the like.

3-2-7-3. Remarks about Determination

In the above description, in the above description, although it is assumed that the value x relating to the heater temperature is a value of the temperature of the load, note that when the value x relating to the heater temperature which is not the value of the temperature of the load is used, γ is a value obtained based on such a value x relating to the heater temperature. In particular, note that when the value x relating to the heater temperature is decreased in the case where the temperature of the load 132 is increased, the inequality signs in the inequalities (41) to (42) may be reversed or the like.

3-2-8. Regarding Step 850F and 850H (Hereinafter, Referred to as the "Step 850F or the Like")

3-2-8-1. Regarding Overview of Determination

In step 850F or the like, when a predetermined inequality, which is a function of the times $t_1$ and $t_2$ and the values $x(t_1)$ and $x(t_2)$ relating to the heater temperature, is satisfied, it can be determined that the aerosol source is sufficient, and when the inequality is not satisfied, it can be determined that the aerosol source is not sufficient. Such an inequality depends on whether the value x relating to the heater temperature is increased or decreased when the temperature of the load 132 is increased, and whether the temperature rise width of the load 132 per a predetermined time period is increased or decreased due to the inhalation as described above with respect to temperature change 750. In the description below, it is assumed that the value x relating to the heater temperature is a value of the temperature of the load 132, and the value x relating to the heater temperature is increased when the temperature of the load 132 is increased.

As described above, when, although the temperature change of the load 132 per a predetermined time period Δt is increased or decreased due to the inhalation, the degree of the temperature change is not changed according to the inhalation strength, it can be determined whether the residual amount of the aerosol source in the retainer and the like is sufficient by comparing the temperature change of the load 132 per a predetermined time period Δt with the temperature change threshold $\Delta T'_{thre}$ as a constant.

Specifically, this comparison can be represented by the following inequality (47).

[Formula 32]

$$\frac{x(t_2)-x(t_1)}{t_2-t_1} \le Thre'_1 \tag{47}$$

Here, the threshold which can be obtained by an experiment, and can be used for determining whether the residual amount of the aerosol source is sufficient without taking into consideration the inhaling on the aerosol inhalator 100 is represented as $Thre_1$ (corresponding to $\Delta T_{thre}/\Delta t$ in FIG. 3. $\Delta T_{thre}$ is $\Delta T_{sat}$ or more and $\Delta T_{dep}$ or less), and the correction value which may be positive or negative value is represented as γ.

$$Thre'_1=Thre_1+\gamma \quad \text{[Formula 33]}$$

Using the above expression, the inequality (47) can be rearranged to the following inequality (48).

[Formula 34]

$$\frac{x(t_2)-x(t_1)}{t_2-t_1} \le Thre_1+\gamma \tag{48}$$

In addition, this comparison can be represented by the following inequality (49) or (50) when $Thre'_2=Thre_2+\gamma$ ($Thre_2$ corresponds to $\Delta T_{thre}/\Delta W$ in FIG. 3.).

[Formula 35]

$$\frac{x(t_2)-x(t_1)}{\int_{t_1}^{t_2} P(t)dt} \le Thre'_2 \tag{49}$$

$$\frac{x(t_2)-x(t_1)}{\int_{t_1}^{t_2} P(t)dt} \le Thre_2+\gamma \tag{50}$$

Accordingly, in step 850F and the like, it can be determined whether any one of the inequalities (47) to (50) is satisfied. That is, it may be determined that the aerosol source is sufficient when the inequality (48) or (50) holds, and it may be determined that the aerosol source is depleted or insufficient when the inequality (48) or (50) does not hold.

Note that when the inequality (49) or (50) is used, rather than determining the time $t_2$ as the time $t_1$+a predetermined time period Δt, the controller 106 may monitor the total amount of electric power supplied to the load 132 from the time $t_1$ and determine, as the time $t_2$, the point of time when the total amount of electric power becomes a predetermined amount of electric power. In addition, these inequality signs in these inequalities may be "<."

3-2-8-2. Regarding Parameter Used for Determination

Hereinafter, it is assumed that the inequality (48) is used in step 850F and the like.

When the temperature change of the load 132 per a predetermined time period Δt is increased due to the inhalation, the temperature change threshold $\Delta T'_{thre}$ may be a constant $\Delta T'_{sat}$ or more and $\Delta T_{dep}$ or less, or a constant $\Delta T'_{sat}$ or more and a constant $\Delta T'_{dep}$ or less as described above. This condition can be represented by the following expression (51) or (52).

[Formula 36]

$$\frac{\Delta T'_{sat}}{\Delta t} \le Thre'_1 \le \frac{\Delta T_{dep}}{\Delta t} \tag{51}$$

$$\frac{\Delta T'_{sat}}{\Delta t} \le Thre_1+\gamma \le \frac{\Delta T_{dep}}{\Delta t}$$

$$\frac{\Delta T'_{sat}}{\Delta t} - Thre_1 \le \gamma \le \frac{\Delta T_{dep}}{\Delta t} - Thre_1$$

$$\frac{\Delta T'_{sat}}{\Delta t} \le Thre'_1 \le \frac{\Delta T'_{dep}}{\Delta t} \tag{52}$$

$$\frac{\Delta T'_{sat}}{\Delta t} \le Thre_1+\gamma \le \frac{\Delta T'_{dep}}{\Delta t}$$

$$\frac{\Delta T'_{sat}}{\Delta t} - Thre_1 \leq \gamma \leq \frac{\Delta T'_{dep}}{\Delta t} - Thre_1$$

Here, since the inequalities (51) and (52) do not depend on the inhalation strength, the correction value γ or the temperature threshold Thre'$_1$ which satisfies these inequalities can be obtained in advance.

In another aspect, when the temperature change of the load 132 per a predetermined time period Δt is increased due to the inhalation, the temperature change threshold ΔT'$_{thre}$ may be ΔT'$_{thre}$+Δε$_1$ as described above. Here, since Δε$_1$ does not depend on the inhalation strength, Δε$_1$/Δt may be used as a correction value γ.

In addition, when the temperature change of the load 132 per a predetermined time period Δt is decreased due to the inhalation, the temperature change threshold ΔT'$_{thre}$ may be a constant ΔT$_{sat}$ or more and a constant ΔT'$_{dep}$ or less, or a constant ΔT'$_{sat}$ or more and a constant ΔT'$_{dep}$ or less as described above. This condition can be represented by the following expression (53) or (54).

[Formula 37]

$$\frac{\Delta T_{sat}}{\Delta t} \leq Thre'_1 \leq \frac{\Delta T'_{dep}}{\Delta t} \quad (53)$$

$$\frac{\Delta T_{sat}}{\Delta t} \leq Thre_1 + \gamma \leq \frac{\Delta T'_{dep}}{\Delta t}$$

$$\frac{\Delta T_{sat}}{\Delta t} - Thre_1 \leq \gamma \leq \frac{\Delta T'_{dep}}{\Delta t} - Thre_1$$

$$\frac{\Delta T'_{sat}}{\Delta t} \leq Thre'_1 \leq \frac{\Delta T'_{dep}}{\Delta t} \quad (54)$$

$$\frac{\Delta T'_{sat}}{\Delta t} \leq Thre_1 + \gamma \leq \frac{\Delta T'_{dep}}{\Delta t}$$

$$\frac{\Delta T'_{sat}}{\Delta t} - Thre_1 \leq \gamma \leq \frac{\Delta T'_{dea}}{\Delta t} - Thre_1$$

Here, since the inequalities (53) and (54) do not depend on the inhalation strength, the correction value γ or the threshold Thre'$_1$ which satisfies these inequalities can be obtained in advance.

In another aspect, when the temperature change of the load 132 per a predetermined time period Δt is decreased due to the inhalation, the temperature change threshold ΔT'$_{thre}$ may be ΔT$_{thre}$−Δε$_2$ as described above. Here, since Δε$_2$ does not depend on the inhalation strength, −Δε$_2$/Δt may be used as a correction value γ.

The threshold Thre'$_1$ can be obtained in advance. Accordingly, the determination in step 850F and the like can be performed using the inequality (47), as long as the left side of the inequality (47) is obtained using the sensor 112. In particular, it can be determined whether the aerosol source is sufficient, using the threshold Thre'$_1$ which satisfies the inequality (53) or (54), even when the threshold Thre'$_1$ and the left side of the inequality (47) are not corrected according to the presence or absence of the inhalation in the exemplary process 800F and the like.

Note that, when the degree of increase or decrease in the temperature change of the load 132 per a predetermined time period Δt or a predetermined amount of electric power ΔW is not changed due to the inhalation having a range of strength, or is not changed due to the inhalation having a certain strength or higher, the above-described ΔT'$_{satmax}$(v), ΔT'$_{depmax}$(v). Δε$_1$(v) and Δε$_2$ according to the inhalation strength can be assumed to be constants ΔT'$_{satmax}$, ΔT'$_{depmax}$, Δε$_1$ and Δε$_2$. Such an inhalation may have t the strength causing the flow rate of 55 cc (cm$^3$) per 3 seconds.

In the system in which the magnitude of change in the temperature of the load 132 due to the inhalation depends on the inhalation strength, the threshold Thre'$_1$ may be set with respect to a predetermined inhalation strength. As an example, the predetermined inhalation strength may be set based on the statistical information obtained in advance from the inhalation information of a plurality of users. As an example, the predetermined inhalation strength may be the strength causing the flow rate of 55 cc (cm$^3$) per 3 seconds.

In this way, even when in the system in which the magnitude of change in the temperature of the load 132 due to the inhalation depends on the inhalation strength, it can be determined whether the aerosol source is sufficient even when the threshold Thre'$_1$ and the left side of the inequality (47) are not corrected according to the presence or absence of the inhalation in the exemplary process 800F and the like.

3-2-8-3. Remarks about Determination

In the above description, although it is assumed that the inequality (48) is used in step 850F or the like, when the inequality (49) or (50) is used in step 850F or the like, Δt of the denominator in the above-described inequality may be replaced with ΔW. In addition, in the above description, although it is assumed that the value x relating to the heater temperature is a value of the temperature of the load, note that when the value x relating to the heater temperature which is not the value of the temperature of the load is used, the correction value γ may be a value obtained based on such a value x relating to the heater temperature. In particular, note that when the value x relating to the heater temperature is decreased in the case where the temperature of the load 132 is increased, the inequality signs in the inequalities (47) to (50) may be reversed.

3-2-9. Regarding Steps 852 and 858

Figure 11:
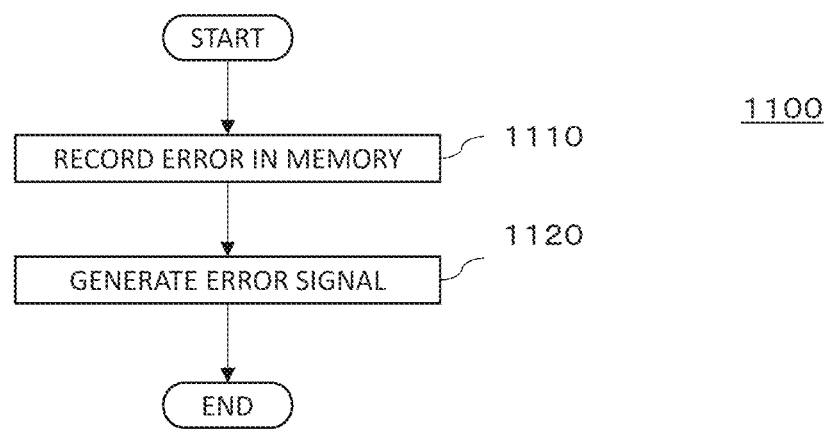

FIG. 11 is a flowchart of a more specific exemplary process 1100 performed in step 852 in the exemplary processes 800A to 800D.

A reference numeral 1110 denotes a step of storing an error in a memory. A reference numeral 1120 denotes a step of generating an error signal.

Note that in step 858 in the exemplary processes 800E to 800H, a step of initializing the above-described counter N can be performed in addition to the step included in the exemplary process 1100.

4. CONCLUSION

In the above description, the embodiments of the present disclosure have been described as the aerosol inhalator and the method of operating the aerosol inhalator. However, it will be appreciated that the present disclosure, when executed by a processor, can be implemented as a program that causes the processor to perform the method, or as a computer readable storage medium storing the same program.

The embodiments of the present disclosure are described thus far, and it should be understood that these embodiments are only illustration, and do not limit the scope of the present disclosure. It should be understood that modification, addition, alternation and the like of the embodiments can be properly performed without departing from the gist and the scope of the present disclosure. The scope of the present disclosure should not be limited by any of the aforementioned embodiments, but should be specified by only the claims and the equivalents of the claims.

REFERENCE SIGNS LIST

100A, 100B Aerosol inhalator
102 Main body
104A Cartridge
104B Aerosol generating article
106 Controller
108 Notifying part
110 Power supply
112A to 112D Sensor
114 Memory
116A Reservoir
116B Aerosol base
118A, 118B Atomizing part
120 Air intake channel
121 Aerosol flow path
122 Suction port part
124 Flow direction of mixing fluid of aerosol and air
130 Retainer
132 Load
134, 200 Circuit
202 First circuit
204 Second circuit
206, 210, 214 FET
208 Converter
212 Resistor
216 Diode
218 Inductor
220 Capacitor
300, 500, 600, 700 Graph showing temperature profile of load
310, 460, 470, 480, 510A, 510B, 510C, 610A, 610B, 610C, 710A, 710B, 710C Temperature profile when aerosol source is sufficient
320, 520A, 520B, 620A, 620B, 720A, 720B Temperature profile when aerosol source is not sufficient
350, 550, 650, 750 Temperature change of load per predetermined time period
360, 560A, 560B, 560C, 660A, 660B, 660C, 760A, 760B, 760C Temperature change when aerosol source is sufficient
370, 570A, 570B, 670A, 670B, 770A, 770B Temperature change when aerosol source is not sufficient
400A, 400B, 400C Exemplary structure in a vicinity of load
410 Component corresponding to retainer and the like
420 At least part of component corresponding to load
430 Flow direction of air stream caused by inhalation

What is claimed is:

1. A control device for an aerosol inhalator, comprising:
a first sensor for obtaining a first value relating to a temperature of a load which atomizes an aerosol source stored in a reservoir or retained by an aerosol base using heat generated by supply of electric power;
a second sensor configured to detect an inhalation and an inhalation strength; and
a controller,
wherein the controller is configured to:
determine, based on a second value based on the first value and a threshold, whether the aerosol source in the reservoir or the aerosol base is depleted or insufficient, and
correct the threshold according to the inhalation strength when detecting the inhalation so that the corrected threshold is compared with the second value in a steady state to prevent a false determination of a residual amount of the aerosol source, and, in the determination, compare the second value in the steady state and the corrected threshold,
wherein the second value is a value of a ratio between a change amount of the first value due to an amount of electric power supplied to the load and the amount of electric power supplied.

2. The control device for the aerosol inhalator according to claim 1, wherein
the aerosol inhalator is configured to decrease a temperature of the load when the inhalation is performed during power supply to the load or during aerosol generation of the load, and
the controller is configured to, when detecting the inhalation:
correct the second value to be increased or the threshold to be decreased in a case that the first value is decreased as the temperature of the load is decreased, or
correct the second value to be decreased or the threshold to be increased in a case that the first value is increased as the temperature of the load is decreased.

3. The control device for the aerosol inhalator according to claim 1, wherein
the aerosol inhalator is configured to increase the temperature of the load when the inhalation is performed during the power supply to the load or during aerosol generation of the load, and
the controller is configured to, when detecting the inhalation:
correct the second value to be decreased or the threshold to be increased in a case that the first value is increased as the temperature of the load is increased, or
correct the second value to be increased or the threshold to be decreased in a case that the first value is decreased as the temperature of the load is increased.

4. An aerosol inhalator, comprising:
the control device for the aerosol inhalator according to claim 1;
a channel in which air taken by the inhalation flows; and
the load disposed in a position not to be in contact with the air outside and inside the channel,
wherein the controller is configured to, when detecting the inhalation:
correct the second value to be decreased or the threshold to be increased in a case that the first value is increased as the temperature of the load is increased, or
correct the second value to be increased or the threshold to be decreased in a case that the first value is decreased as the temperature of the load is increased.

5. An aerosol inhalator comprising:
the control device for the aerosol inhalator according to claim 1;
an outer tube;
an inner tube disposed in the outer tube;
the reservoir disposed or formed between the outer tube and the inner tube;
the load disposed in the inner tube; and
a retainer retained in a position where the load is capable of heating the aerosol source supplied by the reservoir, wherein the controller is configured to, when detecting the inhalation, correct at least one of the second value and the threshold by a constant amount regardless of a strength of the inhalation.

6. The control device for the aerosol inhalator according claim 1, further comprising:
   a first circuit having a first switch; and
   a second circuit having a second switch, and having a resistance value higher than a resistance value of the first circuit and connected in parallel to the first circuit,
   wherein the first sensor is configured to output, as the first value, a value relating to a resistance value of the load which changes depending on a temperature, and
   the controller is configured to determine occurrence of the depletion or the insufficiency based on the first value while only the second circuit functions.

7. A method of operating a control device for an aerosol inhalator,
   the control device comprising:
   a first sensor for obtaining a first value relating to a temperature of a load which atomizes an aerosol source stored in a reservoir or retained by an aerosol base using heat generated by supply of electric power;
   a second sensor configured to detect an inhalation and an inhalation strength; and
   a controller,
   the method comprising, by the controller:
   determining depletion or insufficiency of the aerosol source in the reservoir or the aerosol base based on a second value based on the first value and a threshold, comprising:
   correcting the threshold according to the inhalation strength when detecting the inhalation so that the corrected threshold is compared with the second value in a steady state to prevent a false determination of a residual amount of the aerosol source; and
   comparing the second value in the steady state and the corrected threshold,
   wherein the second value is a value of a ratio between a change amount of the first value due to an amount of electric power supplied to the load and the amount of electric power supplied.

8. A non-transitory computer-readable storage medium storing a program that causes a processor to perform the method according to claim 7, when executed by the processor.

* * * * *